(12) United States Patent
Beauverger et al.

(10) Patent No.: US 8,975,250 B2
(45) Date of Patent: Mar. 10, 2015

(54) 5 OXO-5,8-DIHYDROPYRIDO[2,3-D]PYRIMIDINE DERIVATIVES AS CAMKII KINASE INHIBITORS FOR TREATING CARDIOVASCULAR DISEASES

(75) Inventors: Philippe Beauverger, Plaisir (FR); Guillaume Begis, Versailles (FR); Sandrine Biscarrat, Gif sur Yvette (FR); Olivier Duclos, Gentilly (FR); Gary McCort, Paris (FR)

(73) Assignee: SANOFI, Paris (FR)

( * ) Notice: Subject to any disclaimer, the term of this patent is extended or adjusted under 35 U.S.C. 154(b) by 0 days.

(21) Appl. No.: 13/544,209

(22) Filed: Jul. 9, 2012

(65) Prior Publication Data
US 2012/0277220 A1 Nov. 1, 2012

Related U.S. Application Data

(63) Continuation of application No. PCT/FR2011/050019, filed on Jan. 6, 2011.

(30) Foreign Application Priority Data

Jan. 8, 2010 (FR) ...................... 10 50103

(51) Int. Cl.
| | | |
|---|---|---|
| C07D 471/04 | (2006.01) |
| A61K 31/519 | (2006.01) |
| A61K 31/496 | (2006.01) |
| A61K 31/5377 | (2006.01) |
| A61K 31/541 | (2006.01) |
| A61K 31/551 | (2006.01) |
| A61P 1/16 | (2006.01) |
| A61P 13/12 | (2006.01) |
| A61P 25/00 | (2006.01) |
| A61P 25/16 | (2006.01) |
| A61P 25/28 | (2006.01) |
| A61P 29/00 | (2006.01) |
| A61P 9/00 | (2006.01) |
| A61P 9/06 | (2006.01) |
| A61P 9/10 | (2006.01) |
| C07D 239/47 | (2006.01) |

(52) U.S. Cl.
CPC ................ C07D 471/04 (2013.01)
USPC ............ 514/218; 514/264.11; 514/234.2; 514/227.8; 514/252.16; 514/210.01; 540/575; 544/117; 544/279; 544/317; 544/58.2

(58) Field of Classification Search
CPC ............... C07D 471/04; A61K 31/519
USPC .................... 544/279; 514/264.11
See application file for complete search history.

(56) References Cited

FOREIGN PATENT DOCUMENTS

| EP | 1815867 | 8/2007 |
|---|---|---|
| WO | WO 96/34867 | 11/1996 |
| WO | WO 2005/105801 | 11/2005 |
| WO | WO 2009/042906 | 4/2009 |
| WO | WO 2010004198 | * 1/2010 |

OTHER PUBLICATIONS

International Search Report for WO2011/086306 dated Jul. 21, 2011.
Huang, et al., Design and Synthesis of a Pyrido[2,3-d]Pyrimidin-5-One Class of Anti-Inflammatory FMS Inhibitors, Bioorganic & Medicinal Chemistry Letters, vol. 18, (2008), pp. 2355-2361.
Mavunkel, et al., Pyrimidine-Based Inhibitors of CaMKIIdelta, Bioorganic & Medicinal Chemistry Letters, vol. 18, (2008), pp. 2404-2408.
Zhang, et al., Calmodulin Kinase II inhibition Protects Against Structural Heart Disease, Nature Medicine, vol. 11, No. 4, (2005), pp. 409-417.
Rellos, et al., Structure of the CaMKIIdelta/Calmodulin Complex Reveals the Molecular Mechanism of CaMKII Kinase Activation, PLOS Biology, vol. 8, No. 7, (2010), pp. 1-12, e1000426.
Hagemann, et al., Expression of Ca2+/Calmodulin-Dependent Protein Kinase II Delta-Subunit Isoforms in Rats With Hypertensive Cardiac Hypertrophy, Molecular and Cellular Biochemistry, vol. 220, pp. 69-76, (2001).
Boknik, et al., Enhanced Protein Phoshorylation in Hypertensive Hypertrophy, Cardiovascular Research, vol. 51, (2001), pp. 717-728.
Hempel, et al., Hypertrophic Phenotype of Cardiac Calcium/Calmodulin-Dependent Protein Kinase II is Reversed by Angiotensin Converting Enzyme Inhibition, Basic Res Cardiol, vol. 97, Suppl. 1, pp. I/96-I/101, (2002).
Colomer, et al., Pressure Overload Selectivity Up-Regulates Ca2+/Calmodulin-Dependent Protein Kinase II in Vivo, Molecular Endocrinology, vol. 17, No. 2, pp. 183-192, (2003).
Zhang, et al., The DeltaC Isoform of CaMKII Is Activated in Cardiac Hypertrophy and Induces Dilated Cardiomyopathy and Heart Failure, Circ. Res., (2003), vol. 92, pp. 912-919.
Currie, et al., Calcium/Calmodulin-Dependent Protein Kinase II Activity is Increased in Sarcoplasmic Reticulum From Coronary Artery Ligated Rabbit Hearts, FEBS Letters, vol. 459, (1999), pp. 244-248.

(Continued)

Primary Examiner — Susanna Moore
(74) Attorney, Agent, or Firm — Scully, Scott, Murphy & Presser P.C.

(57) ABSTRACT

The present invention relates to 5-oxo-5,8-dihydropyrido[2,3-d]pyrimidine derivatives having Formula (I)

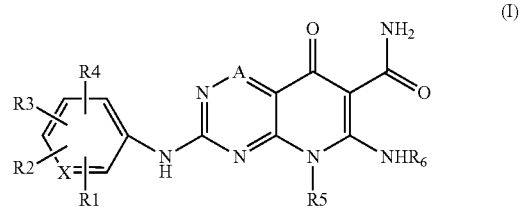

as defined herein, their preparation and their therapeutic use.

13 Claims, No Drawings

(56) References Cited

OTHER PUBLICATIONS

Hoch, et al., Identification and Expression of Delta-Isoforms of the Multifunctional Ca2 + /Calmodulin-Dependent Protein Kinase in Failing and Nonfailing Human Myocardium, Cir. Res., (1999), vol. 84, pp. 713-721.

Kirchhefer, et al., Activity of CAMP-Dependent Protein Kinase and Ca2+ /Calmodulin-Dependent Protein Kinase in Failing and Nonfailing Human Hearts, Cardiovascular Research, vol. 42, (1999), p. 254-261.

Zhang, et al., The Cardiac-Specific Nuclear DeltaB Isoform of Ca2+ /Calmodulin-Dependent Protein Kinase II Induces Hypertrophy and Dilated Cardiomyopathy Associated With Increased Protein Phosphatase 2A Activity, The Journal of Biological Chemistry, vol. 277, No. 2, (2002), pp. 1261-1267.

Maier, et al., Transgenic CaMKIIdeltaC, Overexpression Uniquely Alters Cardiac Myocte Ca2+ Handling: Reduced SR Ca 2+ Load and Activated SR Ca2+ Release, Circ. Res., vol. 92, pp. 904-911, (2003).

Bers, Beyond Beta Blockers, Nature Medicine, vol. 11, No. 4, (2005), pp. 379-380.

Yang, et al., Calmodulin Kinase II Inhibition Protects Against Myocardial Cell Apoptosis in Vivo, Am J Physiol Heart Circ Physiol, vol. 291, pp. H3065-H3075, (2006).

Vila-Petroff, et al., CaMKII Inhibition Protects Against Necrosis and Apoptosis in Irreversible Ischemia-Reperfusion Injury, Cardiovascular Research, vol. 73, (2007), pp. 689-698.

Wu, et al., Calmodulin Kinase II and Arrhythmias in a Mouse Model of Cardiac Hypertrophy, Circulation, (2002), vol. 106, pp. 1288-1293.

Khoo, et al., Death, Cardiac Dysfunction, and Arrhythmias Are Increased by Calmodulin Kinase II in Calcineurin Cardiomyopathy, Circulation, (2006), vol. 114, pp. 1352-1359.

Backs, et al., The Delta Isoform of CaM Kinase II is Required for Pathological Cardiac Hypertrophy and Remodeling After Pressure Overload, PNAS, (2009), pp. 2342-2347, vol. 106, No. 7.

Ling, et al., Requirement for Ca2+/Calmodulin-Dependent Kinase II in the Transition From Pressure Overload-Induced Cardiac Hypertrophy to Heart Failure in Mice, The Journal of Clinical Investigation, vol. 119, No. 5, (2009), pp. 1230-1240.

House, et al., CaMKII-Delta Isoform Regulation of Neointima Formation After Vascular injury, Arteriosler Thromb Vasc Biol., (2008), vol. 28, pp. 441-447.

Soliman, et al., Intracellular Calcium Signals Regulate Growth of Hepatic Stellate Cells Via Specific Effects on Cell Cycle Progression, Cell Calcium, vol. 45, (2009), pp. 284-292.

Zhang, et al., Inhibition of Calcium-Calmodulin-Dependent Kinase II Suppresses Cardiac Fibroblast Proliferation and Extracellular Matrix Secretion, Cardiovasc. Pharmacol., vol. 55, No. 1, (2010), pp. 96-105.

Timmins, et al., Calcium/Calmodulin-Dependent Protein Kinase II Links ER Stress With Fas and Mitochondrial Apoptosis Pathways, The Journal of Clinical Investigation, vol. 119, No. 10, pp. 2925-2941, (2009).

Vest, et al., Effective Post-insult Neuroprotection by a Novel Ca2+ /Calmodulin-Dependent Protein Kinase II (CaMKII) inhibitor, The Journal of Biological Chemistry, vol. 285, No. 27, pp. 20675-20682, (2010).

Luo, et al., Reversal of Chronic Inflammatory Pain by Acute Inhibition of Ca2+ /Calmodulin-Dependent Protein Kinase II, The Journal of Pharmacology and Experimental Therapeutics, vol. 325, No. 1, pp. 267-275, (2008).

Westra, et al., Expression and Regulation of HIF-1 alpha in Macrophages Under Inflammatory Conditions; Significant Reduction of VEGF by CaMKII Inhibitors, BMC Musculoskelatal Disorders, vol. 11, pp. 61-72, (2010).

Levy, et al., Aryl-Indolyl Maleimides as Inhibitors of CaMKIIdelta. Part 1: SAR of the Aryl Region, Bioorganic & Medicinal Chemistry Letters, vol. 18, (2008), pp. 2390-2394.

Levy, et al., Aryl-Indolyl Maleimides as Inhibitors of CaMKIIdelta. Part 2: SAR of the Amine Tether, Bioorganic & Medicinal Chemistry Letters, vol. 18, (2008), pp. 2395-2398.

Lu, et al., Aryi-Indolyl Maleimides as Inhibitors of CaMKIIdelta Part 3: Importance of the Indole Orientation, Bioorganic & Medicinal Chemistry Letters, vol. 18, (2008), pp. 2399-2403.

Todd, et al., Sulfilimines Derived from Sulfanilamide, J. Amer. Chem. Soc., (1943), vol. 65, pp. 350-354.

Pesson, et al., Antibacteriens derives des acides alkyl-8 oxo-5 dehydro-5,8 pyrido [2,3-d] pyrimidine-6 carboxyliques. II.—Derives piperazinyl-2 et (alkyl-4 piperazinyl)-2, Eur. J. Med. Chem., Chimica Therapeutica, (1974), vol. 6, pp. 591-596.

Shadbolt, et al., Pyrimidines. Part II. Nucleophilic Substitution Reactions of Ethyl 4-Chloro-2-Methylthiopyrimidine-5-Carboxylate, J. Chem. Soc., (1967), vol. 13, pp. 1172-1178.

Boschelli, et al., Synthesis and Tyrosine Kinase Inhibitory Activity of a Series of 2-Amino-8H-Pyrido[2,3-d] Pyrimidines: Identification of Potent, Selective Platelet-Derived Growth Factor Receptor Tyrosine Kinase Inhibitors, J. Med. Chem., vol. 41, pp. 4365-4377, (1998).

Olah at al., Synthetic Methods and Reactions; IV. Fluorination of Carboxylic Acids with Cyanuric Fluoride, Synthesis, 1973 pp. 487-488.

Smith, et al., Pyrimidines. V. Dehalogenation and Nuclear Reduction of Certatin Pyrimidines, J. Org. Chem., (1955), vol. 20 No. 7, pp. 829-838.

CAS AN 1975:409979.

* cited by examiner

OXO-5,8-DIHYDROPYRIDO[2,3-D]PYRIMIDINE DERIVATIVES AS CAMKII KINASE INHIBITORS FOR TREATING CARDIOVASCULAR DISEASES

This application is a Continuation of International Application No. PCT/FR2011/050019, filed Jan. 6, 2011, which claims priority of French Application No. 1050103, filed Jan. 8, 2010, both of which are incorporated herein by reference in their entireties.

The present invention relates to 5-oxo-5,8-dihydropyrido [2,3-d]pyrimidine derivatives, to their preparation and to their therapeutic use.

Calcium is a key element of intracellular signalling leading to varied responses, for example at the cardiac and cerebral level. Calcium also has an essential role as a second messenger in various intracellular processes such as apoptosis, regulation of the cell cycle, gene expression, hormonal signalling and the cellular response to oxidative stress. To induce these biological responses, calcium uses a ubiquitous intracellular receptor, calmodulin. The calcium-calmodulin complex can then bind to and activate especially the "$Ca^{2+}$/calmodulin-dependent protein kinases"(CaMKs), which are serine/threonine protein kinases.

CaMKII is a member of the family of CaMKs, of which four known isoforms (α, β, γ and δ) are distributed in various tissue types. Thus, CaMKIIα and CaMKIIβ are mainly localized in the brain and skeletal muscle, whereas CaMKIIγ and CaMKIIδ are expressed in numerous tissues and organs including the heart, the lungs and the kidneys.

Recently, the four isoforms of CaMKII (α, β, γ and δ) were crystallized with relatively unselective competitive ATP inhibitors (Rellos et al. Plosbiology 2010, 8, e1000426). As expected, the four structures are very similar on account of the very high sequence homology of the four isoforms of CaMKII, in particular as regards the ATP binding pocket. On the basis of these data, it may be considered that an inhibitor that binds to the ATP binding pocket of the δ isoform is also an inhibitor of the α, β and γ isoforms.

Many indications supporting the deleterious role of CaMKII in the development of heart pathologies have been reported in the literature:

the increase in expression and activity of CaMKIIδ has been demonstrated in experimental models of cardiac hypertrophy and in cardiac insufficiency in man (Hagemann et al., Mol. Cell. Biochem. 2001, 220:69-76; Boknik et al., Cardiovasc. Res. 2001, 51:717-728; Hempel et al., Basic Res. Cardiol. 2002; 97 Suppl. 1:196-101; Colomer et al., Mol. Endocrinol. 2003, 17:183-192; Zhang et al., Circ. Res. 2003, 92:912-919; Currie et al., FEBS Lett. 1999, 459:244-248; Hoch et al., Circ. Res. 1999, 84:713-721; Kirchhefer et al., Cardiovasc. Res. 1999, 42:254-261);

the development of cardiac hypertrophy and cardiac insufficiency has been established in transgenic mice that overexpress CaMKIIδ in the heart (Zhang et al., Circ. Res. 2003, 92:912-919; Zhang et al., J. Biol. Chem. 2002, 277:1261-1267; Maier et al., Circ. Res. 2003, 92:904-911);

the protection of mice against myocardial infarction, cardiac arrhythmia, cardiac hypertrophy and cardiac insufficiency by inhibition of CaMKII has been demonstrated by means of an inhibitor of the CaMKII activation of small molecule type (KN-93 inhibitor), a peptide inhibitor of the CaMKII pseudo-substrate (AC3-1) or by means of mice bearing a deletion of the CaMKIIδ gene (Zhang et al., Nat. Med. 2005, 11:379-380; Yang et al., Am. J. Physiol. Heart Circ. Physiol. 2006, 291:H3065-H3075; Vila-Petroff et al., Cardiovasc. Res. 2007, 73:689-98; Wu et al., Circulation 2002, 106:1288-1293; Khoo et al., Circulation 2006, 114:1352-1359; Backs et al., Proc. Natl Acad. Sci. 2009, 106:2342-2347, Ling et al., J. Clin. Invest. 2009, 119:1230-40). These indications confirm the potential use of CaMKII inhibitors for preventing and/or treating myocardial infarction, cardiac arrhythmia, cardiac hypertrophy and cardiac insufficiency.

It has moreover been demonstrated that the extinction of CaMKIIδ leads to an 80% reduction of formation of neointima in a model of carotid cuff lesion in rats (House et al., Arterioscler. Thromb. Vasc. Biol. 2008, 28:441-7), indicating that CaMKII inhibitors might also be used for treating restenosis.

What is more, CaMKII contributes towards the proliferation of hepatic stellate cells (Soliman et al., Cell Calcium 2009, 45, 284-292) and also towards the proliferation of cardiac fibroblasts and the production of extracellular matrix by these cells (Zhang et al., J. Cardiovasc. Pharmacol. 2010, 55:96-105).

These indications make CaMKII a new therapeutic target in the treatment of fibrotic diseases including hepatic fibrosis, cardiac fibrosis, pancreatic fibrosis, renal fibrosis, pulmonary fibrosis, cutaneous fibrosis, intestinal fibrosis and ocular fibrosis.

It has also been recently suggested that CaMKII is involved in the apoptosis of endothelial cells induced by stress of the endoplasmic reticulum or of neuronal cells induced with 6-hydroxydopamine, which may be important events, respectively, in atherosclerosis and Parkinson's disease (Timmins et al., J. Clin. Invest. 2009, 119: 2925-2941). Moreover, in a model of acute renal insufficiency induced by a systemic stress of the endoplasmic reticulum in mice, a reduction in the apoptosis of the tubular epithelial cells and preservation of the renal function were observed in the case of CaMKIIγ KO mice (Timmins et al., J. Clin. Invest. 2009, 119:2925-2941), suggesting a possible use of a CaMKII inhibitor in the treatment of renal pathologies, in particular acute renal insufficiency.

Moreover, a neuroprotective effect by a peptide inhibitor of the "autonomous" activity of CaMKII, in this instance CN21, has recently been reported (Vest et al. J. Biol. Chem. 2010, 285: 20675-20682). This type of CaMKII inhibition may offer a new therapeutic approach for neuroprotection after a stroke.

Furthermore, in a murine model of pain of inflammatory origin, it has been shown that inhibition of the activity of CaMKII with trifluoperazine allows dose-dependent reversion of allodynia of mechanical origin and hyperalgia of thermal origin (Luo et al. J. Pharm. Exp. Ther. 2008 325: 267-275). These results suggest that CaMKII inhibitors might make it possible to treat chronic pain.

It has also been reported that CaMKII inhibitors, in particular SMP-114, enable inhibition of the expression of HIF-1α and the significant inhibition of VEGF production in macrophages (Westra et al. BMC Musculoskeletal Disorders 2010, 11:61-72). In this case, the inhibitory activity of CaMKII might be partly responsible for the anti-arthritic effect of SMP-114, and, more generally, it might be thought that a CaMKII inhibitor might make it possible to treat rheumatoid arthritis.

A certain number of competitive CaMKII inhibitors are well known in the literature, for instance KN-93 and the peptide AIP (autocamtide-2-related inhibitory peptide). Isoxazole derivatives have also been described as CaMKII inhibitors (EP 1 815 867) and, more recently, peptides such as CN21 have been disclosed as inhibitors of the autonomous activity of CaMKII (WO 2009/042 906).

Other competitive inhibitors of aryl-indolyl maleimide type (Levy et al. Bioorg. Med. Chem. Letters 2008, 18:2390-2394, 2395-2398 and 2399-2403) have been described in the literature. Non-competitive inhibitors bearing a pyrimidine unit are also known (Mavunkel et al. Bioorg. Med. Chem. Letters 2008, 18:2404-2408).

One subject of the present invention is novel compounds that are CaMKII inhibitors, corresponding to formula (I):

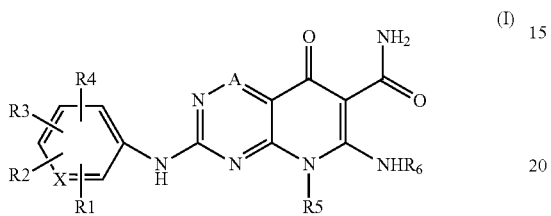

in which:
A represents CH or C(alkyl);
X represents CH, C(alkyl) or N;
R1, R2, R3 and R4, which may be identical or different, represent, independently of each other:
  a hydrogen atom;
  a linear, branched or cyclic alkyl, optionally substituted with one or more of the following:
    halogen atoms;
    —$OR_9$;
    —$NR_9R'_9$,
    —CN;
    —$C(O)OR_9$;
    —$C(O)NR_9R_9$;
    —$S(O)_pR_{10}$;
    —$S(O)_2NR_9R'_9$;
    in which $R_9$, $R'_9$, $R_{10}$ and p are as defined below
  a group —$S(O)_pR_{10}$ in which p and $R_{10}$ are as defined below;
  a group —$OR_{10}$ in which $R_{10}$ is as defined below;
  a halogen atom;
  a group —$N(R_{11})C(O)R_{12}$, in which
    (i) $R_{11}$ and $R_{12}$ represent, independently of each other, a hydrogen atom or a linear, branched or cyclic alkyl, optionally substituted with one or more substituents chosen from halogen atoms, groups —$OR_9$ and groups —$NR_9R'_9$, or
    (ii) $R_{11}$ and $R_{12}$ form, together with the atoms to which they are attached, a heterocycloalkyl, so as to form a lactam;
  a group —$N(R_{14})$—$CH_2$—$C(O)NR_{15}R_9$, in which $R_{14}$ and $R_{15}$ form, together with the atoms to which they are attached, a heterocycloalkyl, so as to form a piperazinone and in which $R_9$ is as defined below;
  a group —$C(O)NR_{16}R_{17}$ with $R_{16}$ and $R_{17}$ forming, together with the nitrogen atom to which they are attached, a heterocycloalkyl
  a group -T-U, in which:
    T represents:
      a single bond,
      a linear or branched alkylene group,
      a group —C(O)—,
      a group —$S(O)_p$— in which p is as defined below, or
      a group —O—$(CH_2)_n$— in which n is as defined below,
    with U representing a heterocycle comprising one or more heteroatoms chosen from N, O and $S(O)_p$, in which p is as defined below, the said heterocycle being saturated, unsaturated or aromatic, optionally mono- or di- or polysubstituted with one, two or several substituents chosen from:
      groups —$OR_7$, in which $R_7$ is as defined below,
      halogen atoms,
      groups —$C(O)R_7$ in which $R_7$ is as defined below,
      linear, branched or cyclic alkyls, optionally substituted with one or more substituents chosen from halogen atoms, groups —$OR_{10}$, groups —$NR_9R'_9$ and the group —CN, in which $R_9$, $R'_9$ and $R_{10}$ are as defined below; and
      saturated, unsaturated or aromatic heterocycles, optionally substituted with one or more substituents chosen from halogen atoms, groups —$OR_9$, groups —$NR_9R'_9$ and alkyl groups, the said alkyl groups being optionally substituted with one or more halogen atoms;
    it being understood that when U is a heterocycloalkyl group comprising at least one nitrogen atom, the said substituent is advantageously chosen from:
      groups —$C(O)R_7$ in which $R_7$ is as defined below; and
      linear, branched or cyclic alkyls, optionally substituted with one or more substituents chosen from halogen atoms, groups —$OR_{10}$, groups —$NR_9R'_9$ and the group —CN, in which $R_9$, $R'_9$ and $R_{10}$ are as defined below;
    and the said substituent being advantageously borne by the said nitrogen atom, or
    T represents:
      a group —C(O)—;
      a group —$S(O)_2$—; or
      a group —O—(C2-C3)alkylene-;
    with U representing a group —$NR_9R'_9$ in which $R_9$ and $R'_9$ are as defined below; or
    T represents:
      a group —C(O)—; or
      a group —O—(C2-C3)alkylene-;
    when U represents a group —$OR_9$, in which $R_9$ is as defined below; or
    T represents:
      a linear or branched alkylene group; or
      a group —O—(C2-C3)alkylene;
    with U representing a group —$NR_8R_9$ in which $R_9$ and $R_8$ are as defined below;
  or alternatively two adjacent groups chosen from R1, R2, R3 and R4 are linked and form, with the two carbons that bear them, a saturated, unsaturated or aromatic heterocycle, optionally substituted with one or more linear, branched or cyclic alkyl groups, the said alkyl groups being optionally substituted with one or more substituents chosen from halogen atoms, groups —$OR_{10}$, and groups —$NR_9R'_9$, in which $R_9$, $R'_9$ and $R_{10}$ are as defined below,
  the said heterocycle being fused with the aromatic ring,
  $R_5$ represents:
    a linear or branched alkyl, optionally substituted with one or more substituents chosen from halogen atoms, groups —$OR_9$, groups —$NR_9R'_9$, the group —CN, groups —$C(O)NR_9R_9R_9$', groups —$S(O)_pR_{10}$ and cycloalkyl groups optionally substituted with a group —$NR_9R'_9$, in which $R_9$, $R'_9$, $R_{10}$ and p are as defined below, a cycloalkyl group, optionally substituted with a group —NR$_9$R'$_9$, in which R$_9$ and R'$_9$ are as defined below, an alkoxy group —OR$_9$, in which R$_9$ is as defined below, an aryl optionally substituted with one or more substituents chosen from groups (C1-C3)alkyl, halogen atoms and groups —O—(C1-C3)alkyl, or a group —(CH$_2$)$_t$—R$_{13}$, in which R$_{13}$ and t are as defined below, R$_6$ represents a hydrogen atom or a linear, branched or cyclic alkyl, and in which:

R$_7$ represents a hydrogen atom or a linear, branched or cyclic alkyl, optionally substituted with one or more of the following substituents chosen from halogen atoms, groups —OR$_9$ and groups —NR$_9$R'$_9$ with R$_9$ and R'$_9$ as defined above;

R$_8$ represents a heteroaryl group, advantageously a pyridine;

R$_9$ and R'$_9$ represent, independently of each other, a hydrogen atom or a linear, branched or cyclic alkyl;

R$_{10}$ represents a hydrogen atom or a linear, branched or cyclic alkyl optionally substituted with one or more halogen atoms, R$_{13}$ represents a heteroaryl or a heterocycloalkyl optionally substituted with one or more substituents chosen from linear, branched or cyclic alkyls, it being understood that when the said heterocycloalkyl comprises at least one nitrogen atom, this atom may optionally bear the said substituent, t represents 1 or 2, n represents 0, 1, 2 or 3, and p represents 0, 1 or 2, in the form of acid, base or addition salt with an acid or a base, and also in the form of hydrate or solvate.

The compounds of formula (I) may comprise one or more asymmetric carbon atoms. They may thus exist in the form of enantiomers or diastereoisomers. These enantiomers and diastereoisomers, and also mixtures thereof, including racemic mixtures, form part of the invention.

The compounds of formula (I) may exist in the form of bases or acid-addition salts. Such addition salts form part of the invention.

These salts may be prepared with pharmaceutically acceptable acids, but the salts of other acids that are useful, for example, for purifying or isolating the compounds of formula (I) also form part of the invention.

The compounds of formula (I) may also exist in the form of hydrates or solvates, i.e. in the form of associations or combinations with one or more water molecules or with a solvent. Such hydrates and solvates also form part of the invention.

In the context of the present invention, and unless otherwise mentioned in the text, the following definitions apply:

a halogen atom: a fluorine, chlorine, bromine or iodine atom;

an alkyl group: a linear or branched, saturated aliphatic group, which may comprise 1, 2, 3, 4, 5 or 6 carbon atoms (abbreviated as —(C1-C6)alkyl). By way of example, the following groups may be mentioned: (i) as group —C1alkyl, the methyl group, (ii) as group —C2alkyl, the ethyl group, (iii) as group —C3alkyl, the propyl or isopropyl group, (iv) as group —C4alkyl, the butyl, isobutyl or tert-butyl group, (v) as group —C5alkyl, the pentyl or isopentyl group;

an alkylene group: a linear or branched, saturated, divalent alkyl group as defined previously, which may comprise 1, 2, 3, 4 or 5 carbon atoms (abbreviated as —(C1-C5) alkylene-). Examples that may be mentioned include the methylene (or —CH2—), ethylene (or —CH2-CH2-) or propylene (—CH2-CH2-CH2- or —C(CH3)$_2$-) radicals;

a cycloalkyl group: a cyclic alkyl group that may comprise 3, 4, 5 or 6 carbon atoms, also abbreviated as —(C3-C6) cycloalkyl and in which all the carbon atoms are engaged in the ring. Examples that may be mentioned include cyclopropyl, cyclobutyl, cyclopentyl and cyclohexyl groups;

an alkoxy group: a radical —O-alkyl in which the alkyl group is as defined previously. Examples that may be mentioned include the groups —O—(C1-C5)alkyl or —(C1-C5)alkoxy, and in particular, (i) as group —O—C1alkyl, the group —Omethyl, (ii) as group —O—C2alkyl, the group —Oethyl, (iii) as group —O—C3alkyl, the group —Opropyl or —Oisopropyl, (iv) as group —O—C4alkyl, the group —Obutyl, —Oisobutyl or —Otert-butyl, (v) as group —O—C5alkyl, the group —Opentyl, —Oisopentyl or —Oneopentyl;

an aryl group: a monocyclic or bicyclic aromatic group comprising between 5 and 10 carbon atoms and advantageously between 5 and 6 carbon atoms. Examples of aryl groups that may be mentioned include the phenyl group and the naphthyl group;

a heterocyclyl group: a 3- to 10-membered monocyclic or bicyclic group comprising one or more heteroatoms chosen from O, N and S.

The said heterocycle may be saturated or partially unsaturated and may comprise one or more double bonds. It is then referred to as a heterocycloalkyl group. Examples of non-aromatic or heterocycloalkyl heterocycles that may be mentioned include lactams, piperazinone, epoxyethyl, oxiranyl, aziridinyl, tetrahydrofuryl, dioxolanyl, pyrrolidinyl, piperidyl, pyrazolidinyl, imidazolidinyl, tetrahydrothiophenyl, dithiolanyl, thiazolidinyl, tetrahydropyranyl, dioxanyl, morpholinyl, piperidyl, piperazinyl, tetrahydrothiopyranyl, dithianyl, thiomorpholinyl, dihydrofuryl, 2-imidazolinyl, 2,3-pyrrolinyl, pyrazolinyl, dihydrothiophenyl, dihydropyranyl, pyranyl, tetrahydropyridyl, dihydropyridyl, tetrahydropyrimidinyl and dihydrothiopyranyl, and corresponding groups derived from fusion with a phenyl nucleus, and more particularly morpholinyl, dioxalanyl, benzothiazolidinyl, pyrrolidinyl and benzopyrrolidinyl rings.

Advantageously, a heterocycloalkyl is an optionally bridged cyclic alkyl group comprising 4, 5, 6 or 7 carbon atoms and comprising 1, 2 or 3 heteroatoms chosen from oxygen, nitrogen and sulfur, for instance piperidyl, piperazinyl, pyrrolidinyl, hexamethyleneimino, morpholinyl and 1,1-dioxydotetrahydrothienyl groups.

The said heterocycle may also be aromatic and 5- to 10-membered, and may then represent a heteroaryl group.

Heteroaryls that may especially be mentioned include the following representative groups: benzimidazolyl, benzothiazolyl, furyl, imidazolyl, indolyl, indolizinyl, isoxazolyl, isoquinolinyl, isothiazolyl, oxadiazolyl, pyrazinyl, pyridazinyl, pyrazolyl, pyridyl, pyrimidinyl, pyrrolyl, quinazolinyl, quinolinyl, 1,3,4-thiadiazolyl, thiazolyl, thienyl and triazolyl.

Advantageously, a heteroaryl group is a cyclic aromatic group comprising 2, 3, 4 or 5 carbon atoms and comprising 1, 2 or 3 heteroatoms, which may be chosen from a nitrogen atom, an oxygen atom and a sulfur atom, independently of each other, so as to be identical or different, when there are two of them, or independently of each other, so as to be identical or different, when there are three of them. Examples that may especially be mentioned include pyridyl, pyrrolyl and furyl groups.

When the heterocycle is substituted, the substituent(s) may be on one or more carbon atoms included in the said heterocycle and/or, where appropriate, on the heteroatom(s) of the said heterocycle. When the heterocycle comprises several substituents, they may be borne on different atoms or, where appropriate, on the same atom;

a protecting group Pg: a group that makes it possible, firstly, to protect a reactive function such as a hydroxyl or an amine during a synthesis, and, secondly, to regenerate the intact reactive function at the end of the synthesis. Examples of protecting groups and of protection and deprotection methods are given in "Protective Groups in Organic Synthesis", Greene et al., $2^{nd}$ Edition (John Wiley & Sons, Inc., New York);

a leaving group: a group that can be readily cleaved from a molecule by breaking a heterolytic bond, with loss of an electron pair. This group may thus be readily replaced with another group during a substitution reaction, for example. Such leaving groups are, for example, halogens or an activated hydroxyl group such as a methanesulfonate, benzenesulfonate, p-toluenesulfonate, triflate, acetate, etc. Examples of leaving groups and references for preparing them are given in "Advances in Organic Chemistry", J. March, $3^{rd}$ Edition, Wiley Interscience, pp. 310-316.

Among the compounds of formula (I) that are subjects of the invention, a first group of compounds is formed by the compounds for which:

A represents CH or $C(CH_3)$, advantageously A represents CH;

and/or

X represents CH or N, advantageously X represents CH;

and/or $R_1$, $R_2$, $R_3$ and $R_4$, which may be identical or different, represent, independently of each other:
- a hydrogen atom;
- a linear, branched or cyclic alkyl, optionally substituted with one or more of the following:
  - halogen atoms;
  - $-OR_9$;
  - $-NR_9R'_9$,
  - $-CN$;
  - $-C(O)OR_9$,
  - $-C(O)NR_9R_{9'}$,
  - $-S(O)_pR_{10}$,
  - $-S(O)_2NR_9R'_9$;
- a group $-S(O)_pR_{10}$;
- a group $-OR_{10}$;
- a halogen atom;
- a group $-N(R_{11})C(O)R_{12}$,
- a group $-N(R_{14})-CH_2-C(O)NR_{15}R_9$, in which $R_{14}$ and $R_{15}$ form, together with the atoms to which they are attached, a heterocycloalkyl, so as to form a piperazinone and in which $R_9$ is as defined below;
- a group $-C(O)NR_{16}R_{17}$ with $R_{16}$ and $R_{17}$ forming, together with the nitrogen atom to which they are attached, a heterocycloalkyl, so as to form advantageously a piperidyl or a pyrrolidinyl,
- a group -T-U, in which:
  T represents:
  - a single bond,
  - a linear or branched alkylene group;
  - a group $-C(O)-$,
  - a group $-S(O)_p-$ in which p is as defined below, or
  - a group $-O-(CH_2)_n-$ in which n is as defined below, with U representing a heterocycle comprising one or more heteroatoms chosen from N, O and $S(O)p$, in which p is as defined below, the said heterocycle being saturated, unsaturated or aromatic, optionally mono- or di- or polysubstituted with one, two or several substituents chosen from:
  - groups $-OR_7$,
  - halogen atoms,
  - groups $-C(O)R_7$,
  - linear, branched or cyclic alkyls, optionally substituted with one or more substituents chosen from halogen atoms, groups $-OR_{10}$, groups $-NR_9R'_9$ and the group $-CN$;
  - saturated, unsaturated or aromatic heterocycles, optionally substituted with one or more substituents chosen from halogen atoms, groups $-OR_9$, groups $-NR_9R'_9$ and alkyl groups, the said alkyl groups being optionally substituted with one or more halogen atoms;

it being understood that when U is a heterocycloalkyl group comprising at least one nitrogen atom, the said substituent is advantageously chosen from:
  - a group $-C(O)R_7$; and
  - linear, branched or cyclic alkyls, optionally substituted with one or more substituents chosen from halogen atoms, groups $-OR_{18}$, groups $-NR_9R'_9$ and the group $-CN$;

and the said substituent being advantageously borne by the said nitrogen atom, or T represents:
  - a group $-C(O)-$;
  - a group $-S(O)_2-$; or
  - a group $-O-(C2-C3)$alkylene-;

with U representing a group $-NR_9R'_9$, or

T represents:
  - a group $-C(O)-$; or
  - a group $-O-(C2-C3)$alkylene-;

with U representing a group $-OR_9$;

or

T represents:
  - a linear or branched alkylene group; or
  - a group $-O-(C2-C3)$alkylene-;

with U representing a group $-NR_8R_9$;

- or alternatively two adjacent groups chosen from R1, R2, R3 and R4 are linked and form, with the two carbons that bear them, a saturated, unsaturated or aromatic heterocycle, optionally substituted with one or more linear, branched or cyclic alkyl groups, the said alkyl groups being optionally substituted with one or more substituents chosen from halogen atoms, groups $-OR_{10}$, and groups $-NR_9R'_9$, and/or $R_5$ represents:
- a linear or branched alkyl, optionally substituted with one or more substituents chosen from halogen atoms, groups $-OR_9$, groups $-NR_9R'_9$, the group $-CN$, groups $-C(O)NR_9R_{9'}$, groups $-S(O)_pR_{10}$ and cycloalkyl groups optionally substituted with a group $-NR_9R'_9$,
- a cycloalkyl group, optionally substituted with a group $-NR_9R'_9$,
- an alkoxy group $-OR_9$,
- an aryl optionally substituted with one or more substituents chosen from groups (C1-C3)alkyl, halogen atoms and groups $-O-(C1-C3)$alkyl, or
- a group $-(CH_2)_t-R_{13}$, advantageously $R_5$ represents (i) a linear or branched alkyl, optionally substituted with one or more substituents chosen from halogen atoms, groups —$OR_9$, groups —$NR_9R'_9$ and cycloalkyl groups, (ii) a cycloalkyl group (iii), an aryl optionally substituted with one or more substituents chosen from groups (C1-C3)alkyl, halogen atoms and groups —O—(C1-C3)alkyl, or (iv) a group —(CH$_2$)$_t$—$R_{13}$, and/or $R_6$ represents a hydrogen atom or a linear, branched or cyclic alkyl, advantageously $R_6$ represents a hydrogen atom, and/or $R_7$ represents a hydrogen atom or a linear, branched or cyclic alkyl, optionally substituted with one or more substituents chosen from halogen atoms, groups —$OR_9$ and groups —$NR_9R'_9$;

and/or $R_8$ represents a heteroaryl group, advantageously a pyridine;

and/or $R_9$ and $R'_9$ represent, independently of each other, a hydrogen atom or a linear, branched or cyclic alkyl;

and/or $R_{10}$ represents a hydrogen atom or a linear, branched or cyclic alkyl optionally substituted with one or more halogen atoms, and/or $R_{11}$ and $R_{12}$ represent, independently of each other, a hydrogen atom or a linear, branched or cyclic alkyl, optionally substituted with one or more substituents chosen from halogen atoms, groups —$OR_9$ and groups —$NR_9R'_9$, or $R_{11}$ and $R_{12}$ form, together with the atoms to which they are attached, a heterocycloalkyl, so as to form a lactam;

and/or $R_{13}$ represents a heteroaryl or a heterocycloalkyl optionally substituted with one or more substituents chosen from linear, branched or cyclic alkyls, it being understood that when the said heterocycloalkyl comprises at least one nitrogen atom, this atom may optionally bear the said substituent, advantageously $R_{13}$ is a tetrahydrofuryl, and/or t represents 1 or 2, and/or n represents 0, 1, 2 or 3, and/or p represents 0, 1 or 2 and/or in the form of acid, base or addition salt with an acid or a base, and also in the form of hydrate or solvate.

Among the compounds of formula (I) that are subjects of the invention, a second group of compounds is formed by the compounds for which:

A represents CH,

X represents CH, C(alkyl) or N, advantageously X represents CH, $R_1$, $R_2$, $R_3$ and $R_4$, which may be identical or different, represent, independently of each other:

a hydrogen atom, a linear, branched or cyclic alkyl, optionally substituted with one or more of the following halogen atoms, a group —$OR_9$ or —$NR_9R'_9$, in which $R_9$ and $R'_9$ represent, independently of each other, a hydrogen atom or a linear, branched or cyclic alkyl, a group —S(O)$_p$$R_{10}$ or a group —$OR_{10}$, in which $R_{10}$ represents a hydrogen atom or a linear, branched or cyclic alkyl optionally substituted with one or more halogen atoms, and p represents 0, 1 or 2, a halogen atom, a group —N($R_{11}$)C(O)$R_{12}$, in which $R_{11}$ and $R_{12}$ represent, independently of each other, a hydrogen atom or a linear, branched or cyclic alkyl or $R_{11}$ and $R_{12}$ form, together with the atoms to which they are attached, a heterocycloalkyl, so as to form a lactam;

a group -T-U, in which

T represents:

a single bond, a linear or branched alkylene group, a group —C(O)—, a group —S(O)$_p$, in which p represents 0, 1 or 2, a group —O—(CH$_2$)$_n$— in which n represents 0, 1, 2 or 3, and U represents a heterocycle comprising one or more heteroatoms chosen from N, O and S(O)$_p$ in which p represents 0, 1 or 2, the said heterocycle being of the formula:

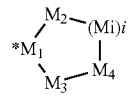

in which

* represents the position of attachment of U to T;

$M_1$ represents a C or N atom;

$M_2$ and $M_3$, which may be identical or different, represent a C, N or O atom or S(O)$_p$ in which p=0, 1 or 2;

$M_4$ represents a C, C(=O), N, O or S(O)$_p$ atom in which p=0, 1 or 2;

each of the $M_i$, which may be identical or different, represent a C, C(=O), N, O or S(O)p atom in which p=0, 1 or 2;

i=0, 1, 2 or 3;

it being understood that each of the $M_1$, $M_2$, $M_3$, $M_4$ or $M_i$ may be optionally substituted if a valency is available and/or the adjacent $M_1$, $M_2$, $M_3$, $M_4$ or $M_i$ may be attached via a double bond, where appropriate;

the said heterocycle U being saturated, unsaturated or aromatic, optionally mono- or di- or polysubstituted with one, two or several substituents chosen from:

groups —$OR_7$, in which $R_7$ represents a hydrogen atom or a linear, branched or cyclic alkyl, halogen atoms, groups —$COR_7$ in which $R_7$ represents a hydrogen atom or a linear, branched or cyclic alkyl, linear, branched or cyclic alkyls, advantageously a methyl, an ethyl or a cyclopropyl, optionally substituted with one or more halogen atoms, saturated, unsaturated or aromatic heterocycles, especially a heterocycle comprising an N, advantageously a morpholinyl, a pyrrolidinyl or a piperidyl, optionally substituted with one or more groups chosen from halogen atoms and alkyl groups optionally substituted with one or more halogen atoms;

or alternatively two adjacent groups from among $R_1$, $R_2$, $R_3$ and $R_4$ are linked and form, with the two carbons that bear them, a saturated, unsaturated or aromatic heterocycle, optionally substituted with one or more linear, branched or cyclic alkyl groups, the said alkyl groups being optionally substituted with at least one group chosen from groups —$NR_9R'_9$, in which $R_9$ and $R'_9$ represent, independently of each other, a hydrogen atom or an alkyl group, the said heterocycle being fused with the aromatic ring, $R_5$ represents (i) a linear or branched alkyl, optionally substituted with one or more substituents chosen from halogen atoms, cycloalkyl groups, groups —NR$_9$R'$_9$, in which $R_9$ and R'$_9$ represent, independently of each other, a hydrogen atom or an alkyl group and groups —OR$_9$, in which $R_9$ represents a hydrogen atom or an alkyl group, (ii) an aryl optionally substituted with one or more substituents chosen from groups (C1-C3)alkyl, halogen atoms and groups —O—(C1-C3)alkyl, and $R_6$ represents a hydrogen atom or a linear, branched or cyclic alkyl, in the form of acid, base or addition salt with an acid or a base, and also in the form of hydrate or solvate.

Among the compounds of formula (I) that are subjects of the invention, another group of compounds is formed by the compounds corresponding to formula (I') below:

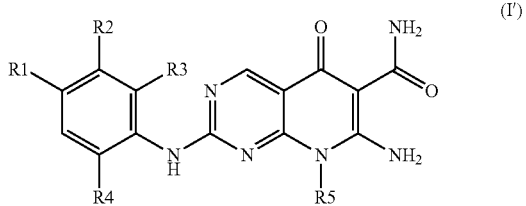

(I')

in which:

$R_1$ represents:
a hydrogen atom,
a linear, branched or cyclic alkyl, optionally substituted with one or more of the following substituents chosen from halogen atoms, groups —NR$_9$R'$_9$, in which $R_9$ and R'$_9$ represent, independently of each other, a hydrogen atom or an alkyl group, advantageously a methyl,
—OR$_{10}$, in which $R_{10}$ represents a hydrogen atom or a linear, branched or cyclic alkyl optionally substituted with one or more halogen atoms,
a halogen atom,
a group -T-U, in which
T represents:
a single bond,
an alkylene group, advantageously a group —(CH$_2$)$_{1-3}$—,
a group —C(O)—,
a group —O—(CH$_2$)$_n$ in which n represents 0, 1, 2 or 3,
and U represents a saturated, unsaturated or aromatic heterocycle, optionally mono- or disubstituted with a substituent, advantageously chosen from:
halogen atoms,
groups —COR$_7$ in which R$_7$ represents a hydrogen atom or a linear, branched or cyclic alkyl, advantageously a methyl,
linear, branched or cyclic alkyls, advantageously a methyl, an ethyl or a cyclopropyl, the said alkyl being optionally substituted with one or more halogens,
heterocycles, advantageously saturated, comprising a nitrogen atom, advantageously a morpholinyl, a pyrrolidinyl or a piperidyl, the said heterocycle being optionally substituted with one or more groups chosen from halogen atoms;

R2, R3 and R4, which may be identical or different, independently represent:
a hydrogen atom,
a linear, branched or cyclic alkyl, optionally substituted with one or more of the following substituents chosen from halogen atoms and groups —NR$_9$R'$_9$, in which $R_9$ and R'$_9$ represent, independently of each other, a hydrogen atom or an alkyl, advantageously a methyl,
a group —OR$_{10}$, in which R$_{10}$ represents a hydrogen atom or an alkyl optionally substituted with one or more halogen atoms,
a halogen,
a group -T-U with T representing a bond and U a morpholinyl, or
$R_1$ and $R_2$ are linked and form, with the two carbon atoms that bear them, a heterocycle chosen from a piperidine, a thiazole, a tetrahydrofuran and a dioxane, the said heterocycle being optionally substituted with a linear, branched or cyclic alkyl optionally substituted with —NR$_9$R'$_9$, in which R$_9$ and R'$_9$ represent, independently of each other, a hydrogen atom or a methyl, the said heterocycle being fused with the aromatic ring, R5 represents (i) a linear or branched alkyl comprising from 1 to 5 carbon atoms, advantageously an ethyl, optionally substituted with one or more substituents chosen from halogen atoms advantageously a fluorine atom or a group —OH, (ii) an aryl optionally substituted with one or more substituents chosen from groups (C1-C3)alkyl, advantageously a methyl group, halogen atoms, advantageously a fluorine atom and groups —O—(C1-C3)alkyl advantageously a group methoxy, in the form of acid, base or addition salt with an acid or a base, and also in the form of hydrate or solvate.

Among the compounds of formula (I) or (I') above, mention may be made of the compounds for which:

A represents CH; and/or

X represents CH; and/or $R_1$, $R_2$, $R_3$ and $R_4$ do not all represent a hydrogen atom; and/or $R_1$ is other than a hydrogen atom; and/or $R_1$ is chosen from:

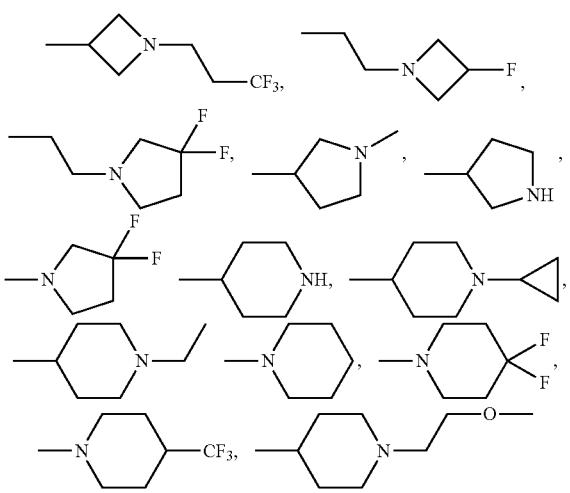

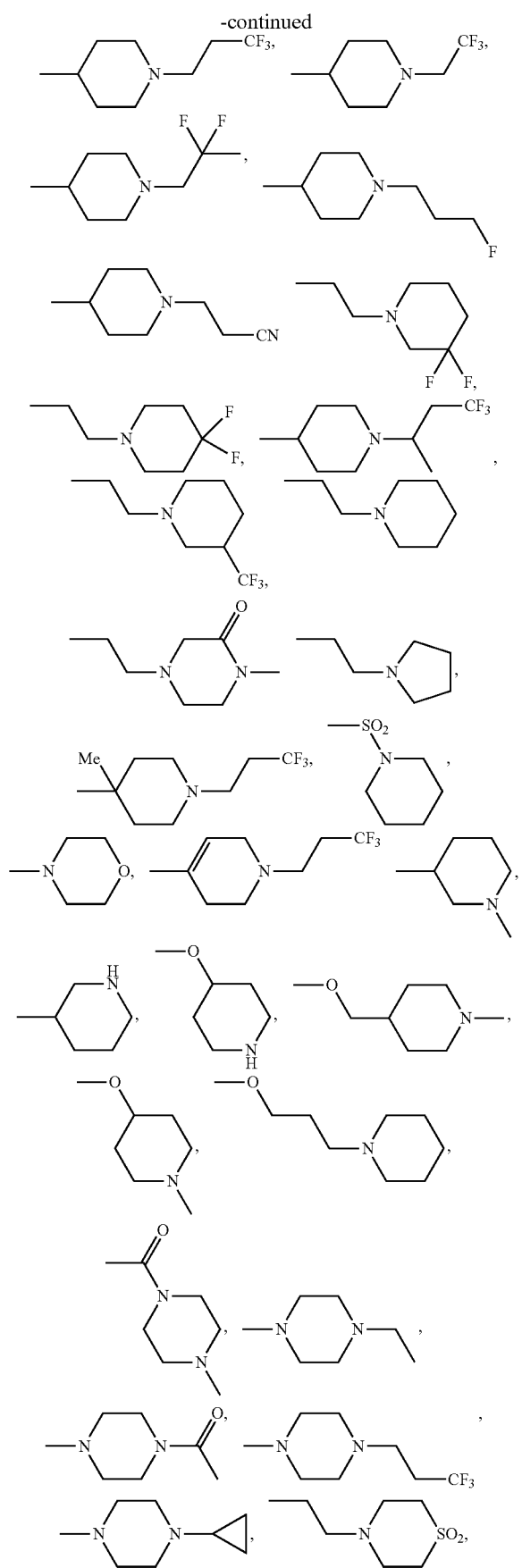

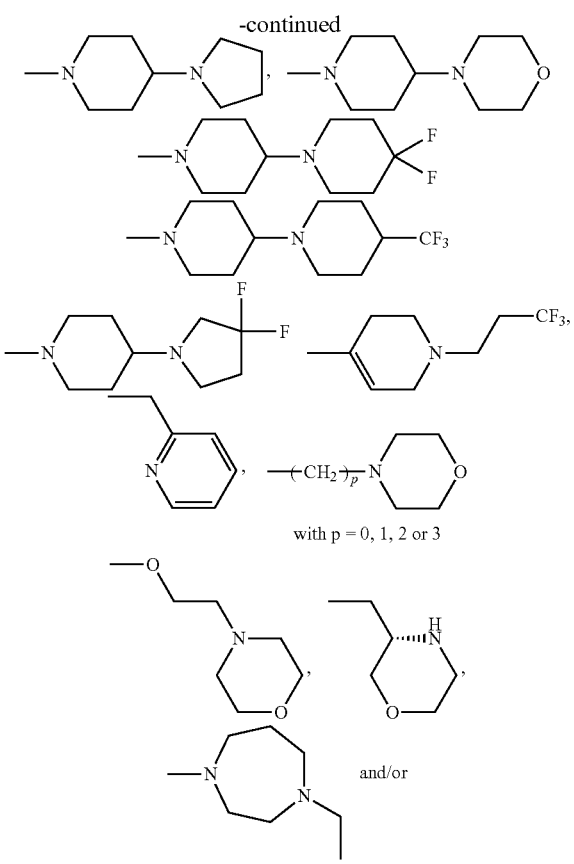

with p = 0, 1, 2 or 3

R5 represents (i) a linear or branched alkyl advantageously an ethyl, (ii) an aryl optionally substituted with one or more substituents chosen from groups (C1-C3)alkyl, advantageously a methyl group, halogen atoms, advantageously a fluorine atom; and/or U represents a saturated, unsaturated or aromatic heterocycle, optionally mono- or disubstituted, comprising at least one nitrogen atom and/or one oxygen atom, and/or U represents a saturated heterocycle comprising at least one nitrogen atom; and/or U represents a heterocycle chosen from:
  an azetidinyl, advantageously an azetidin-1-yl or an azetidin-3-yl;
  a pyrrolidinyl, advantageously a pyrrolidin-1-yl or a pyrrolidin-3-yl;
  an oxopyrrolidinyl, advantageously a 2-oxopyrrolidin-1-yl;
  a piperidyl, advantageously a piperid-1-yl, a piperid-2-yl or a piperid-4-yl, particularly advantageously a piperid-1-yl or a piperid-4-yl;
  a 1,2,3,6-tetrahydropyridyl, advantageously a 1,2,3,6-tetrahydropyrid-4-yl;
  a pyridyl, advantageously a pyrid-2-yl;
  a piperazinyl, advantageously a piperazin-1-yl;
  a diazepanyl, advantageously a diazepan-1-yl;
  a morpholinyl, advantageously a morpholin-4-yl or a morpholin-3-yl, especially a 4-(R)-1-morpholin-3-yl, particularly advantageously a morpholin-4-yl;
  a 1,1-dioxo-1lambda6-thiomorpholin-4-yl.

Among the compounds of formula (I) that are subjects of the invention, mention may be made especially of the following compounds in the order of the compounds of the table below:

7-Amino-8-ethyl-2-(4-hydroxyphenylamino)-5-oxo-5,8-dihydropyrido[2,3-d]pyrimidine-6-carboxamide;

7-Amino-2-(benzothiazol-6-ylamino)-8-ethyl-5-oxo-5,8-dihydropyrido[2,3-d]pyrimidine-6-carboxamide;

7-Amino-2-[4-(cyclopropanecarbonylmethylamino)phenylamino]-8-ethyl-5-oxo-5,8-dihydropyrido[2,3-d]pyrimidine-6-carboxamide;

7-Amino-8-ethyl-2-[4-(4-methylpiperazine-1-carbonyl)phenylamino]-5-oxo-5,8-dihydropyrido[2,3-d]pyrimidine-6-carboxamide;

7-Amino-2-(4-cyclopentyloxyphenylamino)-8-ethyl-5-oxo-5,8-dihydropyrido[2,3-d]pyrimidine-6-carboxamide;

7-Amino-8-ethyl-2-[4-(4-ethylpiperazin-1-yl)phenylamino]-5-oxo-5,8-dihydropyrido[2,3-d]pyrimidine-6-carboxamide;

7-Amino-8-ethyl-5-oxo-2-[4-(4-pyrrolidin-1-ylpiperid-1-yl)phenylamino]-5,8-dihydropyrido[2,3-d]pyrimidine-6-carboxamide;

7-Amino-8-ethyl-5-oxo-2-[4-(4-pyrrolidin-1-ylpiperid-1-yl)phenylamino]-5,8-dihydropyrido[2,3-d]pyrimidine-6-carboxamide;

7-Amino-8-ethyl-5-oxo-2-[4-(4-pyrrolidin-1-ylpiperid-1-yl)phenylamino]-5,8-dihydropyrido[2,3-d]pyrimidine-6-carboxamide;

7-Amino-8-cyclopentyl-2-(4-morpholin-4-ylphenylamino)-5-oxo-5,8-dihydropyrido[2,3-d]pyrimidine-6-carboxamide;

7-Amino-8-ethyl-5-oxo-2-[4-(piperidine-1-sulfonyl)phenylamino]-5,8-dihydropyrido[2,3-d]pyrimidine-6-is carboxamide;

2-[4-(4-Acetylpiperazin-1-yl)phenylamino]-7-amino-8-ethyl-5-oxo-5,8-dihydropyrido[2,3-d]pyrimidine-6-carboxamide;

7-Amino-8-ethyl-2-(4-morpholin-4-ylbenzylamino)-5-oxo-5,8-dihydropyrido[2,3-d]pyrimidine-6-carboxamide;

7-Amino-8-ethyl-5-oxo-2-(quinolin-3-ylamino)-5,8-dihydropyrido[2,3-d]pyrimidine-6-carboxylamide;

7-Amino-8-ethyl-5-oxo-2-[4-(3-piperid-1-ylpropoxy)phenylamino]-5,8-dihydropyrido[2,3-d]pyrimidine-6-carboxamide;

7-Amino-8-ethyl-5-oxo-2-(3, 4,5,6-tetrahydro-2H-[1,2']bipyridyl-5'-ylamino)-5,8-dihydropyrido[2,3-d]pyrimidine-6-carboxamide;

7-Amino-8-ethyl-5-oxo-2-[4-(2-oxopyrrolidin-1-yl)phenylamino]-5,8-dihydropyrido[2,3-d]pyrimidine-6-carboxamide;

7-Amino-8-ethyl-5-oxo-2-(quinolin-6-ylamino)-5,8-dihydropyrido[2,3-d]pyrimidine-6-carboxamide;

7-Amino-8-ethyl-2-(3-morpholin-4-ylphenylamino)-5-oxo-5,8-dihydropyrido[2,3-d]pyrimidine-6-carboxamide;

7-Amino-2-(2,3-dihydrobenzo[1,4]dioxin-6-ylamino)-8-ethyl-5-oxo-5,8-dihydropyrido[2,3-d]pyrimidine-6-carboxamide;

7-Amino-8-ethyl-2-(3-fluoro-4-hydroxyphenylamino)-5-oxo-5,8-dihydropyrido[2,3-d]pyrimidine-6-carboxamide;

7-Amino-8-ethyl-2-(3-methylsulfanylphenylamino)-5-oxo-5,8-dihydropyrido[2,3-d]pyrimidine-6-carboxamide;

7-Amino-8-ethyl-2-(4-morpholin-4-ylphenylamino)-5-oxo-5,8-dihydropyrido[2,3-d]pyrimidine-6-carboxamide;

7-Amino-8-ethyl-2-(4-morpholin-4-ylphenylamino)-5-oxo-5,8-dihydropyrido[2,3-d]pyrimidine-6-carboxamide;

7-Amino-8-ethyl-2-(4-morpholin-4-ylphenylamino)-5-oxo-5,8-dihydropyrido[2,3-d]pyrimidine-6-carboxamide;

7-Amino-8-ethyl-2-(2-fluorophenylamino)-5-oxo-5,8-dihydropyrido[2,3-d]pyrimidine-6-carboxamide;

7-Amino-2-[4-(4,4-difluoro[1,4]bipiperidyl-1'-yl)-2-methoxyphenylamino]-8-ethyl-5-oxo-5,8-dihydropyrido[2,3-d]pyrimidine-6-carboxamide 7-Amino-8-ethyl-2-[2-methoxy-4-(4-trifluoromethyl[1,4]bipiperidyl-1'-yl)phenylamino]-5-oxo-5,8-dihydropyrido[2,3-d]pyrimidine-6-carboxamide 7-Amino-2-{4-[4-(3,3-difluoropyrrolidin-1-yl)piperid-1-yl]-2-methoxyphenylamino}-8-ethyl-5-oxo-5,8-dihydropyrido[2,3-d]pyrimidine-6-carboxamide 7-Amino-8-ethyl-2-[4-(4-ethylpiperazin-1-yl)-2-fluoro-6-methoxyphenylamino]-5-oxo-5,8-dihydropyrido[2,3-d]pyrimidine-6-carboxamide;

7-Amino-2-[4-(1-cyclopropylpiperid-4-yl)-2-methoxyphenylamino]-8-ethyl-5-oxo-5,8-dihydropyrido[2,3-d]pyrimidine-6-carboxamide;

7-Amino-2-(2-dimethylaminomethylchroman-6-ylamino)-8-ethyl-5-oxo-5,8-dihydropyrido[2,3-d]pyrimidine-6-carboxamide;

7-Amino-2-[5-chloro-4-(4-cyclopropylpiperazin-1-yl)-2-methoxyphenylamino]-8-ethyl-5-oxo-5,8-dihydropyrido[2,3-d]pyrimidine-6-carboxamide;

7-Amino-8-ethyl-2-[2-methoxy-4-(4-morpholin-4-ylpiperid-1-yl)phenylamino]-5-oxo-5,8-dihydropyrido[2,3-d]pyrimidine-6-carboxyamide;

7-Amino-2-[4-(4-cyclopropylpiperazin-1-yl)-2-difluoromethoxyphenylamino]-8-ethyl-5-oxo-5,8-dihydropyrido[2,3-d]pyrimidine-6-carboxamide;

7-Amino-2-[4-(4-cyclopropylpiperazin-1-yl)-2-methoxyphenylamino]-8-ethyl-5-oxo-5,8-dihydropyrido[2,3-d]pyrimidine-6-carboxamide;

7-Amino-8-ethyl-2-{2-methoxy-4-[1-(3,3,3-trifluoropropyl)piperid-4-yl]phenylamino}-5-oxo-5,8-dihydropyrido[2,3-d]pyrimidine-6-carboxamide;

7-Amino-2-[2-chloro-4-(4-ethylpiperazin-1-yl)phenylamino]-8-ethyl-5-oxo-5,8-dihydropyrido[2,3-d]pyrimidine-6-carboxamide;

7-Amino-8-ethyl-2-[4-(4-ethylpiperazin-1-yl)-3-trifluoromethyl phenylamino]-5-oxo-5,8-dihydropyrido[2,3-d]pyrimidine-6-carboxamide;

7-Amino-8-ethyl-2-(4-morpholin-4-ylmethylphenylamino)-5-oxo-5,8-dihydropyrido[2,3-d]pyrimidine-6-carboxamide;

7-Amino-8-ethyl-5-oxo-2-{4-[4-(3,3,3-trifluoropropyl)piperazin-1-yl]phenylamino}-5,8-dihydropyrido[2,3-d]pyrimidine-6-carboxamide;

7-Amino-8-ethyl-2-[4-(4-ethylpiperazin-1-yl)-3-fluorophenylamino]-5-oxo-5,8-dihydropyrido[2,3-d]pyrimidine-6-carboxamide;

6-(4-Morpholin-4-ylphenylamino)-9-oxo-1,3,4,9-tetrahydro-2H-1,4-a,5,7-tetraaza-phenanthrene-10-carboxamide;

7-Amino-8-ethyl-2-[4-(4-ethyl piperazin-1-yl)-2-methoxyphenylamino]-5-oxo-5,8-dihydropyrido[2,3-d]pyrimidine-6-carboxamide;

7-Amino-8-ethyl-2-[4-(1-methylpiperid-4-ylmethoxy)phenylamino]-5-oxo-5,8-dihydropyrido[2,3-d]pyrimidine-6-carboxamide;

7-Amino-2-[4-(4-cyclopropylpiperazin-1-yl)phenylamino]-8-ethyl-5-oxo-5,8-dihydropyrido[2,3-d]pyrimidine-6-carboxamide;

7-Amino-8-ethyl-2-[4-(4-ethylpiperazin-1-yl)-2-methyl phenylamino]-5-oxo-5,8-dihydropyrido[2,3-d]pyrimidine-6-carboxamide;

7-Amino-8-ethyl-2-[4-(4-ethyl[1,4]diazepan-1-yl)phenylamino]-5-oxo-5,8-dihydropyrido[2,3-d]pyrimidine-6-carboxamide;

8-(4-Morpholin-4-ylphenylamino)-5-oxo-1,2,3,5-tetrahydro-3,7,9,9b-tetraaza-cyclopenta[a]naphthalene-4-carboxamide;

7-Amino-8-ethyl-5-oxo-2-{4-[2-(3-trifluoromethylpiperid-1-yl)ethyl]phenylamino}-5,8-dihydropyrido[2,3-d]pyrimidine-6-carboxamide;

7-Amino-8-ethyl-2-[4-(3-morpholin-4-ylpropyl)phenylamino]-5-oxo-5,8-dihydropyrido[2,3-d]pyrimidine-6-carboxamide;

7-Amino-8-ethyl-5-oxo-2-{4-[1-(2,2,2-trifluoroethyl)piperid-4-yl]phenylamino}-5,8-dihydropyrido[2,3-d]pyrimidine-6-carboxamide;

7-Amino-8-ethyl-2-(4-(S)-1-morpholin-3-ylmethyl phenylamino)-5-oxo-5,8-dihydropyrido[2,3-d]pyrimidine-6-carboxamide;

7-Amino-8-isobutyl-2-[4-(2-morpholin-4-ylethyl)phenylamino]-5-oxo-5,8-dihydropyrido[2,3-d]pyrimidine-6-carboxamide;

7-Amino-8-ethyl-2-{4-[2-(3-fluoroazetidin-1-yl)ethyl]phenylamino}-5-oxo-5,8-dihydropyrido[2,3-d]pyrimidine-6-carboxamide;

7-Amino-2-[4-(2-morpholin-4-ylethyl)phenylamino]-5-oxo-8-propyl-5,8-dihydropyrido[2,3-d]pyrimidine-6-carboxamide;

7-Amino-8-ethyl-2-[4-(2-hydroxyethyl)phenylamino]-5-oxo-5,8-dihydropyrido[2,3-d]pyrimidine-6-carboxamide;

7-amino-8-ethyl-2-(4-hydroethylphenylamino)-5-oxo-5,8-dihydropyrido[2,3-d]pyrimidine-6-carboxamide;

7-Amino-8-ethyl-2-(2-methyl-1,2,3,4-tetrahydroisoquinolin-6-ylamino)-5-oxo-5,8-dihydropyrido[2,3-d]pyrimidine-6-carboxamide;

7-Amino-2-{4-[2-(1,1-dioxo-1lambda6-thiomorpholin-4-yl)ethyl]phenylamino}-8-ethyl-5-oxo-5,8-dihydropyrido[2,3-d]pyrimidine-6-carboxamide;

7-Amino-8-ethyl-2-{4-[2-(4-methyl-3-oxopiperazin-1-yl)ethyl]phenylamino}-5-oxo-5,8-dihydropyrido[2,3-d]pyrimidine-6-carboxamide;

7-Amino-8-ethyl-5-oxo-2-{4-[1-(3,3,3-trifluoropropyl)piperid-4-yl]phenylamino}-5,8-dihydropyrido[2,3-d]pyrimidine-6-carboxamide;

7-Amino-8-ethyl-5-oxo-2-{4-[1-(3,3,3-trifluoropropyl)piperid-4-yl]phenylamino}-5,8-dihydropyrido[2,3-d]pyrimidine-6-carboxamide;

7-Amino-2-(4-dimethylaminomethylphenylamino)-5-oxo-8-(2,2,2-trifluoroethyl)-5,8-dihydropyrido[2,3-d]pyrimidine-6-carboxamide;

7-Amino-2-[3-chloro-4-(4-pyrrolidin-1-ylpiperid-1-yl)phenylamino]-8-ethyl-5-oxo-5,8-dihydropyrido[2,3-d]pyrimidine-6-carboxamide;

7-Amino-2-[3-chloro-4-(4-pyrrolidin-1-ylpiperid-1-yl)phenylamino]-8-ethyl-5-oxo-5,8-dihydropyrido[2,3-d]pyrimidine-6-carboxamide;

7-Amino-8-ethyl-5-oxo-2-(4-pyrid-2-ylmethylphenylamino)-5,8-dihydropyrido[2,3-d]pyrimidine-6-carboxamide;

7-Amino-2-{4-[2-(3,3-difluoropyrrolidin-1-yl)ethyl]phenylamino}-8-ethyl-5-oxo-5,8-dihydropyrido[2,3-d]pyrimidine-6-carboxamide;

7-Amino-8-ethyl-5-oxo-2-(4-pyrrolidin-3-ylphenylamino)-5,8-dihydropyrido[2,3-d]pyrimidine-6-carboxamide;

7-Amino-8-ethyl-5-oxo-2-(4-pyrrolidin-3-ylphenylamino)-5,8-dihydropyrido[2,3-d]pyrimidine-6-carboxamide;

7-Amino-8-ethyl-5-oxo-2-[4-(2-piperid-1-ylethyl)phenylamino]-5,8-dihydropyrido[2,3-d]pyrimidine-6-carboxamide;

7-Amino-2-[4-(2-morpholin-4-ylethyl)phenylamino]-5-oxo-8-(2,2,2-trifluoroethyl)-5,8-dihydropyrido[2,3-d]pyrimidine-6-carboxamide 7-Amino-2-{4-[2-(4,4-difluoropiperid-1-yl)ethyl]phenylamino}-8-ethyl-5-oxo-5,8-dihydropyrido[2,3-d]pyrimidine-6-carboxamide;

7-Amino-8-ethyl-2-[4-(1-methylpyrrolidin-3-yl)phenylamino]-5-oxo-5,8-dihydropyrido[2,3-d]pyrimidine-6-carboxamide;

7-Amino-2-{4-[2-(3,3-difluoropiperid-1-yl)ethyl]phenylamino}-8-ethyl-5-oxo-5,8-dihydropyrido[2,3-d]pyrimidine-6-carboxamide;

7-Amino-8-(3-methoxy-propyl)-2-[4-(2-morpholin-4-ylethyl)phenylamino]-5-oxo-5,8-dihydropyrido[2,3-d]pyrimidine-6-carboxamide;

7-Amino-8-ethyl-2-[4-(1-methylpiperid-3-yl)phenylamino]-5-oxo-5,8-dihydropyrido[2,3-d]pyrimidine-6-carboxamide;

7-Amino-2-(4-dimethylaminomethylphenylamino)-8-isopropyl-5-oxo-5,8-dihydropyrido[2,3-d]pyrimidine-6-carboxamide;

7-Amino-2-(4-dimethylaminomethylphenylamino)-8-isopropyl-5-oxo-5,8-dihydropyrido[2,3-d]pyrimidine-6-carboxamide;

7-Amino-8-ethyl-5-oxo-2-(4-piperid-3-ylphenylamino)-5,8-dihydropyrido[2,3-d]pyrimidine-6-carboxamide;

7-Amino-8-ethyl-5-oxo-2-(1,2,3,4-tetrahydroisoquinolin-7-ylamino)-5,8-dihydropyrido[2,3-d]pyrimidine-6-carboxamide;

7-Amino-8-ethyl-5-oxo-2-(1,2,3,4-tetrahydroisoquinolin-7-ylamino)-5,8-dihydropyrido[2,3-d]pyrimidine-6-carboxamide;

7-Amino-8-ethyl-5-oxo-2-(1,2,3,4-tetrahydroisoquinolin-6-ylamino)-5,8-dihydropyrido[2,3-d]pyrimidine-6-carboxamide;

7-Amino-8-ethyl-2-[4-(1-methylpiperid-4-yloxy)phenylamino]-5-oxo-5,8-dihydropyrido[2,3-d]pyrimidine-6-carboxamide;

7-Amino-8-ethyl-2-[4-(2-morpholin-4-ylethoxy)phenylamino]-5-oxo-5,8-dihydropyrido[2,3-d]pyrimidine-6-carboxamide;

7-Amino-2-(3-dimethylaminomethylphenylamino)-8-ethyl-5-oxo-5,8-dihydropyrido[2,3-d]pyrimidine-6-carboxamide;

7-Amino-8-ethyl-5-oxo-2-[4-(4-pyrrolidin-1-ylpiperid-1-yl)phenylamino]-5,8-dihydropyrido[2,3-d]pyrimidine-6-carboxamide;

7-Amino-8-ethyl-5-oxo-2-[4-(piperid-4-yloxy)phenylamino]-5,8-dihydropyrido[2,3-d]pyrimidine-6-carboxamide;

7-Amino-8-(3-aminopropyl)-2-(4-morpholin-4-ylphenylamino)-5-oxo-5,8-dihydropyrido[2,3-d]pyrimidine-6-carboxamide;

7-Amino-8-ethyl-2-[4-(2-morpholin-4-ylethyl)phenylamino]-5-oxo-5,8-dihydropyrido[2,3-d]pyrimidine-6-carboxamide;

7-Amino-2-(4-dimethylaminomethylphenylamino)-8-ethyl-5-oxo-5,8-dihydropyrido[2,3-d]pyrimidine-6-carboxamide;

7-Amino-8-ethyl-2-[4-(1-ethylpiperid-4-yl)phenylamino]-5-oxo-5,8-dihydropyrido[2,3-d]pyrimidine-6-carboxamide;

7-Amino-8-ethyl-5-oxo-2-(4-piperid-4-ylphenylamino)-5,8-dihydropyrido[2,3-d]pyrimidine-6-carboxamide;

7-Amino-2-[3-chloro-4-(4-ethylpiperazin-1-yl)phenylamino]-8-ethyl-5-oxo-5,8-dihydropyrido[2,3-d]pyrimidine-6-carboxamide 7-Amino-8-ethyl-2-[3-methoxy-4-(3-piperid-1-ylpropoxy) phenylamino]-5-oxo-5,8-dihydropyrido[2,3-d]pyrimidine-6-carboxamide 7-Amino-8-ethyl-5-oxo-2-{4-[2-(4-trifluoromethylpiperid-1-yl)ethyl]phenylamino}-5,8-dihydropyrido[2,3-d]pyrimidine-6-carboxamide 7-Amino-2-{4-[2-(cis-2,6-dimethylmorpholin-4-yl)ethyl] phenylamino}-8-ethyl-5-oxo-5,8-dihydropyrido[2,3-d]pyrimidine-6-carboxamide 7-Amino-2-(4-diethylaminomethylphenylamino)-8-ethyl-5-oxo-5,8-dihydropyrido[2,3-d]pyrimidine-6-carboxamide 7-Amino-2-(4-dimethylaminomethylphenylamino)-8-(3-methoxy-propyl)-5-oxo-5,8-dihydropyrido[2,3-d]pyrimidine-6-carboxamide 7-Amino-8-ethyl-2-[4-(4-ethylpiperazin-1-yl)-2-fluorophenylamino]-5-oxo-5,8-dihydropyrido[2,3-d]pyrimidine-6-carboxamide 7-Amino-2-{4-[1-(2-cyanoethyl)piperid-4-yl]phenylamino}-8-ethyl-5-oxo-5,8-dihydropyrido[2,3-d]pyrimidine-6-carboxamide 7-Amino-8-ethyl-2-{4-[1-(3-fluoropropyl)piperid-4-yl]phenylamino}-5-oxo-5,8-dihydropyrido[2,3-d]pyrimidine-6-carboxylic acid amide 7-Amino-8-ethyl-2-[4-(4-ethyl piperazin-1-yl)-3-methylphenylamino]-5-oxo-5,8-dihydropyrido[2,3-d]pyrimidine-6-carboxamide 7-Amino-2-[4-(4-cyclopropylpiperazin-1-yl)-2-ethylphenylamino]-8-ethyl-5-oxo-5,8-dihydropyrido[2,3-d]pyrimidine-6-carboxamide (±)-7-Amino-2-trans-[4-(2-dimethylaminocyclopropyl)phenylamino]-8-ethyl-5-oxo-5,8-dihydropyrido[2,3-d]pyrimidine-6-carboxamide 7-Amino-2-[4-(4-cyclopropylpiperazin-1-yl)-5-fluoro-2-methoxyphenylamino]-8-ethyl-5-oxo-5,8-dihydropyrido[2,3-d]pyrimidine-6-carboxamide 7-Amino-2-[4-(4-cyclopropylpiperazin-1-yl)-3-fluoro-2-methoxyphenylamino]-8-ethyl-5-oxo-5,8-dihydropyrido[2,3-d]pyrimidine-6-carboxamide 7-Amino-2-[4-(4-cyclopropylpiperazin-1-yl)-2-ethoxyphenylamino]-8-ethyl-5-oxo-5,8-dihydropyrido[2,3-d]pyrimidine-6-carboxamide 7-Amino-8-ethyl-5-oxo-2-(4-propylphenylamino)-5,8-dihydropyrido[2,3-d]pyrimidine-6-carboxamide 7-Amino-8-ethyl-5-oxo-2-(4-propoxyphenylamino)-5,8-dihydropyrido[2,3-d]pyrimidine-6-carboxamide 7-Amino-8-ethyl-2-(6-methoxypyrid-3-ylamino)-5-oxo-5,8-dihydropyrido[2,3-d]pyrimidine-6-carboxamide 7-Amino-8-ethyl-2-(4-fluorophenylamino)-5-oxo-5,8-dihydropyrido[2,3-d]pyrimidine-6-carboxamide 7-Amino-8-ethyl-2-(4-methoxyphenylamino)-5-oxo-5,8-dihydropyrido[2,3-d]pyrimidine-6-carboxamide 7-Amino-2-(benzo[1,3]dioxol-5-ylamino)-8-ethyl-5-oxo-5,8-dihydropyrido[2,3-d]pyrimidine-6-carboxamide 7-Amino-8-ethyl-5-oxo-2-(4-piperid-1-ylphenylamino)-5,8-dihydropyrido[2,3-d]pyrimidine-6-carboxamide 8-Ethyl-2-{2-methoxy-4-[1-(3,3,3-trifluoropropyl)piperid-4-yl]phenylamino}-7-methylamino-5-oxo-5,8-dihydropyrido[2,3-d]pyrimidine-6-carboxamide 7-Amino-8-isobutyl-2-{2-methoxy-4-[1-(3,3,3-trifluoropropyl)piperid-4-yl]phenylamino}-5-oxo-5,8-dihydropyrido[2,3-d]pyrimidine-6-carboxamide 7-Amino-8-cyclopropylmethyl-2-{2-methoxy-4-[1-(3,3,3-trifluoropropyl)piperid-4-yl]phenylamino}-5-oxo-5,8-dihydropyrido[2,3-d]pyrimidine-6-carboxamide 7-Amino-8-(2-methoxyethyl)-2-{2-methoxy-4-[1-(3,3,3-trifluoropropyl)piperid-4-yl]phenylamino}-5-oxo-5,8-dihydropyrido[2,3-d]pyrimidine-6-carboxamide 7-Amino-2-{2-methoxy-4-[1-(3,3,3-trifluoropropyl)piperid-4-yl]phenylamino}-5-oxo-8-(tetrahydrofuran-2-ylmethyl)-5,8-dihydropyrido[2,3-d]pyrimidine-6-carboxamide 7-Amino-8-ethyl-5-oxo-2-{4-[1-(3,3,3-trifluoropropyl)azetidin-3-yl]phenylamino}-5,8-dihydropyrido[2,3-d]pyrimidine-6-carboxamide 7-Amino-2-{5-fluoro-2-methoxy-4-[1-(3,3,3-trifluoropropyl)piperid-4-yl]phenylamino}-8-isobutyl-5-oxo-5,8-dihydropyrido[2,3-d]pyrimidine-6-carboxamide 7-Amino-8-ethyl-5-oxo-2-[4-(1,2,3,6-tetrahydropyrid-4-yl)phenylamino]-5,8-dihydropyrido[2,3-d]pyrimidine-6-carboxamide 7-Amino-2-(2-methoxy-4-piperid-4-ylphenylamino)-5-oxo-8-phenyl-5,8-dihydropyrido[2,3-d]pyrimidine-6-carboxamide 7-Amino-8-(2-hydroxyethyl)-2-(2-methoxy-4-piperid-4-ylphenylamino)-5-oxo-5,8-dihydropyrido[2,3-d]pyrimidine-6-carboxamide 7-Amino-2-{2-methoxy-4-[1-(3,3,3-trifluoropropyl)piperid-4-yl]phenylamino}-5-oxo-8-thiazol-2-ylmethyl-5,8-dihydropyrido[2,3-d]pyrimidine-6-carboxamide 7-Amino-2-{2-methoxy-4-[1-(3,3,3-trifluoropropyl)piperid-4-yl]phenylamino}-5-oxo-8-thiazol-5-ylmethyl-5,8-dihydropyrido[2,3-d]pyrimidine-6-carboxamide 7-Amino-8-(2-hydroxy-2-methylpropyl)-2-(2-methoxy-4-piperid-4-ylphenylamino)-5-oxo-5,8-dihydropyrido[2,3-d]pyrimidine-6-carboxamide 8-(2-Acetylaminoethyl)-7-amino-2-{2-methoxy-4-[1-(3,3,3-trifluoropropyl)piperid-4-yl]phenylamino}-5-oxo-5,8-dihydropyrido[2,3-d]pyrimidine-6-carboxamide 7-Amino-8-(2-aminoethyl)-2-(4-morpholin-4-yl phenylamino)-5-oxo-5,8-dihydropyrido[2,3-d]pyrimidine-6-carboxamide 7-Amino-2-(4-morpholin-4-ylphenylamino)-5-oxo-8-pyrrolidin-3-ylmethyl-5,8-dihydropyrido[2,3-d]pyrimidine-6-carboxamide 7-Amino-8-ethyl-2-[4-(4-ethylpiperazin-1-yl)-2-hydroxyphenylamino]-5-oxo-5,8-dihydropyrido[2,3-d]pyrimidine-6-carboxamide 7-Amino-2-(4-morpholin-4-ylphenylamino)-5-oxo-8-piperid-4-ylmethyl-5,8-dihydropyrido[2,3-d]pyrimidine-6-carboxamide 7-Amino-2-(2-methoxy-4-morpholin-4-ylphenylamino)-5-oxo-8-pyrrolidin-3-ylmethyl-5,8-dihydropyrido[2,3-d]pyrimidine-6-carboxamide 7-Amino-8-ethyl-2-(2-methoxy-4-piperid-4-ylphenylamino)-4-methyl-5-oxo-5,8-dihydropyrido[2,3-d]pyrimidine-6-carboxamide 7-Amino-2-{2-methoxy-4-[1-(3,3,3-trifluoropropyl)piperid-4-yl]phenylamino}-5-oxo-8-thiophen-2-ylmethyl-5,8-dihydropyrido[2,3-d]pyrimidine-6-carboxamide 7-Amino-8-isobutyl-2-[2-methoxy-4-(4-morpholin-4-ylpiperid-1-yl)phenylamino]-5-oxo-5,8-dihydropyrido[2,3-d]pyrimidine-6-carboxamide 7-Amino-2-(4-morpholin-4-ylphenylamino)-5-oxo-8-pyrrolidin-2-ylmethyl-5,8-dihydropyrido[2,3-d]pyrimidine-6-carboxamide 7-Amino-8-ethyl-2-{2-methoxy-4-[1-(3,3,3-trifluoropropyl)-1,2,3,6-tetrahydropyrid-4-yl]phenylamino}-5-oxo-5,8-dihydropyrido[2,3-d]pyrimidine-6-carboxamide 7-Amino-2-[4-(4-ethylpiperazin-1-yl)-2-methoxyphenylamino]-8-(2-hydroxy-2-methylpropyl)-5-oxo-5,8-dihydropyrido[2,3-d]pyrimidine-6-carboxamide 7-Amino-8-(2-hydroxy-2-methylpropyl)-2-{2-methoxy-4-[1-(3,3,3-trifluoropropyl)piperid-4-yl]phenylamino}-5-oxo-5,8-dihydropyrido[2,3-d]pyrimidine-6-carboxamide 7-Amino-8-(2-hydroxy-2-methylpropyl)-2-[4-(4-ethylpip-erid-1-yl)-2-methoxyphenylamino]-5-oxo-5,8-dihydro-pyrido[2,3-d]pyrimidine-6-carboxamide 7-Amino-2-[4-(1-cyclopropylpiperid-4-yl)-2-methoxyphe-nylamino]-8-(2-hydroxy-2-methylpropyl)-5-oxo-5,8-di-hydropyrido[2,3-d]pyrimidine-6-carboxamide 7-Amino-8-(2-hydroxy-2-methylpropyl)-2-{2-methoxy-4-[1-(2-methoxyethyl)piperid-4-yl]phenylamino}-5-oxo-5,8-dihydropyrido[2,3-d]pyrimidine-6-carboxamide 7-Amino-2-[2-methoxy-4-(1-methylpiperid-4-yl)pheny-lamino]-5-oxo-8-phenyl-5,8-dihydropyrido[2,3-d]pyri-midine-6-carboxamide 7-Amino-8-(3-fluorophenyl)-2-[2-methoxy-4-piperid-4-ylphenylamino]-5-oxo-5,8-dihydropyrido[2,3-d]pyrimi-dine-6-carboxamide 7-Amino-8-(4-fluorophenyl)-2-[2-methoxy-4-piperid-4-ylphenylamino]-5-oxo-5,8-dihydropyrido[2,3-d]pyrimi-dine-6-carboxamide 7-Amino-2-[2-methoxy-4-piperid-4-ylphenylamino]-5-oxo-8-m-tolyl-5,8-dihydropyrido[2,3-d]pyrimidine-6-car-boxamide 7-Amino-2-[2-methoxy-4-piperid-4-ylphenylamino]-5-oxo-8-p-tolyl-5,8-dihydropyrido[2,3-d]pyrimidine-6-carboxa-mide 7-Amino-8-(3-methoxyphenyl)-2-(2-methoxy-4-piperid-4-ylphenylamino)-5-oxo-5,8-dihydropyrido[2,3-d]pyrimi-dine-6-carboxamide 7-Amino-2-[2-methoxy-4-(2-pyrrolidin-1-ylethyl)pheny-lamino]-5-oxo-8-phenyl-5,8-dihydropyrido[2,3-d]pyri-midine-6-carboxamide 7-Amino-8-(4-fluorophenyl)-2-[2-methoxy-4-(1-methylpip-erid-4-yl)phenylamino]-5-oxo-5,8-dihydropyrido[2,3-d]pyrimidine-6-carboxamide 7-Amino-2-[2-methoxy-4-(1-methylpiperid-4-yl)pheny-lamino]-5-oxo-8-m-tolyl-5,8-dihydropyrido[2,3-d]pyri-midine-6-carboxamide 7-Amino-2-{2-methoxy-4-[1-(3,3,3-trifluoropropyl)pip-erid-4-yl]phenylamino}-5-oxo-8-phenyl-5,8-dihydropy-rido[2,3-d]pyrimidine-6-carboxamide 7-Amino-2-[4-(4-ethylpiperazin-1-yl)-2-methoxypheny-lamino]-5-oxo-8-phenyl-5,8-dihydropyrido[2,3-d]pyri-midine-6-carboxamide in the form of base or of acid-addition salt, and also in the form of hydrate or solvate.

Combinations of the groups of compounds according to the invention also form part of the invention as an embodiment.

In accordance with the invention, the compounds of general formula (I) may be prepared according to the process that follows.

According to a first embodiment, the process according to the invention includes the step of nucleophilic substitution of a compound of formula (IX)

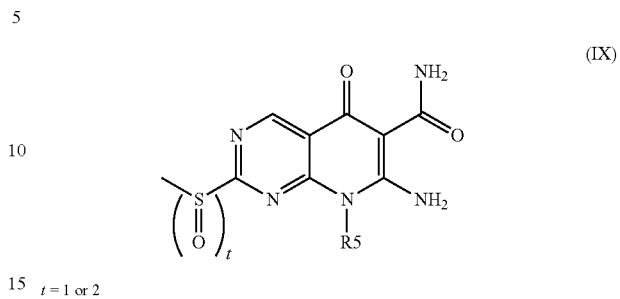

$t = 1$ or $2$ by means of a primary amine of formula (A):

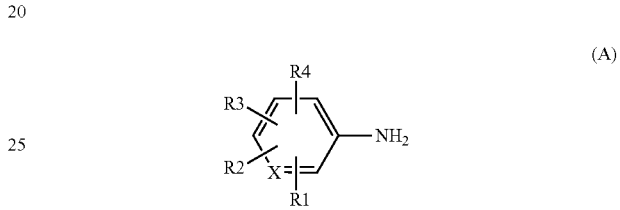

in which $R_1$, $R_2$, $R_3$, $R_4$ and $R_5$ are as defined in the general formula (I). This process leads to the formation of a compound of formula (I), in particular of formula (I").

In accordance with Scheme 1 below, ethyl 4-chloro-2-methylthiopyridine-5-carboxylate (II with A=CH) (prepared according to Todd et al., *J. Amer. Chem. Soc.* (1943), 65, 350-354; Pesson, M., *Eur. J. Med. Chem.* (1974), 9(6), 585-590; Shadbolt, R., *J. Chem. Soc.* (1967), 13, 1172-1178) or ethyl 4-chloro-6-methyl-2-methylthiopyridine-5-carboxylate (II with A=C-Me) (prepared according to the method described in WO 2005/105 801) is reacted with an amine of formula $R_5$—$NH_2$ (in which $R_5$ is as defined previously in relation to formula (I) according to the invention) in an organic solvent such as THF or dioxane, and in the presence of an organic base, for example triethylamine, at room temperature, according to the method described by D. Boschelli et al. in *J. Med. Chem.* (1998), 41, 4365-4377, to give an ethyl 4-amino-2-methylthiopyridine-5-carboxylate derivative of formula (III).

Scheme 1

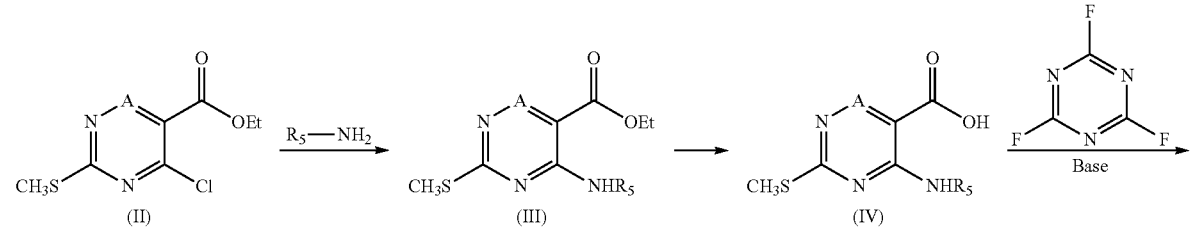

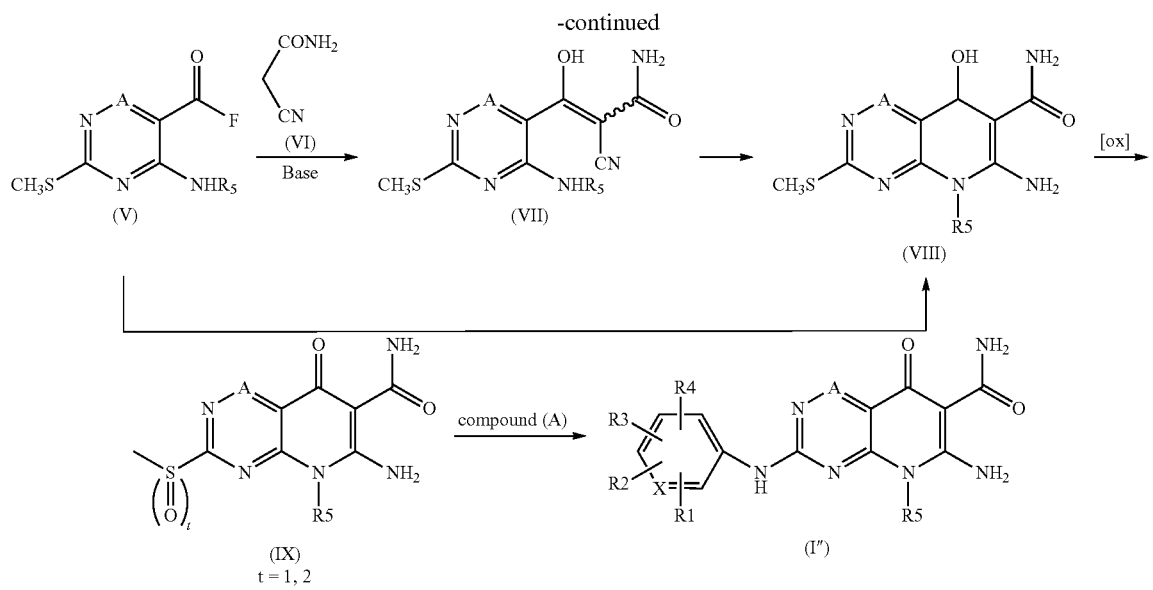

The ester group of the 4-aminopyrimidine derivative of formula (III) is then hydrolysed with sodium or potassium or lithium hydroxide, at a temperature of between 20 and 100°C., to give the corresponding carboxylic acid of formula (IV). The carboxylic acid group is then activated via methods known to those skilled in the art, such as its conversion into acid chloride using thionyl chloride, or advantageously its conversion into the acid fluoride of formula (V) by reacting it with an excess of cyanuric fluoride ($C_3N_3F_3$) in an inert solvent such as dichloromethane, in the presence of an organic base such as pyridine or, advantageously, triethylamine. For further details regarding this reaction, reference may be made to Synthesis 1973, 487.

The acid fluoride of formula (V) thus obtained is condensed with cyanoacetamide of formula (VI), in the presence of a strong base such as sodium hydride (NaH) in a polar solvent, advantageously DMF, at ordinary temperature. If 2 equivalents of NaH are added, a β-keto cyanoacetamide of formula (VII) may be obtained, which is cyclized to a pyrido[2,3-d]pyrimidine derivative of formula (VIII) by heating in a polar solvent such as DMF, DMSO or n-butanol, at a temperature above 100°C. On the other hand, if the acid fluoride of formula (V) is placed in contact with cyanoacetamide of formula (VI) in the presence of 2 equivalents of sodium hydride, in a first stage, and a third equivalent is then added after the in situ formation of the β-keto cyanoacetamide, then the compound of formula (V) is cyclized directly to the pyrido[2,3-d]pyrimidine derivative of formula (VIII). The methylsulfanyl group of the compounds of formula (VIII) is then oxidized ([Ox]symbol in Scheme 1) to the corresponding sulfoxide (n=1) and sulfone (n=2) derivatives by reaction with oxidizing agents such as m-perchlorobenzoic acid, hydrogen peroxide, sodium perborate and potassium hydrogen sulfate or trans-2-phenylsulfonyl-3-phenyloxaziridine, as described, for example, by D. Boschelli et al. in *J. Med. Chem.* (1998), 41, 4365-4377 and in the international PCT patent application published under the number WO 96/34867. The sulfone and sulfoxide mixture of formula (IX) reacts with a primary amine via aromatic nucleophilic substitution in a polar solvent such as DMF, DMSO or NMP, at a temperature of between 75 and 150°C., to give the compounds of formula (I″), which is a subgroup of the compounds of formula (I) with A representing —CH= and $R_6$ representing a hydrogen atom, which are subjects of the present invention. It is understood that, in the process described in Scheme 1, the groups $R_1$, $R_2$, $R_3$, $R_4$ or $R_5$ may comprise one or more temporary protecting groups.

According to another embodiment, the process according to the invention includes the step of reacting a compound of general formula (XIV) or (XV):

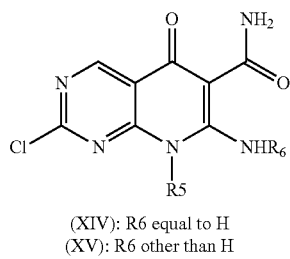

(XIV): R6 equal to H
(XV): R6 other than H and a compound of general formula (A):

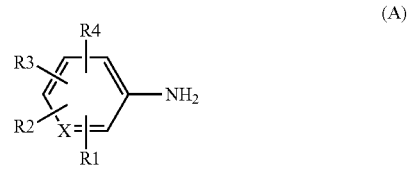

(A)

in which $R_1$, $R_2$, $R_3$, $R_4$, $R_5$ and $R_6$ are defined as in the general formula (I), via a nucleophilic substitution reaction or a coupling reaction of Buchwald/Hartwig type catalysed with a palladium complex. This process leads to the formation of a compound of formula (I), in particular of formulae (I″) and (I‴).

Scheme 2

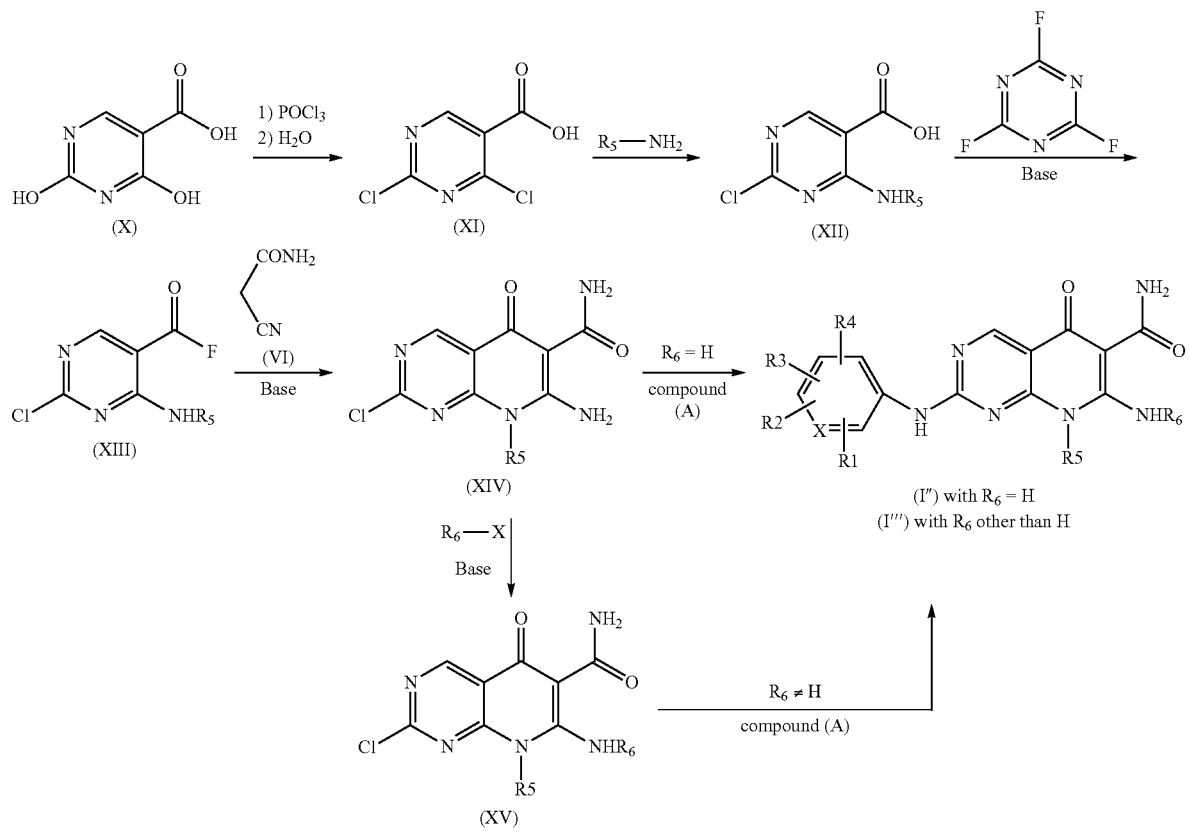

In accordance with Scheme 2, uracil-5-carboxylic acid (X) is reacted with phosphorus oxychloride in the presence of N,N-diethylaniline according to the method of V. H. Smith and B. E. Christensen (J. Am. Chem. Soc. 1955, 20, 829) to give 2,4-dichloro-5-pyrimidinecarboxylic acid (XI). It is advantageously possible to use directly commercial 2,4-dichloro-5-pyrimidinecarboxylic acid chloride, which is subjected to a controlled hydrolysis. The chlorine atom in position 4 of the intermediate (XI) is selectively substituted with an amine of formula $R_5$—$NH_2$ (in which $R_5$ is as defined previously in relation to formula (I) according to the invention) in an organic solvent such as THF or dioxane, and in the presence of an organic base, for example triethylamine, at room temperature, to give a 4-amino-2-chloropyrimidine-5-carboxylic acid derivative of formula (XII). The carboxylic acid group is then activated via methods known to those skilled in the art, such as its conversion into acid chloride using thionyl chloride, or advantageously by converting it into acid fluoride of formula (XIII) by reacting it with an excess of cyanuric fluoride in an inert solvent such as dichloromethane, in the presence of an organic base, such as triethylamine.

The acid fluoride of formula (XIII) thus obtained is condensed with cyanoacetamide of formula (VI), in the presence of an excess of a strong base such as sodium hydride (NaH) in a polar solvent, advantageously DMF, at ordinary temperature. In the presence of 2 equivalents of sodium hydride and then addition of a third equivalent after in situ formation of the β-keto cyanoacetamide, the compound of formula (XIII) is converted directly at ordinary temperature into the pyrido[2,3-d]pyrimidine derivative of formula (XIV). The chloro intermediate (XIV) may react directly with a primary or secondary amine by aromatic nucleophilic substitution or by Buchwald/Hartwig coupling catalysed with a metal such as palladium, at a temperature of between 75 and 150°C., optionally in a microwave machine, to give the compounds of formula (I″), which is a subgroup of the compounds of formula (I) that are subjects of the present invention, in which $R_6$ represents a hydrogen atom and A represents —CH=. The chloro intermediate (XIV) may be alkylated beforehand on the exocyclic amino group to give (XV) in the presence of a base such as sodium hydride or potassium tert-butoxide and of an alkylating agent, advantageously an alkyl iodide, in a polar solvent such as DMF, to give finally the compounds of formula (I″), which is a subgroup of the compounds of formula (I) that are subjects of the present invention with $R_6 \neq H$ and as defined above and A representing —CH=. It is understood that, in the process described in Scheme 2, the groups $R_1$, $R_2$, $R_3$, $R_4$, $R_5$ or $R_6$ may comprise one or more temporary protecting groups.

In Schemes 1 and 2, the starting compounds and the reagents, when their preparation method is not described, are commercially available or described in the literature, or else may be prepared according to methods that are described therein or that are known to those skilled in the art.

According to another of its aspects, a subject of the invention is also the compounds of formulae (VII), (VIII), (IX) and (XV) with $R_6$ not being a hydrogen atom, the said compounds being defined in the synthetic Schemes 1 and 2. These compounds are useful as synthetic intermediates for the compounds of formula (I).

The examples that follow describe the preparation of certain compounds in accordance with the invention. These examples are not limiting, and serve merely to illustrate the present invention. The numbers of the compounds presented as examples refer to those given in the table hereinbelow, which illustrates the chemical structures and physical properties of a number of compounds according to the invention.

The following abbreviations and empirical formulae are used:
$CH_2Cl_2$ dichloromethane
HPLC high-performance liquid chromatography
LC/MS liquid chromatography/mass spectrometry
d doublet
DMF dimethylformamide
DMSO dimethyl sulfoxide
dppf diphenylphosphinoferrocene
$Et_3N$ triethylamine
h hour(s)
HCl hydrochloric acid
MHz MegaHertz
m multiplet or unresolved complex
min minute(s)
MeOH methanol
$MgSO_4$ magnesium sulfate
NaCl sodium chloride
$NaHCO_3$ sodium hydrogen carbonate
NaOH sodium hydroxide
$Na_2SO_4$ sodium sulfate
$NH_4Cl$ ammonium chloride
$NH_4OH$ ammonium hydroxide
NMP N-methylpyrrolidinone
ppm parts per million
s singlet
t triplet
THF tetrahydrofuran

EXAMPLE 1

7-Amino-8-ethyl-2-[(4-hydroxyphenyl)amino]-5-oxo-5,8-dihydropyrido[2,3-d]pyrimidine-6-carboxamide

1.1: Ethyl 4-ethylamino-2-methylthio-5-pyrimidinecarboxylate

To a solution of 15.0 g (64.0 mmol) of ethyl 4-chloro-2-methylthio-5-pyrimidinecarboxylate and 195 mL (1.39 mol) of triethylamine in 226 mL of THF are added 14.6 mL of aqueous 70% ethylamine solution. The mixture is stirred at room temperature for 2 hours. After diluting in water, the resulting mixture is extracted with ethyl acetate and the organic phase is dried over $MgSO_4$. The product is purified by chromatography on silica gel, eluting with a cyclohexane/EtOAc mixture (8/15). 13.7 g of expected product are obtained in the form of a colourless oil. Yield=89%.

1.2: 4-Ethylamino-2-methylthio 5-pyrimidinecarboxylic acid

A mixture containing 6.33 g (26.0 mmol) of ethyl 4-ethylamino-2-methylthio-5-pyrimidinecarboxylate, 65 mL (65.0 mmol) of 1N NaOH and 60 mL of ethanol is refluxed for 1 hour. The ethanol is evaporated off under reduced pressure and the residue is diluted in 100 mL of water. 65 mL of aqueous 1N HCl solution are added and the white precipitate formed is drained by suction. The solid is rinsed with water and dried under vacuum. 5.1 g of expected product are obtained in the form of a white solid. Melting point=188°C. Yield=92%.

1.3: 4-Ethylamino-2-methylthio-5-pyrimidinecarboxylic acid fluoride

To a solution containing 3.0 g (14.0 mmol) of 4-ethylamino-2-methylthio-5-pyrimidinecarboxylic acid and 2.1 mL (15.0 mmol) of triethylamine in 50 mL of $CH_2Cl_2$ are added 2.3 mL (28.0 mmol) of cyanuric fluoride. The mixture is stirred for 3 hours and the solution is diluted with 250 mL of $CH_2Cl_2$ and 75 mL of ice-cold water. After separation of the phases by settling, the organic phase is washed with 75 mL of ice-cold water and dried over $MgSO_4$. The solvent is then evaporated off under reduced pressure. 3.0 g of expected product are obtained in the form of a greenish gum. The yield is quantitative.

1.4: 7-Amino-8-ethyl-2-(methylthio)-5-oxo-5,8-dihydropyrido[2,3-d]pyrimidine-carboxamide To a solution of 1.18 g (14.0 mmol) of cyanoacetamide in 20 mL of anhydrous DMF, cooled to 0-5°C., are added 1.12 g (28 mmol) of 60% NaH. After the addition, the mixture is stirred for 10 minutes at room temperature and then cooled again in an ice-water bath, and the solution of the acid fluoride (14.0 mmol) prepared in step 1.3 in 30 mL of anhydrous DMF is added. The reaction mixture is stirred at room temperature for 30 minutes, and 0.56 g (14.0 mmol) of 60% NaH is added. The mixture is stirred for 1 hour at room temperature, and 100 mL of water are then added. The precipitate is separated out by filtration, rinsed with water, drained by suction and then dried in an oven. 2.85 g of the expected product are obtained in the form of a yellow solid. Yield=73%.

1.5: 7-Amino-8-ethyl-2-(methylsulfonyl)-5-oxo-5,8-dihydropyrido[2,3-d]pyrimidine-6-carboxamide To a solution of 0.60 g (2.15 mmol) of the compound obtained in step 1.4 in 20 mL of N-methylpyrrolidinone are added 1.08 g (4.83 mmol) of meta-chloroperbenzoic acid. The mixture is stirred at room temperature for 24 hours and then evaporated to dryness. The solid residue is taken up in aqueous $NaHCO_3$ solution and then filtered off. The solid is drained by suction and then dried in an oven. 0.4 g of the expected product is obtained in the form of a pale yellow solid. Yield=60%.

1.6: 7-Amino-8-ethyl-2-[(4-hydroxyphenyl)amino]-5-oxo-5,8-dihydropyrido-[2,3-d]pyrimidine-6-carboxamide To a solution of 0.40 g (1.29 mmol) of the product obtained in step 1.5 in 4 mL of anhydrous DMSO is added 0.160 g (1.47 mmol) of 4-aminophenol. The reaction mixture is heated at 110°C. overnight and then evaporated to dryness. The solid residue is purified by chromatography on silica gel, eluting with a dichloromethane/methanol gradient (100/0 to 90/10). 0.090 g of the expected product is obtained in the form of an off-white solid. Yield=20%. m.p. >260°C. $M+H^+=341$.

$^1H$ NMR (DMSO-$d_6$; 400 MHz): δ11.70 (broad s, 1H); 9.85 (s, 1H); 8.89 (s, 1H); 7.95 (broad s, 1H); 7.48 (d, 2H); 7.72 (d, 2H); 4.29 (q, 2H); 1.20 (t, 3H).

EXAMPLE 2

7-Amino-8-ethyl-2-[4-(4-methylpiperazine-1-carbonyl)phenylamino]-5-oxo-5,8-dihydropyrido[2,3-d]pyrimidine-6-carboxamide

2.1 (4-Methylpiperazin-1-yl)(4-nitrophenyl)methanone

A mixture of 2.0 g of 4-nitrobenzoic acid (11.97 mmol), 10.42 mL of diisopropylethylamine (59.84 mmol) and 1.46 mL of 1-methylpiperazine (13.16 mmol) in 40 mL of DMF is cooled to 2-5°C. on an ice bath. 11.53 g (35.9 mmol) of O-benzotriazolyltetramethylisouronium tetrafluoroborate (TBTU, CAS No.=125700-67-6) are then added portionwise and the mixture is stirred at temperature overnight. The reaction mixture is diluted with dichloromethane and saturated aqueous NaCl solution. After separation of the phases by settling, the aqueous phase is extracted with dichloromethane. The organic phases are combined, dried over $Na_2SO_4$, filtered and concentrated under vacuum. The oily residue containing insoluble material is drained by suction and then rinsed with dichloromethane and a small amount of methanol. 1.67 g of the expected product are obtained in the form of a pale pink solid, which is used as obtained without further purification. Yield=56%.

2.2: (4-Aminophenyl)(4-methylpiperazin-1-yl)methanone

To 1.67 g (6.70 mmol) of the product prepared in step 2.1 partially dissolved in 50 mL of methanol are added, under an inert atmosphere, 71 mg of 10% palladium-on-charcoal. The reaction mixture is stirred at room temperature under 3 bar of hydrogen for 2 hours 30 minutes and then filtered through Celite. After evaporating to dryness, 1.5 g of the expected product are obtained in the form of an orange oil, which is used as obtained in the following step. Quantitative yield.

2.3: 2,4-Dichloro-5-pyrimidinecarboxylic acid

Method A:

To 10.0 g (64.06 mmol) of uracil-5-carboxylic acid (Aldrich Chemical Company) partially dissolved in 20 mL of DMF are added, under cold conditions, 59.7 mL (0.64 mol) of phosphorus oxychloride and 10.3 mL (64.7 mmol) of N,N-diethylaniline, and the mixture is then heated at 90°C. for 2 hours 40 minutes. After cooling to room temperature and evaporating off half the excess $POCl_3$, the medium is poured onto ice and then extracted with ether. The ether phases are combined, dried over sodium sulfate, filtered and concentrated under vacuum. 8.1 g (41.97 mmol) of 2,4-dichloro-5-pyrimidinecarboxylic acid are obtained in a yield of 65%.

Method B:

To a solution of 9 g (42.8 mmol) of 2,4-dichloro-5-pyrimidinecarboxylic acid chloride (Manchester Organics Limited) in 60 mL of ether are added 10 mL of water and the reaction mixture is stirred vigorously at 35°C. for 1 hour. After addition of ether and separation of the phases by settling, the organic phase is dried over $Na_2SO_4$, filtered and concentrated under vacuum. 7.7 g of a colourless oil that solidifies rapidly in air, and which is used immediately in the following step, are obtained. Yield=93%.

2.4: 2-Chloro-4-(ethylamino)pyrimidinecarboxylic acid 8.1 g (41.97 mmol) of 2,4-dichloro-5-pyrimidinecarboxylic acid are dissolved in 84 mL of THF in the presence of 81.3 mL (0.923 mol) of triethylamine. 3.4 mL of aqueous 70% ethylamine (41.97 mmol) are added and the mixture is stirred at room temperature for 1 hour 45 minutes. After evaporating off the solvents, the residue is taken up in water and aqueous 1N HCl solution is added slowly to pH 2. The precipitate is isolated by filtration, washed with water and then with an ether/pentane mixture, and dried under vacuum. 7.2 g of a solid very predominantly containing 2-chloro-4-(ethylamino)pyrimidinecarboxylic acid are obtained and are used as obtained in the following step.

2.5: 2-Chloro-4-(ethylamino)pyrimidinecarboxylic acid fluoride

To a solution containing 7.0 g (34.72 mmol) of acid prepared in step 2.4 and 5.32 mL (38.19 mmol) of triethylamine in 98 mL of dichloromethane are added 5.89 mL (69.79 mmol) of cyanuric fluoride. The mixture is stirred for 3 hours and the solution is diluted with 590 mL of $CH_2Cl_2$ and 190 mL of ice-cold aqueous $NaHCO_3$. The organic phase is washed twice with 190 mL of ice-cold aqueous $NaHCO_3$ and dried over $MgSO_4$. The solvent is then evaporated off under reduced pressure. 7.0 g of expected product are obtained in the form of a red oil that solidifies slowly, and that is used as obtained in the following step. Quantitative yield.

2.6: 7-Amino-2-chloro-8-ethyl-5-oxo-5,8-dihydropyrido[2,3-d]pyrimidine-6-carboxamide To a solution, cooled to 2-5°C. on an ice bath, of 6.29 g (74.78 mmol) of cyanoacetamide in 140 mL of anhydrous DMF are added portionwise 5.98 g (149.55 mmol) of 60% sodium hydride. The mixture is stirred for 15 minutes at 2-5°C. and this suspension is then added rapidly to the solution of 14.5 g (71.22 mmol) of the acid fluoride prepared in step 2.5 in 155 mL of anhydrous DMF, precooled to 2-5°C. on an ice bath. The mixture is stirred overnight at room temperature and then cooled to 2-5°C., and 2.99 g (74.78 mmol) of 60% sodium hydride are added portionwise. The medium is stirred for 4 hours at room temperature, ice is then added slowly to destroy the excess hydride, and the reaction medium is poured into an ice-water mixture. The resulting mixture is acidified by adding aqueous 0.1 N HCl solution. The precipitate formed is isolated by filtration, rinsed with water and then dried in an oven, followed by rinsing with pentane. 14.0 g of expected product are finally obtained in the form of a pale orange solid. Yield=73.4%.

2.7: 7-Amino-8-ethyl-2-[4-(4-methylpiperazine-1-carbonyl)phenylamino]-5-oxo-5,8-dihydropyrido[2,3-d]pyrimidine-6-carboxamide A mixture of 0.3 g (1.12 mmol) of the product prepared in step 2.6 and 491 mg (2.24 mmol) of the product prepared in step 2.2 in 6 mL of NMP is placed in a 10 mL microwave tube. The sealed tube is placed in a microwave oven (CEM machine, Discover model) and the mixture is heated under pressure at 120°C. for 60 minutes at a power of 75 W, and then cooled to room temperature. 15 mL of water and then 5 mL of saturated aqueous $NaHCO_3$ are added and the precipitate formed is drained by suction and then dried in an oven. The crude solid is purified by chromatography on a column of silica, eluting with a dichloromethane/methanol gradient (100/0 to 90/10). 0.055 g of the expected product is obtained in the form of an orange powder. m.p.=281°C. %. $M+H^+=$ 451. Yield=11%.

¹H NMR (DMSO-d₆, 400 MHz): δ11.8 (broad s, 1H); 10.3 (s, 1H); 10.2 (d, 1H); 9.0 (s, 1H); 8.0 (broad s, 1H); 7.8 (d, 2H); 7.40 (d, 2H); 7.2 (d, 1H); 4.4 (q, 2H); 3.5 (m, 4H); 3.30 (s, 3H); 2.30 (m, 4H); 1.3 (t, 3H).

EXAMPLE 3

7-Amino-8-cyclopentyl-2-(4-morpholin-4-ylphenylamino)-5-oxo-5,8-dihydropyrido[2,3-d]pyrimidine-6-carboxamide

3.1: 2-Chloro-4-(cyclopentylamino)pyrimidinecarboxylic acid

A suspension of 10 g (51.82 mmol) of 2,4-dichloro-5-pyrimidinecarboxylic acid in 100 mL of THF is cooled on an ice bath to 2-5°C., and a solution of 5.12 mL (51.82 mmol) of cyclopentylamine and 21.67 mL (155.45 mmol) of triethylamine in 40 mL of THF is added dropwise. The mixture is stirred at room temperature for 2 hours. The THF is evaporated off and the residue is then diluted with water. The resulting mixture is acidified with aqueous 1N HCl solution to pH 2 and then extracted twice with dichloromethane. The organic phases are combined, dried over Na₂SO₄, filtered and concentrated under vacuum. The solid recovered is triturated in ether, drained by suction and dried in an oven. 5.28 g of the expected product are obtained in the form of a beige-coloured solid, which is used as obtained in the following step. Yield=42%.

3.2: 2-Chloro-4-(cyclopentylamino)pyrimidinecarboxylic acid fluoride

To a suspension of 5.24 (21.68 mmol) of the product prepared in step 3.1 in 140 mL of dichloromethane are added 3.02 mL (21.68 mmol) of triethylamine and then 2.75 mL (35.52 mmol) of cyanuric fluoride. The mixture is stirred at room temperature for 4 hours and the solution is diluted with 150 mL of dichloromethane. The organic phase is washed three times with 200 mL of ice-cold aqueous NaHCO₃, dried over MgSO₄, filtered and concentrated under vacuum. 5.2 g of the expected product are obtained in the form of an orange solid. Yield=98%.

3.3: 7-Amino-2-chloro-8-cyclopentyl-5-oxo-5,8-dihydropyrido[2,3-d]pyrimidine-6-carboxamide To a solution, cooled to 2-5°C. on an ice bath, of 1.88 g (22.41 mmol) of cyanoacetamide in 20 mL of anhydrous DMF are added portionwise 1.8 g (44.82 mmol) of 60% sodium hydride. The mixture is stirred for 15 minutes at 2-5°C., and this suspension is then added rapidly to a solution of 5.2 g (21.34 mmol) of the acid fluoride prepared in step 3.2 in 20 mL of anhydrous DMF precooled to 2-5°C. The mixture is stirred overnight at room temperature and then cooled to 2-5°C. on an ice bath, and 0.90 g (22.41 mmol) of 60% sodium hydride is added portionwise. The reaction mixture is stirred for 3 hours at room temperature and then poured into a mixture of ice, 100 mL of water and 150 mL of aqueous 1N HCl. The yellow precipitate formed is isolated by filtration, rinsed with water and then dried in an oven, after which it is rinsed with pentane. 5.4 g of a mixture containing the expected cyclized product and the non-cyclized product are finally obtained in the form of an orange powder. The mixture is purified by chromatography on a column of silica, eluting with a dichloromethane/methanol gradient (99/1 to 96/4). 0.6 g of the expected product is finally obtained in the form of a pale yellow solid. Yield=9%.

3.4: 7-Amino-8-cyclopentyl-2-(4-morpholin-4-ylphenylamino)-5-oxo-5,8-dihydropyrido[2,3-d]pyrimidine-6-carboxamide A mixture of 184 mg (0.60 mmol) of the product prepared in step 3.3 and 0.266 g (1.49 mmol) of N-(4-aminophenyl) morpholine (Lancaster) in 6 mL of NMP is placed in a 10 mL microwave tube. The sealed tube is placed in the microwave oven (CEM machine, Discover model) and the mixture is heated under pressure at 90°C. for 1 hour at a power of 100 W and then cooled to room temperature. 20 mL of water and then 5 mL of saturated aqueous NaHCO₃ are added and the precipitate formed is drained by suction and dried in an oven. The crude solid is purified by chromatography on a column of silica, eluting with a dichloromethane/methanol gradient (98/2 to 95/5). 0.065 g of the expected product is obtained in the form of a beige-coloured powder. Yield=24%. m.p.=265°C. M+H⁺=450.

¹H NMR (DMSO-d₆, 400 MHz): δ11.5-12.5 (very broad s, 1H); 10.4 (d, 1H); 9.6 (s, 1H); 8.9 (s, 1H); 7.4 (d, 2H); 7.1 (d, 1H); 6.9 (d, 2H), 5.0 (m, 1H); 3.7 (m, 4H); 3.0 (m, 4H); 2.2-2.5 (m, 2H); 1.3-1.9 (m, 6H)

EXAMPLE 4

7-Amino-8-ethyl-2-(2-methoxy-4-piperid-4-ylphenylamino)-5-oxo-5,8-dihydropyrido[2,3-d]pyrimidine-6-carboxamide hydrochloride

4.1: 4-Bromo-2-methoxy-1-nitrobenzene 18.4 g (83.64 mmol) of 2-fluoro-4-bromonitrobenzene (Aldrich) are almost fully dissolved in 300 mL of anhydrous methanol. 19.9 mL (106.22 mmol) of a 30% solution of sodium methoxide in methanol are added dropwise and the mixture is stirred overnight at room temperature. The methanol is evaporated off under reduced pressure, the medium is taken up in ethyl acetate and water, and the aqueous phase is then acidified by adding aqueous 1N HCl. After separation of the phases by settling, the organic phase is washed with saturated aqueous NaCl, dried over Na₂SO₄, filtered and concentrated under vacuum. 17.4 g of the expected product are obtained in the form of a yellow solid. Yield=89.7%.

4.2: tert-Butyl 4-(3-methoxy-4-nitrophenyl)-3,6-dihydro-2H-pyridine-1-carboxylate Argon is bubbled for 10 minutes into a mixture of 4.64 g (20.0 mmol) of the product prepared in step 4.1, 6.25 g (20.2 mmol) of 3,6-dihydro-2H-pyridine-1-N-Boc-4-boronic acid pinacol ester (Frontier Scientific) and 8.29 g (60.0 mmol) of potassium carbonate in 125 mL of anhydrous DMF. 0.98 g (1.2 mmol) of PdCl₂dppf.CH₂Cl₂ is added and the mixture is heated under argon at 90°C. for 3 hours. The resulting mixture is diluted with ethyl acetate and washed twice with water and once with saturated aqueous NaCl. The organic phase is dried over Na₂SO₄, filtered and concentrated under vacuum. The crude solid obtained is purified by chromatography on a column of silica, eluting with a cyclohexane/ethyl acetate gradient (75/25 to 70/30). 6.02 g of a pale yellow solid are obtained, and are triturated in cyclohexane and then drained by suction and dried in an oven. 5.89 g of the expected product are finally recovered in the form of a white solid. Yield=88%.

4.3: tert-Butyl 4-(4-amino-3-methoxyphenyl)piperidine-1-carboxylate 4.27 g (12.77 mmol) of the product prepared in step 4.2 in 130 mL of an ethyl acetate/ethanol mixture (v/v=1/1) are placed in a hydrogenation autoclave, and 0.54 g of 10% palladium-on-charcoal is added, under an inert atmosphere. The mixture is stirred under a hydrogen pressure of 3 bar at room temperature. After filtration through thin glass fibre paper and evaporation under reduced pressure, 3.87 g of the expected product are obtained in the form of a pink solid, which is used as obtained in the following step. Yield=99%.

4.4: tert-Butyl 4-[4-(7-amino-6-carbamoyl-8-ethyl-5-oxo-5,8-dihydropyrido[2,3-d]pyrimidin-2-ylamino)-3-methoxyphenyl]piperidine-1-carboxylate A mixture of 0.45 g (1.63 mmol) of the product prepared in step 2.6 and 1.00 g (3.25 mmol) of the product prepared in step 4.3 in 3 mL of NMP is placed in a round-bottomed flask. The suspension is heated at 110°C. for 3 hours. 30 mL of water and then 5 mL of saturated aqueous $NaHCO_3$ are added and the precipitate formed is drained by suction and then dried in an oven. The crude solid is purified by chromatography on a column of silica, eluting with a dichloromethane/methanol gradient (100/0 to 93/7). 0.52 g of the expected product is obtained in the form of a beige-coloured powder. Yield=59.5%.

4.5: 7-Amino-8-ethyl-2-(2-methoxy-4-piperid-4-ylphenylamino)-5-oxo-5,8-dihydropyrido[2,3-d]pyrimidine-6-carboxamide hydrochloride 0.51 g (0.95 mmol) of the product prepared in step 4.4 is suspended in 10 mL of a dichloromethane/methanol mixture (v/v=8/2), and 3.55 mL (14.20 mmol) of a 4N solution of hydrogen chloride in dioxane are added. The mixture is stirred at room temperature overnight, and ether is added. The solid is drained by suction, rinsed with pentane and dried in an oven. 0.48 g the expected product is obtained in the form of a beige-coloured solid, which is used as obtained in the following step. Yield (dihydrochloride)=99.1°A. m.p.=117°C. $M+H^+=408$.

$^1H$ NMR (DMSO-d6; 400 MHz): δ11.8 (broad s, 1H); 10,4 (very broad s, <1H); 10.2 (s, 1H); 9.0 (s, 1H); 8.9 (broad s, 1H); 8.1 (broad s, 1H); 7.8 (d, 1H); 7.2 (d, 1H); 4.3 (q, 2H); 3.4 (m, 2H), 3.0 (m, 2H); 2.8 (m, 1H); 1.9 (m, 4H); 1.3 (t, 3H).

EXAMPLE 5

7-Amino-8-ethyl-2-{2-methoxy-4-[1-(3,3,3-trifluoropropyl)piperid-4-yl]phenylamino}-5-oxo-5,8-dihydropyrido[2,3-d]pyrimidine-6-N-methylcarboxamide hydrochloride

5.1: 7-Amino-8-ethyl-2-{2-methoxy-4-[1-(3,3,3-trifluoropropyl)piperid-4-yl]-phenylamino}-5-oxo-5,8-dihydropyrido[2,3-d]pyrimidine-6-N-methylcarboxamide 0.47 g (0.92 mmol) of the hydrochloride prepared in step 4.5 is suspended in 7.8 mL of a dichloromethane/glacial acetic acid mixture (v/v=5/1) and sodium 3,3,3-trifluoropropionaldehyde (Alfa Aesar) and then sodium triacetoxyborohydride are added portionwise. The reaction mixture is stirred for 2.5 hours and then poured into 50 mL of aqueous $NaHCO_3$. A solid is isolated by filtration, and is purified by chromatography on a column of silica, eluting with a dichloromethane/methanol gradient (100/0 to 90/10). After triturating in ether, 0.25 g of the expected product is finally obtained in the form of a beige-coloured solid. Yield=50.9%.

5.2: 7-Amino-8-ethyl-2-{2-methoxy-4-[1-(3,3,3-trifluoropropyl)piperid-4-yl]-phenylamino}-5-oxo-5,8-dihydropyrido[2,3-d]pyrimidine-6-N-methylcarboxamide hydrochloride 0.19 g (0.36 mmol) of the product prepared in step 4.6 is dissolved in 4 mL of a dichloromethane/methanol mixture (v/v=4/1), and 1.09 mL (1.09 mmol) of 1.0 M hydrogen chloride in ether are added. The suspension is stirred for 5 minutes and then diluted with ether, and the precipitate is drained by suction, rinsed with ether and with pentane, and dried under vacuum. 0.22 g of the expected product is obtained in the form of an ochre-coloured powder. Yield (dihydrochloride)=96.5%. m.p.=199°C. $M+H^+=534$.

$^1H$ NMR (DMSO-d6; 400 MHz): δ11.8 (broad s, 1H); 11.2 (very broad s, <1H); 10.3 (broad s, 1H); 9.0 (s, 1H); 8.8 (s, 1H); 8.1 (broad s, 1H); 7.9 (d, 1H); 7.2 (very broad s, <1H); 7.0 (s, 1H); 6.9 (d, 1H); 4.3 (q, 2H); 3.9 (s, 3H); 3.6 (m, 2H), 3.4 (m, 2H); 3.0-3.2 (m, 2H); 2.9 (m, 1H); 2.0 (m, 4H); 1.3 (t, 3H).

EXAMPLE 6

7-Amino-2-[4-(1-cyclopropylpiperid-4-yl)-2-methoxyphenylamino]-8-ethyl-5-oxo-5,8-dihydropyrido[2,3-d]pyrimidine-6-carboxamide hydrochloride

6.1: 7-Amino-2-[4-(1-cyclopropylpiperid-4-yl)-2-methoxyphenylamino]-8-ethyl-5-oxo-5,8-dihydropyrido[2,3-d]pyrimidine-6-carboxamide The hydrochloride prepared in step 4.5 is converted into the base form by treatment with aqueous 1N NaOH followed by filtration and drying in an oven. 0.44 g (1.0 mmol) of this product is suspended in 10 mL of anhydrous methanol. 0.57 mL (10.0 mmol) of glacial acetic acid, 3 Åmolecular sieves predried under vacuum, 0.9 mmol (4.5 mmol) of (1-ethoxycyclopropoxy)trimethylsilane and 0.188 g (3.0 mmol) of sodium cyanoborohydride are added. The mixture is heated for 1 hour at 80°C., and 2 mL of tetrahydrofuran and a further 0.45 mL (2.25 mmol) of (1-ethoxycyclopropoxy)trimethylsilane are added. The reaction mixture is heated for 20 hours at 80°C. and is then allowed to cool to room temperature and evaporated to dryness. The residue obtained is purified by chromatography on a column of silica, eluting with a dichloromethane/methanol gradient (96/4 to 90/10). After triturating in an ether/isopropanol mixture (v/v=3/1) and then in ethyl acetate/isopropanol, 0.126 g of the expected product is finally obtained in the form of a white solid. Yield=26%.

6.2: 7-Amino-2-[4-(1-cyclopropylpiperid-4-yl)-2-methoxyphenylamino]-8-ethyl-5-oxo-5,8-dihydropyrido[2,3-d]pyrimidine-6-carboxamide hydrochloride To a suspension of 0.126 g (0.26 mmol) of the product prepared in step 7.1 in 2.6 mL of methanol is added 0.79 mL (0.79 mmol) of 1.0 M hydrochloric ether. The mixture is stirred for 5 minutes at room temperature and then diluted with ether. The precipitate is drained by suction, rinsed with ether and with pentane, and dried under vacuum. 0.133 g of the expected product is obtained in the form of a beige-coloured solid. Yield (dihydrochloride)=92%. m.p.=226-228°C. M+H+=478.

$^1$H NMR (DMSO-d$_6$, 400 MHz): δ11.8 (broad s, 1H); 10.6 (broad s, ~0.5H); 10.4 (broad s, ~1.5H); 9.0 (s, 1H); 8.8 (s, 1H); 8.1 (broad s, 1H); 7.9 (d, 1H); 7.2 (very broad s, <1H); 7.0 (s, 1H); 6.9 (d, 1H); 4.3 (q, 2H); 3.9 (S, 3H); 3.6 (m, 2H); 2.8-3.4 (m, 4H); 2.0-2.2 (m, 2H); 1.30 (t, 3H); 1.20 (m, 2H); 0.80 (m; 2H)

EXAMPLE 7

7-Amino-8-ethyl-2-(3-morpholin-4-ylphenylamino)-5-oxo-5,8-dihydropyrido[2,3-d]pyrimidine-6-carboxamide A mixture of 0.25 g (0.93 mmol) of the product prepared in step 2.6 and 0.33 g (1.87 mmol) of 3-morpholin-4-ylphenylamine in 4 mL of NMP is placed in a 10 mL microwave tube. The sealed tube is placed in the microwave oven (CEM machine, Discover model) and the mixture is heated under pressure at 90°C. for 30 minutes at 120°C., for 1 hour at a power of 100 W, and is then cooled to room temperature. 20 mL of water and then 5 mL of saturated aqueous NaHCO$_3$ are added and the precipitate formed is drained by suction and then dried in an oven. The crude solid is triturated in methanol, drained by suction, rinsed with ether and with pentane, and dried under vacuum. 0.16 g of the expected product is finally obtained in the form of a beige-coloured powder. Yield=41.8%. m.p.=195°C. M+H+=410.

$^1$H NMR (DMSO-d$_6$, 400 MHz): δ11.8 (broad s, 1H); 10.3 (d, 1H); 10.0 (broad s, 1H); 8.9 (s, 1H); 8.0 (very broad s, <1H); 7.3 (m, 2H); 7.1-7.3 (m, 3H); 6.6 (d, 1H), 4.4 (q, 2H); 3.7 (m, 4H); 3.1 (m, 4H); 1.2 (t, 3H)

EXAMPLE 8

2-[4-(4-Acetylpiperazin-1-yl)phenylamino]-7-amino-8-ethyl-5-oxo-5,8-dihydropyrido[2,3-d]pyrimidine-6-carboxamide

8.1: 1-[4-(4-Nitrophenyl)piperazin-1-yl]ethanone

A solution of 5.0 g (35.44 mmol) of 1-fluoro-4-nitrobenzene and 4.99 g (38.98 mmol) of N-acetylpiperazine in 50 mL of acetonitrile is heated at 60°C. for 15 hours. The resulting mixture is diluted with water and with ethyl acetate. After separation of the phases by settling and extraction of the aqueous phase with ethyl acetate, the organic phases are combined, dried over Na$_2$SO$_4$, filtered and concentrated under vacuum. 7.7 g of the expected product are obtained in the form of a yellow solid, which is used as obtained in the following step. Yield=88.8%.

8.2: 1-[4-(4-Aminophenyl)piperazin-1-yl]ethanone 3.0 g (12.04 mmol) of the product prepared in step 8.1 in 40 mL of ethyl acetate are placed in a hydrogenation autoclave, and 0.15 g of 10% palladium-on-charcoal are added, under an inert atmosphere. The mixture is stirred at a hydrogen pressure of 5 bar at room temperature. After filtering through Celite and evaporating under reduced pressure, 1.6 g of the expected product are obtained in the form of a beige-coloured solid, which is used as obtained in the following step. Yield=61%.

8.3: 2-[4-(4-Acetylpiperazin-1-yl)phenylamino]-7-amino-8-ethyl-5-oxo-5,8-dihydropyrido[2,3-d]pyrimidine-6-carboxamide A mixture of 0.30 g (1.12 mmol) of the product prepared in step 2.6 and 0.49 g (2.24 mmol) of the product prepared in step 8.2 in 5 mL of NMP is placed in a 10 mL microwave tube. The sealed tube is placed in a microwave oven (CEM machine, Discover model) and the mixture is heated under pressure at 90°C. for 30 minutes at a power of 100 W, and then cooled to room temperature. 20 mL of water and then 5 mL of saturated aqueous NaHCO$_3$ are added, and the precipitate formed is drained by suction and then dried in an oven. The crude solid is triturated in methanol, drained by suction, rinsed with ether and with pentane, and dried under vacuum. 0.30 g of the expected product is finally obtained in the form of a beige-coloured powder. Yield=60%. m.p.=179°C. M+H+= 548.

$^1$H NMR (DMSO-d$_6$, 400 MHz): δ11.7 (very broad s, <1H); 10.4 (d, 1H), 9.9 (s, 1H); 8.9 (s, 1H); 8.0 (very broad s, <1H); 7.6 (d, 2H); 7.1 (d, 1H); 6.9 (d, 2H); 4.4 (q, 2H); 3.6 (m, 4H); 3.1 (m, 4H); 2.0 (s, 3H); 1.3 (t, 3H)

EXAMPLE 9

7-Amino-2-[4-(cyclopropanecarbonylmethylamino)phenylamino]-8-ethyl-5-oxo-5,8-dihydropyrido[2,3-d]pyrimidine-6-carboxamide

9.1: Methyl-(4-nitrophenyl)cyclopropanecarboxamide

To a solution of 2.0 g (13.14 mmol) of N-methyl-4-nitroaniline (Aldrich) and 1.59 mL (19.72 mmol) of pyridine in 15 mL of tetrahydrofuran are added slowly 1.43 mL (15.77 mmol) of cyclopropanoyl chloride. The mixture is refluxed for 2 hours and evaporated to dryness. The residue is taken up in an ethyl acetate/water mixture and the organic phase is then dried over Na$_2$SO$_4$, filtered and concentrated under vacuum. The expected product is obtained in the form of a yellow oil, which is used as obtained in the following step.

9.2: Methyl-(4-aminophenyl)cyclopropanecarboxamide

To a suspension of 3.56 g (54.49 mmol) of zinc powder in 15 mL of concentrated aqueous 33% NH$_4$OH solution are added 1.2 g (5.45 mmol) of the product prepared in step 9.1 dissolved in 15 mL of tetrahydrofuran. The mixture is stirred for 1 hour at room temperature, the zinc is then separated out by filtration and the mixture is extracted with ether. The organic phases are combined, dried over Na$_2$SO$_4$, filtered and concentrated under vacuum. The oily residue is purified by chromatography on a column of silica, eluting with a cyclohexane/ethyl acetate gradient (70/30 to 60/40). 3 g of the expected product are obtained in the form of a yellow oil. Quantitative yield.

9.3: 7-Amino-2-[4-(cyclopropanecarbonylmethylamino)phenylamino]-8-ethyl-5-oxo-5,8-dihydropyrido[2,3-d]pyrimidine-6-carboxamide A mixture of 0.30 g (1.12 mmol) of the product prepared in step 2.6 and 0.43 g (2.24 mmol) of the product prepared in step 9.2 in 4.5 mL of NMP is heated at 90°C. for 3 hours. After addition of water, no precipitate forms. The mixture is left for 48 hours at room temperature, and the precipitate formed is drained by suction. After triturating in dichloromethane, 0.17 g of the expected product is obtained in solid form. m.p.=248°C. M+H$^+$=422. Yield=36%

$^1$H NMR (DMSO-d$_6$, 400 MHz): δ11.8 (very broad s, <1H); 10.2-10.4 (m, 2H), 9.0 (s, 1H); 8.0 (very broad s, <1H); 7.8 (d, 2H); 7.4 (d, 1H); 7.2 (d, 1H); 4.3 (q, 2H); 3.1 (s, 3H); 1.4 (m, 1H); 1.2 (t, 3H); 0.8 (m, 2H); 0.6 (m, 2H)

EXAMPLE 10

7-Amino-8-ethyl-2-[4-(4-ethylpiperazin-1-yl)-2-fluoro-6-methoxyphenylamino]-5-oxo-5,8-dihydro-pyrido[2,3-d]pyrimidine-6-carboxamide hydrochloride 10.1: 1.5-Difluoro-3-methoxy-2-nitrobenzene To a solution of 2.45 g (14.0 mmol) of 1,3,5-trifluoro-2-nitrobenzene in acetone are successively added 2.9 g (21.0 mmol) of K$_2$CO$_3$ powder and 3.5 mL (56.0 mmol) of methyl iodide. The reaction mixture is heated at 50°C. for 2 hours and then filtered and evaporated to dryness. The residue is taken up in ethyl acetate and washed with water and with saturated aqueous NaCl solution. The organic phase is dried over Na$_2$SO$_4$, filtered and concentrated under vacuum. 2.52 g of the expected product are recovered in the form of a yellow solid, which is used as obtained in the following step. Yield=95%.

10.2: tert-Butyl 4-(3-fluoro-5-methoxy-4-nitrophenyl)piperazine-1-carboxylate

To a solution of 2.48 g (13.1 mmol) of the product prepared in step 10.1 in 26 mL of acetonitrile are added 2.43 g (13.1 mmol) of tert-butyl piperazinecarboxylate and 3.36 mL (19.65 mmol) of diisopropylethylamine. The reaction mixture is heated at 90°C. for 20 hours. It is diluted with ethyl acetate and washed with water and then with saturated aqueous NaCl solution. The crude solid is purified by chromatography on a column of silica, eluting with a cyclohexane/ethyl acetate gradient (85/15 to 50/50). A 3.25 g fraction predominantly containing the regioisomer tert-butyl 4-(5-fluoro-3-methoxy-2-nitrophenyl)piperazine-1-carboxylicate is isolated. An impure secondary fraction is purified again on a column of silica, eluting with a dichloromethane/ethyl acetate gradient (96/4 to 94/6). 0.985 g of expected product is finally obtained in the form of a yellow solid. Yield=21%.

10.3: tert-Butyl 4-(4-amino-3-fluoro-5-methoxyphenyl)piperazine-1-carboxylate 0.975 g (2.74 mmol) of the product prepared in step 9.2 in 55 mL of an ethyl acetate/ethanol mixture (v/v=1/1) is placed in a hydrogenation autoclave, and 0.14 g of 10% palladium-on-charcoal is added, under an inert atmosphere. The mixture is stirred at a hydrogen pressure of 3 bar at room temperature for 4 hours. After filtering through thin glass fibre paper and evaporating under reduced pressure, 0.88 g of the expected product is obtained in the form of a violet solid, which is used as obtained in the following step. Yield=99%.

10.4: tert-Butyl 4-[4-(7-amino-6-carbamoyl-8-ethyl-5-oxo-5,8-dihydropyrido[2,3-d]pyrimidin-2-ylamino)-3-fluoro-5-methoxyphenyl]piperazine-1-carboxylate A mixture of 0.36 g (1.35 mmol) of the product prepared in step 2.6 and 0.88 g (2.70 mmol) of the product prepared in step 10.3 in 3 mL of NMP is placed in a round-bottomed flask. The suspension is heated at 100°C. for 5.5 hours. 50 mL of water and then 5 mL of saturated aqueous NaHCO$_3$ are added and the precipitate formed is drained by suction and dried in an oven. The crude solid is purified by chromatography on a column of silica, eluting with a dichloromethane/methanol gradient (100/0 to 96/4). 0.149 g of the expected product is obtained in the form of a violet solid. Yield=20%.

10.5: 7-Amino-8-ethyl-2-(2-fluoro-6-methoxy-4-piperazin-1-ylphenylamino)-5-oxo-5,8-dihydropyrido[2,3-d]pyrimidine-6-carboxamide hydrochloride 0.14 g (0.23 mmol) of the product prepared in step 10.4 is suspended in 4 mL of methanol, and 1.15 mL (4.61 mmol) of a 4N solution of hydrogen chloride in dioxane are added. The mixture is stirred at room temperature overnight, and ether is added. The solid is drained by suction, rinsed with pentane and dried in an oven. 0.10 g of the expected product is obtained in the form of a grey powder, which is used as obtained in the following step. Yield (dihydrochloride)=95%.

10.6: 7-Amino-8-ethyl-2-[4-(4-ethylpiperazin-1-yl)-2-fluoro-6-methoxyphenylamino]-5-oxo-5,8-dihydropyrido[2,3-d]pyrimidine-6-carboxamide 0.1 g (0.23 mmol) of the hydrochloride prepared in step 10.5 is suspended in 3 mL of 1,2-dichloroethane, and 0.13 mL (0.72 mmol) of diisopropylethylamine, 0.04 mL (1.2 mmol) of acetaldehyde and then 0.10 g (0.48 mmol) of sodium triacetoxyborohydride are added portionwise. The mixture is stirred for 2 hours, and poured into 0.25 N sodium hydroxide solution, and dichloromethane is added. After separation of the phases by settling, the aqueous phase is extracted with dichloromethane and the organic phases are combined, dried over Na$_2$SO$_4$, filtered and concentrated under vacuum. A light-brown solid is recovered, which is purified by chromatography on a column of silica, eluting with a dichloromethane/methanol gradient (95/5 to 90/10). 0.085 g of the expected product is obtained in the form of a glassy yellow solid. Yield=73%.

10.7: 7-Amino-8-ethyl-2-[4-(4-ethylpiperazin-1-yl)-2-fluoro-6-methoxyphenylamino]-5-oxo-5,8-dihydropyrido[2,3-d]pyrimidine-6-carboxamide hydrochloride To a solution of 0.08 g (0.18 mmol) of the product prepared in step 10.6 in 5 mL of methanol is added 0.53 mL (0.53 mmol) of 1.0 M hydrochloric ether. The mixture is stirred for 30 minutes at room temperature and then diluted with ether. The precipitate is drained by suction, rinsed with ether and with pentane, and dried under vacuum. 0.133 g of the expected product is obtained in the form of a beige-coloured solid. Yield (dihydrochloride)=77%. m.p. >260°C. M+H$^+$=485.

$^1$H NMR (DMSO-d$_6$, 400 MHz): δ11.8 (broad s, 1H); 11.0 (broad s, 1H), 9.1 (broad s, 1H); 8.9 (broad s, 1H); 8.0 (broad s, 1H), 6.8-7.4 (very broad s, <1H); 6.45 (d, 1H); 6.4 (s, 1H); 3.5-4.4 (s+m, 9H); 3.0-3.3 (m, 6H); 1.3 (t, 3H); 1.0-1.3 (m, 3H)

EXAMPLE 11

7-Amino-8-(3-aminopropyl)-2-(4-morpholin-4-ylphenylamino)-5-oxo-5,8-dihydropyrido[2,3-d]pyrimidine-6-carboxamide hydrochloride

11.1: 4-(3-tert-Butoxycarbonylaminopropylamino)-2-chloropyrimidine-5-carboxylic acid A solution of 2.21 g (11.45 mmol) of 2,4-dichloro-5-pyrimidinecarboxylic acid prepared in step 2.3 (method B) in 20 mL of anhydrous THF is cooled to 2-5°C. on an ice bath. A solution of 4.79 mL (34.35 mmol) of triethylamine and 2 g (11.48 mmol) of tert-butyl (3-aminopropyl)carbamate in 15 mL of anhydrous THF is then added dropwise. The reaction mixture is stirred at room temperature for 30 minutes. Ethyl acetate is added and the organic phase is washed with aqueous 1N HCl and with water. The organic phases are combined, dried over sodium sulfate, filtered and concentrated under vacuum. 3.35 g of the expected product are obtained in the form of a yellow solid. Yield=88.6%.

11.2: tert-Butyl[3-(2-chloro-5-fluorocarbonylpyrimidin-4-ylamino)propyl]-carbamate To a suspension of 4.91 g (14.85 mmol) of the product prepared in step 11.1 in 75 mL of dichloromethane are added 2.07 g (14.85 mmol) of triethylamine and then 1.88 mL (22.28 mmol) of cyanuric fluoride. The mixture is stirred at room temperature for 2 hours and the solution is diluted with 100 mL of dichloromethane. The organic phase is washed three times with 100 mL of ice-cold aqueous $NaHCO_3$, dried over $MgSO_4$, filtered and concentrated under vacuum. 4.56 g of the expected product are obtained, and are used directly in the following step. Yield=98%.

11.3: tert-Butyl[3-(7-amino-6-carbamoyl-2-chloro-5-oxo-5H-pyrido[2,3-d]pyrimidin-8-yl)propyl]carbamate To a solution, cooled to 2-5°C. on an ice bath, of 1.21 g (14.39 mmol) of cyanoacetamide in 20 mL of anhydrous DMF are added portionwise 1.73 g (43.17 mmol) of 60% sodium hydride. The mixture is stirred for 15 minutes at 2-5°C., and this suspension is then added rapidly to the solution of 4.56 g (13.70 mmol) of the acid fluoride prepared in step 11.2 in 30 mL of anhydrous DMF, precooled to 2-5°C. on an ice bath. The mixture is stirred overnight at room temperature and then cooled to 2-5°C., and a further 0.22 g of 60% sodium hydride is added. The medium is stirred overnight at room temperature, and ice is then added slowly to destroy the excess hydride, and the reaction mixture is poured into an ice-water mixture. The resulting mixture is acidified by adding aqueous 1 N HCl solution. The precipitate formed is isolated by filtration, rinsed with water and then dried. The expected product is obtained in the form of an orange solid, which is used as obtained in the following step. Yield=64%.

11.4: tert-Butyl {3-[7-amino-6-carbamoyl-2-(4-morpholin-4-ylphenylamino)-5-oxo-5H-pyrido[2,3-d]pyrimidin-8-yl]propyl}carbamate A mixture of 0.60 g (1.51 mmol) of the product prepared in step 11.3 and 0.53 g (3.02 mmol) of 4-morpholin-4-ylphenylamine in 6.5 mL of NMP is placed in a 10 mL microwave tube. The sealed tube is placed in the microwave oven (CEM machine, Discovery model) and the mixture is heated under pressure at 120°C. for 60 minutes at a power of 75 W, and then cooled to room temperature. 15 mL of water and then 5 mL of saturated aqueous $NaHCO_3$ are added and the precipitate formed is drained by suction and then dried in an oven. The crude solid is triturated in methanol, drained by suction and dried in an oven under vacuum. 0.159 g of the expected product is obtained in solid form. Yield=20%.

11.5: 7-Amino-8-(3-aminopropyl)-2-(4-morpholin-4-ylphenylamino)-5-oxo-5,8-dihydropyrido[2,3-d]pyrimidine-6-carboxamide hydrochloride 0.16 g (0.30 mmol) of the product prepared in step 11.4 is suspended in 4 mL of anhydrous dioxane, and 0.74 mL (2.95 mmol) of a 4N solution of hydrogen chloride in dioxane is added. The mixture is stirred at room temperature for 5 hours, and ether is added. The solid is drained by suction, rinsed with pentane and dried in an oven. 0.14 g of the expected product is obtained in the form of a white powder. Yield (dihydrochloride)=quantitative. m.p.=250°C. M+H$^+$=439.

$^1$H NMR (DMSO-$d_6$, 400 MHz): δ11.9 (broad s, 1H); 10.2-10.4 (very broad s, <1H); 10.2 (s, 1H); 9.0 (s, 1H); 8.4 (broad s, 1H); 8.2 (d, 2H); 7.7 (d, 2H); 7.4 (broad s, 1H); 7.1-7.5 (very broad s, <1H); 4.4 (m, 2H); 3.9 (m, 4H); 3.3 (m, 4H); 2.9 (m, 2H); 2.1 (m, 2H)

EXAMPLE 12

7-Amino-8-ethyl-2-[4-(2-hydroxyethyl)phenylamino]-5-oxo-5,8-dihydropyrido[2,3-d]pyrimidine-6-carboxamide A mixture of 2.1 g (7.89 mmol) of the product prepared in step 2.6 and 2.17 g (15.79 mmol) of 2-(4-aminophenyl)ethanol in 10 mL of NMP is heated at 100°C. for 3 hours in a sealed tube. The hot reaction mixture is poured into a mixture of 125 mL of water and 25 mL of saturated aqueous $NaHCO_3$. The precipitate formed is drained by suction, rinsed with water and then dried in an oven under vacuum. After triturating in ether, 2.5 g of the expected product are obtained in the form of a light-brown solid. Yield=89.2%.

An analytically pure sample is obtained by triturating 0.2 g of the preceding solid in a minimum amount of methanol, draining by suction, rinsing with ether and drying with a vacuum pump. 0.15 g of the pure expected product is thus recovered in the form of a beige-coloured powder.

m.p.=289°C. M+H$^+$=369.

$^1$H NMR (DMSO-d6; 400 MHz): δ11.8 (broad s, 1H); 10.4 (d, 1H); 10.1 (broad s, 1H); 9.0 (s, 1H); 8.0 (broad s, 1H); 7.7 (d, 2H); 7.2 (d, 2H); 4.6 (t, 1H); 4.4 (m, 2H); 3.6 (m, 2H), 2.7 (m, 2H); 1.3 (t, 3H).

EXAMPLE 13

7-Amino-8-ethyl-5-oxo-2-[4-(2-piperid-1-ylethyl)phenylamino]-5,8-dihydropyrido[2,3-d]pyrimidine-6-carboxamide hydrochloride

13.1: Ethyl 2-[4-(7-amino-6-carbamoyl-8-ethyl-5-oxo-5,8-dihydropyrido[2,3-d]pyrimidin-2-ylamino)phenyl]methanesulfonate To a suspension of 1.0 g (2.71 mmol) of the product of Example 12 in 50 mL of tetrahydrofuran cooled to 2-5°C. on an ice-water bath are added 1.51 mL (10.86 mmol) of triethylamine, followed by dropwise addition of 0.84 mL (10.86 mmol) of methanesulfonyl chloride. The reaction mixture is heated at 50°C. for 2 hours. It is poured into water and ethyl acetate is added. The organic phase is washed with aqueous 0.5 N HCl and with saturated aqueous NaCl and then dried over $Na_2SO_4$, filtered and concentrated under vacuum. 0.94 g of the expected product is obtained in the form of a brown solid, in a sufficient purity to perform the following step.

13.2: 7-Amino-8-ethyl-5-oxo-2-[4-(2-piperid-1-yl-ethyl)phenylamino]-5,8-dihydropyrido[2,3-d]pyrimidine-6-carboxamide hydrochloride 1.1 g (2.46 mmol) of the product prepared in step 13.1 and 1.17 mL (11.83 mmol) of piperidine are placed in a round-bottomed flask. The mixture is heated at 60°C. for 2 hours and then concentrated. The residue is purified by chromatography on a column of silica, eluting with a dichloromethane/methanol gradient (100/0 to 90/10). 0.12 g (0.28 mmol) of the expected product is obtained in base form, which is salified by treating with 0.55 mL (0.55 mmol) of 1 M hydrochloric ether in methanol. m.p.=216°C. M+H$^+$=436.

$^1$H NMR (DMSO-d$_6$, 400 MHz): δ11.8 (broad s, 1H); 10.4 (broad s, ~1H); 10.2 (s, 1H); 9.0 (s, 1H); 8.1 (broad s, 1H); 7.7 (d, 2H); 7.1-7.3 (very broad s, <1H); 4.4 (q, 2H); 3.5 (m, 2H); 3.2 (m, 2H); 3.1 (m, 2H); 2.9 (m, 2H); 1.7-1.9 (m, 5H); 1.4 (m, 1H), 1.3 (t, 3H)

EXAMPLE 14

7-Amino-2-[4-(4-cyclopropylpiperazin-1-yl)-2-difluoromethoxyphenylamino]-8-ethyl-5-oxo-5,8-dihydropyrido[2,3-d]pyrimidine-6-carboxamide hydrochloride

14.1: 2-Difluoromethoxy-4-fluoro-1-nitrobenzene

To a solution of 3.14 g (20.0 mmol) 5-fluoro-2-nitrophenol in 36 mL of DMF are added 6.1 g (40.0 mmol) of sodium chlorodifluoroacetate and 3.31 g (24.0 mmol) of powdered sodium carbonate. The reaction mixture is heated at 100°C. for 4 hours 30 minutes and is then allowed to cool to room temperature. Aqueous 4N HCl solution is added and the mixture is stirred at room temperature for 2 hours. The resulting mixture is diluted with 100 mL of water and 100 mL of ether. The aqueous phase is extracted with ether and the organic phases are then combined, washed with aqueous 1N NaOH solution and then with saturated aqueous NaCl, dried over $Na_2SO_4$, filtered and concentrated under vacuum. 3.68 g of the expected product are obtained in the form of a yellow oil, which is used as obtained in the following step. Yield=89%.

14.2: 1-Cyclopropyl-4-(3-difluoromethoxy-4-nitrophenyl)piperazine

To 2.07 g (10.0 mmol) of the product prepared in step 14.1 in 30 mL of acetonitrile are added 5.99 mL (35.0 mmol) of diisopropylethylamine and then 2.09 g (10.5 mmol) of finely ground N-cyclopropylpiperazine (supplier). The reaction mixture is heated at 100°C. for 1 hour 30 minutes, cooled and concentrated under vacuum. The residue is taken up in 75 mL of ethyl acetate and washed with saturated aqueous $NaHCO_3$ solution and with saturated aqueous NaCl solution. The organic phase is dried over $Na_2SO_4$, filtered and concentrated under vacuum. After triturating in cyclohexane, the solid is drained by suction and dried in an oven under vacuum. 2.32 g of the expected product are obtained in the form of a yellow solid, which is used as obtained in the following step. Yield=74.5%.

14.3 4-(4-Cyclopropylpiperazin-1-yl)-2-difluoromethoxyphenylamine 2.32 g (7.4 mmol) of the product prepared in step 14.2 in 50 mL of an ethyl acetate/ethanol mixture (v/v=1/1) are placed in a hydrogenation autoclave, and 0.196 g of 10% palladium-on-charcoal is added, under an inert atmosphere. The mixture is stirred under a hydrogen pressure of 2.5 bar at room temperature for 1 hour 45 minutes. After filtering through thin glass fibre paper and evaporating under reduced pressure, 2.09 g of the expected product are obtained in the form of a beige-coloured solid, which is used as obtained in the following step. Quantitative yield.

14.4: 7-Amino-2-[4-(4-cyclopropylpiperazin-1-yl)-2-difluoromethoxyphenylamino]-8-ethyl-5-oxo-5,8-dihydropyrido[2,3-d]pyrimidine-6-carboxamide A mixture of 0.44 g (1.65 mmol) of the product prepared in step 2.6 and 0.93 g (3.3 mmol) of the product prepared in step 14.3 in 3 mL of NMP is placed in a round-bottomed flask. The solution is heated at 100°C. for 18 hours. 50 mL of water and then 5 mL of saturated aqueous $NaHCO_3$ are added and the precipitate formed is drained by suction and then dried in an oven. The crude solid is purified by chromatography on a column of silica, eluting with a dichloromethane/methanol gradient (100/0 to 90/10). 0.117 g of the expected product is finally obtained in the form of a yellow solid. Yield=12%.

14.5: 7-Amino-2-[4-(4-cyclopropylpiperazin-1-yl)-2-difluoromethoxyphenylamino]-8-ethyl-5-oxo-5,8-dihydropyrido[2,3-d]pyrimidine-6-carboxamide hydrochloride 0.11 g (0.21 mmol) of the product prepared in step 14.4 is suspended in 3 mL of anhydrous dioxane and 0.63 mL (0.63 mmol) of a 1M solution of hydrogen chloride in ether is added. The mixture is diluted with ether and the solid is then drained by suction, rinsed with pentane and dried in an oven. 0.11 g of the expected product is obtained in the form of a yellow powder. Yield (dihydrochloride)=87%. m.p.=204-206°C. M+H$^+$=515.

$^1$H NMR (DMSO-d$_6$, 400 MHz): δ11.8 (broad s, 1H); 11.0 (broad s, 1H); 10.1-10.6 (very broad s, <1H); 9.2 (s, 1H); 8.9 (s, 1H); 8.0 (broad s, 1H); 7.6 (d, 2H); 7.1 (t, 1H); 7.0 (d, 1H); 6.9 (s, 1H); 4.3 (m, 2H); 3.9 (m, 2H); 3.6 (m, 2H); 3.4 (m, 2H); 3.2 (m, 2H); 3.0 (m, 1H); 1.1-1.3 (m, 5H); 0.8 (m, 2H)

EXAMPLE 15

(±)-7-Amino-2-[4-(trans-2-dimethylaminocyclopropyl)phenylamino]-8-ethyl-5-oxo-5,8-dihydropyrido[2,3-d]pyrimidine-6-carboxamide hydrochloride

15.1: (±)-trans-2-(4-Nitrophenyl)cyclopropanecarboxylic acid 20.3 g (125.0 mmol) of (±)-trans-2-phenyl-cyclopropanecarboxylic acid (Aldrich) are added portionwise to 150 mL of concentrated 70% nitric acid solution. The mixture is stirred for 2 hours at room temperature, and the formation of a fine white powder in the reaction medium is observed. The mixture is cooled to 10°C., and the solid is drained by suction, rinsed four times with 40 mL of water and then dried in an oven. The solid is partially dissolved in 700 mL of xylene at 160°C. and is allowed to cool to room temperature. The solid is drained by suction, rinsed with xylene and then with pentane, and dried in an oven under vacuum. 12.6 g of an off-white solid containing a 90/10 mixture of the expected product and of the ortho-nitro regioisomer are obtained. The mixture is used as obtained in the following step. Yield=48%.

15.2: tert-Butyl (±)-[trans-2-(4-nitrophenyl)cyclopropyl]carbamate

To a suspension of 12.4 g (60.0 mmol) of the mixture prepared in step 15.1 in 150 mL of tert-butanol are added 9.2 mL (66.0 mmol) of Et$_3$N, followed by dropwise addition of 14.2 mL (66 mmol) of diphenylphosphoryl azide. The reaction mixture is heated at 95°C. for 4 hours 30 minutes and then allowed to cool to room temperature. The resulting mixture is diluted with 300 mL of ethyl acetate and the organic phase is washed with 150 mL of saturated aqueous NaHCO$_3$ and then with saturated aqueous NaCl. After evaporation, the solid residue is taken up in 50 mL of ethyl acetate and 100 mL of cyclohexane, and is heated until dissolution is complete. The solution is cooled to room temperature, and the precipitate is drained by suction and rinsed with cyclohexane and with pentane. The pink solid is almost totally dissolved in 150 mL of CH$_2$Cl$_2$ and then filtered through silica, eluting with CH$_2$Cl$_2$, followed by a dichloromethane/ethyl acetate mixture (1/4). The filtrate is evaporated to give 7.12 g of the expected product in the form of a light-brown solid. Yield=42.5%.

15.3: tert-Butyl (±)-[trans-2-(4-aminophenyl)cyclopropyl]carbamate 1.39 g (5.0 mmol) of the product prepared in step 15.2 are dissolved in 25 mL of hot ethyl acetate. After cooling to room temperature, 25 mL of absolute ethanol and 0.057 g (0.25 mmol) of platinum (IV) oxide are successively added. The reaction mixture is placed under a hydrogen pressure of 2.75 bar for 2 hours, and is filtered through thin glass fibre paper. The filtrate is concentrated under vacuum and purified by chromatography on a column of silica, eluting with a cyclohexane/ethyl acetate gradient (from 70/30 to 55/45). 1.05 g of the expected product are obtained. Yield=85%.

15.4: tert-Butyl (±)-{trans-2-[4-(7-amino-6-carbamoyl-8-ethyl-5-oxo-5,8-dihydropyrido[2,3-d]pyrimidin-2-ylamino)phenyl]cyclopropyl}carbamate A mixture of 0.87 g (3.5 mmol) of the product prepared in step 2.6 and 0.47 g (1.75 mmol) of the product prepared in step 15.3 in 3 mL of NMP is placed in a round-bottomed flask. The solution is heated at 100°C. for 18 hours. 50 mL of water and then 5 mL of saturated aqueous NaHCO$_3$ are added and the precipitate formed is drained by suction and then dried in an oven. The crude solid is purified by chromatography on a column of silica, eluting with a dichloromethane/methanol gradient (98/2 to 92.5/7.5). 0.46 g of the expected product is finally obtained in the form of an orange solid. Yield=55%.

15.5: (±)-7-Amino-2-[4-(trans-2-aminocyclopropyl)phenylamino]-8-ethyl-5-oxo-5,8-dihydropyrido[2,3-d]pyrimidine-6-carboxamide hydrochloride To a suspension of 0.46 g (0.96 mmol) of the product prepared in step 15.4 in 20 mL of a dichloromethane/methanol mixture (1/1) are added 4.8 mL (19.2 mmol) of 4N hydrogen chloride in dioxane. The mixture is stirred for 5 hours at room temperature and then diluted with ether, and the solid is drained by suction, rinsed with ether and dried in an oven under vacuum. 0.48 g of a dark violet solid is obtained, and is used as obtained in the following step. Yield (dihydrochloride)=quantitative.

15.6: (±)-7-Amino-2-[4-(trans-2-dimethylaminocyclopropyl)phenylamino]-8-ethyl-5-oxo-5,8-dihydropyrido[2,3-d]pyrimidine-6-carboxamide To a suspension of 0.19 g (0.43 mmol) of the product prepared in step 15.5 in 5.4 mL of acetonitrile are added 0.22 mL (1.29 mmol) of diisopropylethylamine and 0.64 mL (8.58 mmol) of 70% formalin. After stirring for 3 minutes, 0.13 g (2.14 mmol) of sodium cyanoborohydride is added and the mixture is stirred for 3 hours at room temperature. The reaction mixture is concentrated and then taken up in 6 mL of water and 3 mL of aqueous 35% NaOH. The solid is drained by suction and dried in an oven under vacuum. It is purified by chromatography on a column of silica, eluting with a dichloromethane/methanol mixture (98/2 to 85/15) containing traces of concentrated aqueous NH$_4$OH. 0.054 g of the expected product is obtained. Yield=31%.

15.7: (±)-7-Amino-2-[4-(trans-2-dimethylaminocyclopropyl)phenylamino]-8-ethyl-5-oxo-5,8-dihydropyrido[2,3-d]pyrimidine-6-carboxamide hydrochloride To a solution of 0.05 g (0.13 mmol) of the product prepared in step 15.6 in 2.5 mL of methanol is added 0.20 mL (0.4 mmol) of 2.0 M hydrochloric ether. The mixture is stirred for 5 minutes at room temperature and then evaporated to dryness. The residue is purified by preparative HPLC. The fraction corresponding to the expected pure product is evaporated to dryness under then taken up in methanol. Ether is added and the solid is drained by suction and dried in an oven under vacuum. 0.031 g of the expected product is obtained. Yield (dihydrochloride)=49%. m.p.=208-210°C. (decomposition). M+H$^+$=408.

$^1$H NMR (DMSO-d$_6$, 400 MHz): δ11.8 (broad s, 1H); 10.7 (broad s, 1H); 10.1-10.4 (very broad s, <1H); 10.2 (s, 1H); 9.0 (s, 1H); 8.1 (broad s, 1H), 7.7 (d, 1H); 6.45 (d, 1H); 7.2 (d, 1H); 4.4 (m, 2H); 3.1 (m, 1H); 2.9 (d, 3H); 2.85 (d, 3H); 2.7 (m, 1H); 1.7 (m, 1H); 1.2-1.4 (m+t, 4H)

EXAMPLE 16

8-Ethyl-2-{2-methoxy-4-[1-(3,3,3-trifluoropropyl)piperid-4-yl]phenylamino}-7-methylamino-5-oxo-5,8-dihydropyrido[2,3-d]pyrimidine-6-carboxamide hydrochloride 16.1: 4-(3-Methoxy-4-nitrophenyl)-1,2,3,6-tetrahydropyridine hydrochloride A solution of 10.0 g (29.91 mmol) of the product prepared in step 4.2 in 120 mL of dichloromethane is cooled to 2-5°C. on an ice-water bath, and 60 mL of a 4N solution of HCl in dioxane (Aldrich) are then added slowly over 1 hour. The reaction mixture is stirred at room temperature overnight. The solid formed is drained by suction, rinsed with ether and then dried in an oven. 7.6 g of the expected product are recovered in the form of a beige-coloured solid. Yield=94%.

16.2: 4-(3-Methoxy-4-nitrophenyl)-1-(3,3,3-trifluoropropyl)-1,2,3,6-tetrahydropyridine A solution of 6.6 g (24.38 mmol) of the hydrochloride prepared in step 16.1 in 110 mL of dichloromethane is cooled in an ice-water bath. 14 mL (243.8 mmol) of glacial acetic acid, 8.19 g (73.14 mmol) of 3,3,3-trifluoropropionaldehyde and 12.9 g (60.95 mmol) of sodium triacetoxyborohydride are successively added portionwise. The mixture is stirred at room temperature for 3 hours and then diluted with dichloromethane, water and aqueous 1N NaOH solution. The aqueous phase is extracted with dichloromethane and the organic phases are combined, dried over $Na_2SO_4$, filtered and concentrated under vacuum. 8.4 g of a yellow oil very predominantly containing the expected product are recovered, and are used as obtained in the following step. Quantitative crude yield.

16.3: 2-Methoxy-4-[1-(3,3,3-trifluoropropyl)piperid-4-yl]phenylamine 1.65 g (5.0 mmol) of the product prepared in step 16.2 are placed in 120 mL of an ethanol/acetic acid mixture (v/v=1/1) in a hydrogenation autoclave, and 0.150 g of platinum (IV) oxide is added, under an inert atmosphere. The mixture is stirred under a hydrogen pressure of 4 bar at room temperature for 4 hours. After filtering through thin glass fibre paper and evaporating to dryness under reduced pressure, the oily residue is taken up in chloroform and washed with aqueous 1N NaOH solution. The organic phase is dried over $Na_2SO_4$, filtered and concentrated under vacuum. 1.5 g of the expected product are obtained in the form of a brown oil, which is used as obtained in the following step. Crude yield=quantitative.

16.4: 2-Chloro-8-ethyl-7-methylamino-5-oxo-5,8-dihydropyrido[2,3-d]pyrimidine-6-carboxamide A suspension of 2 g (7.47 mmol) of the product prepared in step 2.6 in 40 mL of anhydrous NMP is cooled on an ice-water bath, and 0.45 g (11.21 mmol) of 60% sodium hydride is added in a single portion. The mixture is stirred with cooling until the evolution of gas has ceased, and then for 10 minutes at room temperature. The solution is cooled on an ice-water bath and a solution of 0.56 mL (8.97 mmol) of methyl iodide in 5 mL of anhydrous NMP is added dropwise. The mixture is allowed to warm slowly to room temperature, and is stirred for 24 hours. Ice is added, and the reaction mixture is then poured into water. The resulting mixture is acidified to pH 1 by adding aqueous 1N HCl solution. The resulting mixture is left for 48 hours at room temperature, and ethyl acetate is added. This mixture is stirred vigorously for 1 hour. After separation of the phases by settling, the organic phase is dried over $Na_2SO_4$, filtered and concentrated under vacuum. The yellow solid obtained is triturated in ether, drained by suction, rinsed with pentane and dried in an oven under vacuum. 0.7 g of a 90/10 mixture (LC/MS) of the expected product and of the starting material is obtained in the form of a yellow solid, which is used as obtained in the following step.

16.5: 8-Ethyl-2-{2-methoxy-4-[1-(3,3,3-trifluoropropyl)piperid-4-yl]phenylamino}-7-methylamino-5-oxo-5,8-dihydropyrido[2,3-d]pyrimidine-6-carboxamide To a suspension of 0.5 g (1.77 mmol) of the product prepared in step 16.4 in 5 mL of anhydrous DMF are added 1.07 g (3.55 mmol) of the product prepared in step 16.3, and the reaction mixture is heated at 100°C. for 4 hours. It is evaporated to dryness and the residue is purified by chromatography on a column of silica, eluting with a dichloromethane/methanol gradient (100/0 to 95/5). After triturating in methanol, 0.08 g of the expected product is obtained in the form of a white solid.

16.6: 8-Ethyl-2-{2-methoxy-4-[1-(3,3,3-trifluoropropyl)piperid-4-yl]phenylamino}-7-methylamino-5-oxo-5,8-dihydropyrido[2,3-d]pyrimidine-6-carboxamide hydrochloride To a solution of 0.08 g (0.15 mmol) of the product prepared in step 16.5 in 6 mL of a dichloromethane/methanol mixture (v/v=1/1) is added 0.44 mL (0.44 mmol) of a 1M solution of hydrochloric ether. The mixture is stirred for 1 hour at room temperature, and ether is then added. The solid is drained by suction, rinsed with pentane and dried in an oven under vacuum. 0.09 g of the expected product is finally obtained in the form of a yellow solid. Yield (dihydrochloride)=99%. $M+H^+=548$.

$^1$H NMR (DMSO-d6; 400 MHz): δ11.75 (broad s, 1H); 11.1 (broad s, 1H); 10.9 (broad s, 1H); 8.9 (s, 1H); 8.8 (s, 1H); 8.05 (broad s, 1H); 7.9 (d, 1H); 7.0 (s, 1H); 6.85 (d, 1H); 4.3 (q, 2H); 3.85 (s, 3H); 3.65 (m, 2H); 3.35 (m, 2H); 2.9-3.2 (m, 4H); 2.8 (m, 1H); 2.75 (s, 3H); 2.0 (m, 4H); 1.2 (t, 3H).

EXAMPLE 17

7-Amino-8-(2-hydroxy-2-methylpropyl)-2-{2-methoxy-4-[1-(3,3,3-trifluoropropyl)piperid-4-yl]phenylamino}-5-oxo-5,8-dihydropyrido[2,3-d]pyrimidine-6-carboxamide hydrochloride

17.1: 2-Chloro-4-(2-hydroxy-2-methylpropylamino)pyrimidine-5-carboxylic acid A suspension of 19.9 g (86.73 mmol) of 2,4-dichloro-5-pyrimidinecarboxylic acid in 155 mL of THF is cooled on an ice bath to 2-5°C., and a solution of 8.5 g (95.40 mmol) of 1-amino-2-methyl-2-propanol and 36.3 mL (260.19 mmol) of triethylamine in 60 mL of THF is added dropwise. The mixture is stirred at room temperature overnight. Ethyl acetate and water are added. After separation of the phases by settling, the aqueous phase is acidified with aqueous 1N HCl solution to pH 2. The precipitate is isolated by filtration to give 12.6 g of the expected product in the form of a pale yellow solid, which is used as obtained in the following step. Yield=59%.

17.2: 2-Chloro-4-(2-hydroxy-2-methylpropylamino)pyrimidine-5-carboxylic acid fluoride To a solution containing 12.64 g (51.45 mmol) of the acid prepared in step 17.1 and 7.89 mL (56.60 mmol) of triethylamine in 250 mL of dichloromethane are added 6.51 mL (77.18 mmol) of cyanuric fluoride. The mixture is stirred at room temperature overnight and the solution is diluted with 590 mL of $CH_2Cl_2$ and 190 mL of ice-cold aqueous $NaHCO_3$. The organic phase is washed twice with 250 mL of ice-cold aqueous $NaHCO_3$ and dried over $MgSO_4$. The solvent is then evaporated off under reduced pressure. 12.3 g of the expected product are obtained in the form of a yellow oil that solidifies slowly, and which is used as obtained in the following step. Yield=96%.

17.3: 7-Amino-2-chloro-8-(2-hydroxy-2-methylpropyl)-5-oxo-5,8-dihydropyrido[2,3-d]pyrimidine-6-carboxamide To a solution, cooled to 2-5°C. on an ice bath, of 4.4 g (52.36 mmol) of cyanoacetamide in 70 mL of anhydrous DMF are added portionwise 4.19 g (104.72 mmol) of 60% sodium hydride. The mixture is stirred for 15 minutes at 2-5°C., and this suspension is then added rapidly to a solution of 12.35 g (49.87 mmol) of the acid fluoride prepared in step 17.2 in 70 mL of anhydrous DMF, precooled to 2-5°C. The mixture is stirred overnight at room temperature and is then cooled to 2-5°C. on an ice bath, and 2.09 g (52.36 mmol) of 60% sodium hydride are added portionwise. The reaction mixture is stirred for 3 hours at room temperature and then poured into a mixture of ice, 100 mL of water and 150 mL of aqueous 1N HCl. The yellow precipitate formed is isolated by filtration, rinsed with water and then dried in an oven. After triturating in methanol and drying in an oven, 8.84 g of the expected product are finally obtained in the form of a yellow solid. Yield=57%.

17.4: 7-Amino-8-(2-hydroxy-2-methylpropyl)-2-{2-methoxy-4-[1-(3,3,3-trifluoropropyl)piperid-4-yl]phenylamino}-5-oxo-5,8-dihydropyrido[2,3-d]pyrimidine-6-carboxamide To a suspension of 0.82 g (2.62 mmol) of the product prepared in step 17.3 in 6.4 mL of anhydrous NMP are added 1.59 g (5.25 mmol) of the product prepared in step 16.3, and the reaction mixture is heated at 110°C. for 1.5 hours. It is evaporated to dryness and the residue is purified by chromatography on a column of silica, eluting with a dichloromethane/methanol gradient (100/0 to 95/5) containing traces of concentrated aqueous $NH_4OH$. 0.70 g of the expected product is obtained in the form of a white solid. Yield=46%.

17.5: 7-Amino-8-(2-hydroxy-2-methylpropyl)-2-{2-methoxy-4-[1-(3,3,3-trifluoropropyl)piperid-4-yl]phenylamino}-5-oxo-5,8-dihydropyrido[2,3-d]pyrimidine-6-carboxamide hydrochloride A solution of 0.70 g (1.22 mmol) of the product prepared in step 17.4 in 17 mL of methanol is cooled on an ice bath, and 0.91 mL (3.65 mmol) of a 4N solution of hydrogen chloride in dioxane is added. The mixture is stirred for 30 minutes at room temperature and is then poured into ether. The solid is drained by suction, rinsed with pentane and dried in an oven under vacuum. 0.64 g of the expected product is finally obtained in the form of a white solid. Yield (dihydrochloride)= 91%. m.p.>260°C. $M+H^+$=578

$^1$H NMR (DMSO-d6+$D_2O$; 400 MHz): 8.9 (s, 1H); 7.6 (d, 1H); 6.95 (s, 1H); 6.85 (d, 1H); 4.8 (very broad s, 1H); 3.8 (s, 3H); 3.6 (m, 2H), 3.4 (m, 2H); 3.1 (m, 1H); 2.8-2.95 (m, 3H); 2.05 (m, 2H); 1.95 (m, 2H); 1.1 (very broad s, 6H).

EXAMPLE 18

7-Amino-2-[4-(4-ethylpiperazin-1-yl)-2-methoxyphenylamino]-8-(2-hydroxy-2-methylpropyl)-5-oxo-5,8-dihydropyrido[2,3-d]pyrimidine-6-carboxamide hydrochloride

18.1: 1-Ethyl-4-(3-methoxy-4-nitrophenyl)piperazine

A mixture of 3.42 g (20 mmol) of 4-fluoro-2-methoxy-1-nitrobenzene, 2.67 mL (21 mmol) of 1-ethylpiperazine and 5.14 mL (30 mmol) of diisopropylethylamine in 25 mL of acetonitrile is heated for 2.5 hours at 85°C. and then for 1 hour at 95°C., and is then stirred overnight while allowing to return to room temperature. The acetonitrile is evaporated off and the residue is then taken up in 50 mL of ether and 25 mL of water. The aqueous phase is extracted with ether. The organic phases are combined, dried over $Na_2SO_4$, filtered and concentrated under vacuum. The oil obtained is triturated in an ether/cyclohexane mixture (1/1) and the precipitate is isolated by filtration, rinsed with pentane and dried in an oven. 4.1 g of the expected product are finally obtained. Yield=77%.

18.2: 4-(4-Ethylpiperazin-1-yl)-2-methoxyphenylamine 4.05 g (15.27 mmol) of the product prepared in step 18.1 in 25 mL of an ethyl acetate/ethanol mixture (v/v=1/1) are placed in a hydrogenation autoclave, and 0.32 g of 10% palladium-on-charcoal is added, under an inert atmosphere. The mixture is stirred under a hydrogen pressure of 2.5 bar at room temperature for 2 hours. After filtering through thin glass fibre paper and evaporating under reduced pressure, 3.51 g of the expected product are obtained in the form of a violet solid, which is used as obtained in the following step. Yield=98%.

18.3: 7-Amino-2-[4-(4-ethylpiperazin-1-yl)-2-methoxyphenylamino]-8-(2-hydroxy-2-methylpropyl)-5-oxo-5,8-dihydropyrido[2,3-d]pyrimidine-6-carboxamide To a suspension of 1.0 g (3.21 mmol) of the product prepared in step 17.3 in 5 mL of anhydrous NMP are added 1.51 g (6.42 mmol) of the product prepared in step 18.2, and the reaction mixture is heated at 100°C. for 2 hours. It is allowed to cool to room temperature and is then diluted with aqueous $NaHCO_3$ solution. The mixture is stirred overnight and the precipitate is isolated by filtration and then dried in an oven. The residue is purified by chromatography on a column of silica, eluting with a dichloromethane/methanol gradient (100/0 to 95/5) containing traces of concentrated aqueous $NH_4OH$. After a final trituration in methanol and drying in an oven, 0.46 g of the expected product is obtained. Yield=28%.

18.4: 7-Amino-2-[4-(4-ethylpiperazin-1-yl)-2-methoxyphenylamino]-8-(2-hydroxy-2-methylpropyl)-5-oxo-5,8-dihydropyrido[2,3-d]pyrimidine-6-carboxamide hydrochloride A solution of 0.46 g (0.9 mmol) of the product prepared in step 18.3 in 13 mL of methanol is cooled on an ice bath, and 0.67 mL (2.69 mmol) of a 4N solution of hydrogen chloride in dioxane is added. The mixture is stirred for 30 minutes at room temperature and is then poured into ether. The solid is drained by suction, rinsed with pentane and dried in an oven under vacuum. 0.47 g of the expected product is finally obtained in the form of a yellow solid. Yield (dihydrochloride)=90%. m.p.=222°C. (decomposition). $M+H^+$=511.

$^1$H NMR (DMSO-$d_6$, 400 MHz): δ11.5 (broad s, 1H); 10.9 (broad s, 1H); 9.1 (broad s, 1H); 8.9 (broad s, 1H); 8.4 (broad s, 1H); 7.45 (d, 1H); 6.75 (d, 1H); 6.6 (dd, 1H); 4.8 (very broad s, 1H); 3.70-4.20 (s+m, 9H); 3.0-3.3 (m, 6H); 1.3 (t, 3H); 1.05 (very broad s, 6H).

EXAMPLE 19

7-Amino-2-[4-(4-ethylpiperid-1-yl)-2-methoxyphenylamino]-8-(2-hydroxy-2-methylpropyl)-5-oxo-5,8-dihydropyrido[2,3-d]pyrimidine-6-carboxamide hydrochloride

19.1: tert-Butyl 4-[4-(7-amino-6-carbamoyl-8-(2-hydroxy-2-methylpropyl)-5-oxo-5,8-dihydropyrido[2,3-d]pyrimidin-2-ylamino)-3-methoxyphenyl]piperidine-1-carboxylate A mixture of 2.0 g (6.42 mmol) of the product prepared in step 17.3 and 2.95 g (9.62 mmol) of the product prepared in step 4.3 in 18 mL of NMP is placed in a round-bottomed flask. The suspension is heated at 110°C. for 2 hours. 30 mL of water and then 5 mL of saturated aqueous NaHCO$_3$ are added and the precipitate formed is drained by suction and then dried in an oven. The crude solid is triturated in methanol and then dried in an oven. 2.38 g of the expected product are obtained in the form of a pink solid, which is used as obtained in the following step. Yield=64%.

19.2: 7-Amino-8-(2-hydroxy-2-methylpropyl)-2-(2-methoxy-4-piperid-4-yl-phenylamino)-5-oxo-5,8-dihydropyrido[2,3-d]pyrimidine-6-carboxamide hydrochloride A suspension of 2.28 g (3.92 mmol) of the product prepared in step 19.1 in 70 mL of dichloromethane is cooled on an ice-water bath, and 9.8 mL (39.20 mmol) of a 4N solution of hydrogen chloride in dioxane are added slowly. The mixture is stirred at room temperature for 1 hour, and ether is added. The solid is drained by suction, rinsed with pentane and dried in an oven. 2.2 g of the expected product are obtained in the form of a beige-coloured solid, which is used as obtained in the following step. Yield (dihydrochloride) =quantitative.

19.3: 7-Amino-8-(2-hydroxy-2-methylpropyl)-2-[4-(4-ethylpiperid-1-yl)-2-methoxyphenylamino]-5-oxo-5,8-dihydropyrido[2,3-d]pyrimidine-6-carboxamide 0.6 g (1.08 mmol) of the hydrochloride prepared in step 19.2 is suspended in 14 mL of 1,2-dichloroethane, and 0.56 mL (3.25 mmol) of diisopropylethylamine, 0.30 mL (5.41 mmol) of acetaldehyde and then, portionwise, 0.46 g (2.16 mmol) of sodium triacetoxyborohydride are added. The mixture is stirred for 2 hours and is poured into 0.25 N sodium hydroxide solution, and dichloromethane is added. After separation of the phases by settling, the aqueous phase is extracted with dichloromethane and the organic phases are combined, dried over Na$_2$SO$_4$, filtered and concentrated under vacuum. 0.58 g of a light-brown solid is recovered, and is purified by chromatography on a column of silica, eluting with a dichloromethane/methanol gradient (95/5 to 90/10). 0.26 g of the expected product is obtained in the form of a yellow solid. Yield=47%.

19.4: 7-Amino-8-(2-hydroxy-2-methylpropyl)-2-[4-(4-ethylpiperid-1-yl)-2-methoxyphenylamino]-5-oxo-5,8-dihydropyrido[2,3-d]pyrimidine-6-carboxamide hydrochloride To a solution of 0.25 g (0.50 mmol) of the product prepared in step 19.3 in 10 mL of a dichloromethane/methanol mixture (4/1) are added 2 mL (2 mmol) of 1.0 M hydrochloric ether. The mixture is stirred for 10 minutes at room temperature and is then diluted with ether. The precipitate is drained by suction, rinsed with ether and with pentane, and dried under vacuum. 0.28 g of the expected product is obtained in the form of a yellow solid. Yield (dihydrochloride)=96%. m.p.=200°C. (decomposition). M+H$^+$=510.

$^1$H NMR (DMSO-d$_6$, 400 MHz): δ11.5 (broad s, 1H); 10.4 (broad s, 1H); 9.1 (s, 1H); 8.95 (s, 1H); 8.45 (broad s, 1H); 7.6 (d, 1H); 7.0 (s, 1H); 6.85 (d, 1H); 4.8 (broad s, 2H); 3.85 (s, 3H); 3.6 (m, 2H); 3.1 (m, 2H); 3.05 (m, 2H); 2.85 (m, 1H); 2.1-2.2 (m, 4H); 1.3 (t, 3H); 1.1 (very broad s, 6H).

EXAMPLE 20

7-Amino-2-(2-methoxy-4-piperid-4-ylphenylamino)-5-oxo-8-phenyl-5,8-dihydropyrido[2,3-d]pyrimidine-6-carboxamide hydrochloride

20.1: Ethyl 2-methylsulfanyl-4-phenylamino-5-pyrimidinecarboxylate

To a solution of 5.0 g (21.49 mmol) of ethyl 4-chloro-2-methylsulfanyl-5-pyrimidinecarboxylate and 4.9 mL (53.72 mmol) of aniline in 75 mL of THF are added 7.49 mL (53.72 mmol) of triethylamine. The mixture is stirred at room temperature overnight. After evaporating off the THF, aqueous 1N HCl solution is added and the mixture is extracted with ethyl acetate. The organic phase is washed with saturated aqueous NaHCO$_3$ solution and then with NaCl solution. The organic phase is dried over MgSO$_4$. After filtering, the filtrate is concentrated to give 3.99 g of the expected product in the form of a beige-coloured solid, which is used as obtained in the following step. Yield=64%.

20.2: 2-Methylsulfanyl-4-phenylamino-5-pyrimidinecarboxylic acid

A mixture containing 3.98 g (13.75 mmol) of the product prepared in step 20.1, 34.4 mL (34.4 mmol) of 1N NaOH and 35 mL of ethanol is stirred at room temperature overnight. The ethanol is evaporated off under reduced pressure and the residue is diluted in 100 mL of water. 65 mL of aqueous 1N HCl solution are added and the precipitate formed is drained by suction. The solid is rinsed with water and dried under vacuum. 2.88 g of the expected product are obtained in the form of a beige-coloured solid. Yield=92%.

20.3: 2-Methylsulfanyl-4-phenylamino-5-pyrimidinecarboxylic acid fluoride

To a solution containing 2.88 g (11.02 mmol) of the product prepared in step 20.2 and 2.1 mL (15.0 mmol) of triethylamine in 55 mL of CH$_2$Cl$_2$ are added 1.40 mL (16.53 mmol) of cyanuric fluoride. The mixture is stirred at room temperature overnight and washed twice with 50 mL of ice-cold aqueous NaHCO$_3$ solution. The organic phase is washed with 75 mL of ice-cold water and dried over MgSO$_4$. The solvent is then evaporated off under reduced pressure. 3.0 g of the expected product are obtained in the form of a yellow solid. The yield is quantitative.

20.4: 7-Amino-2-methylsulfanyl-5-oxo-8-phenyl-5,8-dihydropyrido[2,3-d]pyrimidine-6-carboxamide To a solution of 1.0 g (11.96 mmol) of cyanoacetamide in 17 mL of anhydrous DMF, cooled to 0-5°C., is added 0.96 g (23.93 mmol) of 60% NaH. After the addition, the mixture is stirred for 10 minutes at room temperature and then cooled again on an ice-water bath, and a solution of 3.0 g the acid fluoride (11.39 mmol) prepared in step 20.3 in 17 mL of anhydrous DMF is added. The reaction mixture is stirred at room temperature overnight. The reaction mixture is cooled on an ice-water bath, and 0.48 g (11.96 mmol) of 60% NaH is added. The reaction mixture is stirred for 5 hours at room temperature and then poured into ice-cold aqueous 0.5 N HCl solution. The precipitate formed is isolated by filtration, rinsed with water, drained by suction and then dried in an oven. 3.44 g of a yellow solid mainly composed of the expected product in non-cyclized form are obtained.

The solid obtained above is taken up in 50 mL of n-butanol and the solution is refluxed overnight. After cooling to room temperature, the precipitate is isolated by filtration and dried in an oven. 1.69 g of the expected product are obtained in the form of a yellow solid. Yield=45%.

20.5: 7-Amino-2-methanesulfonyl-5-oxo-8-phenyl-5, 8-dihydropyrido[2,3-d]pyrimidine-6-carboxamide and 7-amino-2-methanesulfinyl-5-oxo-8-phenyl-5,8-dihydropyrido[2,3-d]pyrimidine-6-carboxamide To a suspension of 1.69 g (5.16 mmol) of the compound obtained in step 20.4 in 100 mL of chloroform are added 3.18 g (12.91 mmol) of meta-chloroperbenzoic acid. The mixture is stirred at room temperature for 24 hours, and 0.44 g (2.58 mmol) of meta-chloroperbenzoic acid is added. This mixture is stirred for 24 hours and the insoluble material is then separated out by filtration. The filtrate is concentrated under vacuum and then triturated in methanol and dried in an oven. 1.12 g of a pale yellow solid composed of a mixture of the expected sulfone and sulfoxide (about 80/20 by $^1$H NMR) are obtained.

20.6 tert-Butyl 4-[4-(7-amino-6-carbamoyl-5-oxo-8-phenyl-5,8-dihydropyrido[2,3-d]pyrimidin-2-ylamino)-3-methoxyphenyl]piperidine-1-carboxylate 0.4 g (1.11 mmol) of the mixture of sulfone and sulfoxide obtained in step 20.5 and 0.51 g (1.67 mmol) of the product prepared in step 16.3 are heated at 110°C. for 6 hours in 5 mL of NMP. Water is added and the solid is isolated by filtration and then dried in an oven. The 0.42 g of solid residue is purified by chromatography on a column of silica, eluting with a dichloromethane/methanol gradient (100/0 to 97/3). 0.16 g of expected product is obtained in the form of a light-brown solid. Yield=46%.

20.7: 7-Amino-2-(2-methoxy-4-piperid-4-ylphenylamino)-5-oxo-8-phenyl-5,8-dihydropyrido[2,3-d]pyrimidine-6-carboxamide hydrochloride A solution of 0.15 g (0.26 mmol) of the product prepared in step 20.6 in 4 mL of CH$_2$Cl$_2$ is cooled on an ice bath, and 0.99 mL (3.94 mmol) of a 4N solution of hydrogen chloride in dioxane is added. The mixture is stirred for 30 minutes at room temperature and then poured into ether. The solid is drained by suction, rinsed with pentane and dried in an oven under vacuum. 0.136 g of a pale pink solid is obtained, and is purified on a reverse phase to give, finally, 0.1 g of the expected product in the form of a yellow solid. Yield (dihydrochloride)=68%. m.p.=228°C. (decomposition). M+H$^+$=487.

$^1$H NMR (DMSO-d$_6$, 400 MHz): δ11.3 (broad s, 1H); 10.25 (broad s, 1H); 8.9-9.0 (s+m, 2H); 8.8 (m, 1H); 8.3 (s, 1H); 7.7 (m, 3H); 7.5 (m, 2H); 7.25 (broad s, 1H); 7.15 (m, 1H); 6.8 (s, 1H); 6.7 (broad s, 1H); 6.3 (m, 1H); 3.95 (s, 3H); 3.4 (m, 2H); 3.0 (m, 2H); 2.75 (m, 1H); 1.75-1.95 (m, 4H).

EXAMPLE 21

7-Amino-2-[4-(1-cyclopropylpiperid-4-yl)-2-methoxyphenylamino]-8-(2-hydroxy-2-methylpropyl)-5-oxo-5,8-dihydropyrido[2,3-d]pyrimidine-6-carboxamide hydrochloride 21.1: 7-Amino-2-[4-(1-cyclopropylpiperid-4-yl)-2-methoxyphenylamino]-8-(2-hydroxy-2-methylpropyl)-5-oxo-5,8-dihydropyrido[2,3-d]pyrimidine-6-carboxamide To a solution of 0.46 g (0.83 mmol) of the hydrochloride prepared in step 20.7 in 14 mL of anhydrous methanol are successively added 0.42 mL (2.48 mmol) of diisopropylethylamine, 0.47 mL (8.26 mmol) of acetic acid, finely ground 3 Å molecular sieves predried in a vacuum oven at 60°C. overnight, 0.75 mL (3.72 mmol) of (1-ethoxycyclopropoxy)trimethylsilane and 0.16 g (2.48 mmol) of sodium cyanoborohydride. The mixture is heated at 80°C. overnight, and is evaporated to dryness. The residue obtained is purified by chromatography on a column of silica, eluting with a dichloromethane/methanol gradient (96/4 to 90/10). 0.16 g of the expected product is finally obtained in the form of a white solid. Yield=37%.

21.2: 7-Amino-2-[4-(1-cyclopropylpiperid-4-yl)-2-methoxyphenylamino]-8-(2-hydroxy-2-methylpropyl)-5-oxo-5,8-dihydropyrido[2,3-d]pyrimidine-6-carboxamide hydrochloride To a suspension of 0.137 g (0.26 mmol) of the product prepared in step 21.1 in 5 mL of CH$_2$Cl$_2$ are added 1.05 mL (1.05 mmol) of 1.0 M hydrochloric ether. The mixture is stirred for 5 minutes at room temperature and then diluted with ether. The precipitate is drained by suction, rinsed with ether and with pentane, and dried under vacuum. 0.12 g of the expected product is obtained in the form of a yellow solid. Yield (dihydrochloride)=77%. m.p.=206°C. (decomposition). M+H$^+$=568

$^1$H NMR (DMSO-d$_6$, 400 MHz): δ11.5 (broad s, 1H); 10.7 (broad s, <1H); 10.6 (m, 1H); 9.1 (s, 1H); 8.9 (s, 1H); 8.4 (broad s, 1H); 7.6 (d, 1H); 7.0 (s, 1H); 6.85 (d, 1H); 4.8 (broad s, 2H); 3.8 (s, 3H); 3.6 (m, 2H); 3.2-3.4 (m, 3H); 3.05 (m, 1H); 2.8 (m, 2H); 2.15 (m, 2H); 1.95 (m, 2H); 1.15 (m, 2H); 1.0 (very broad s, 6H); 0.8 (m, 2H).

EXAMPLE 22

7-Amino-8-(2-hydroxy-2-methylpropyl)-2-{2-methoxy-4-[1-(2-methoxyethyl)piperid-4-yl]phenylamino}-5-oxo-5,8-dihydropyrido[2,3-d]pyrimidine-6-carboxamide hydrochloride 22.1: 7-Amino-2-{4-[1-(2-chloroethyl)piperid-4-yl]-2-methoxyphenylamino}-8-(2-hydroxy-2-methylpropyl)-5-oxo-5,8-dihydropyrido[2,3-d]pyrimidine-6-carboxamide To a suspension of 0.60 g (1.08 mmol) of the hydrochloride prepared in step 20.7 in 15 mL of anhydrous dichloroethane are successively added 0.56 mL (3.25 mmol) of diisopropylethylamine, 0.4 mL (5.41 mmol) of methoxyacetaldehyde (batch received from the company TCI Fine Chemicals) and 0.46 g of sodium triacetoxyborohydride. The mixture is stirred at room temperature for 2 hours and then diluted with 15 mL of a water/aqueous 1N NaOH mixture (2/1). The resulting mixture is stirred for 10 minutes and then diluted with ethyl acetate. The organic phase is dried over MgSO$_4$, filtered and concentrated under vacuum. 0.41 g of a yellow solid corresponding to 7-amino-2-{4-[1-(2-chloroethyl)piperid-4-yl]-2-methoxyphenylamino}-8-(2-hydroxy-2-methylpropyl)-5-oxo-5,8-dihydropyrido[2,3-d]pyrimidine-6-carboxamide, and not to the 7-amino-8-(2-hydroxy-2-methylpropyl)-2-{2-methoxy-4-[1-(2-methoxyethyl)piperid-4-yl]phenylamino}-5-oxo-5,8-dihydropyrido[2,3-d]pyrimidine-6-carboxamide initially expected, is obtained. Yield=69%.

22.2: 7-Amino-8-(2-hydroxy-2-methylpropyl)-2-{2-methoxy-4-[1-(2-methoxyethyl)piperid-4-yl]phenylamino}-5-oxo-5,8-dihydropyrido[2,3-d]pyrimidine-6-carboxamide To a suspension of 0.29 g (0.54 mmol) of the product prepared in step 22.1 in 9 mL of anhydrous methanol is added 0.37 g (2.68 mmol) of K$_2$CO$_3$, and the mixture is refluxed for 1 hour. It is evaporated to dryness and the residue is taken up in water and CH$_2$Cl$_2$. The organic phase is dried over MgSO$_4$, filtered and concentrated under vacuum. The crude product is purified by chromatography on a column of silica, eluting with a dichloromethane/methanol gradient (90/10). After triturating in methanol, 0.22 g of the expected product is finally obtained in the form of a yellow solid. Yield=78%.

22.3: 7-Amino-8-(2-hydroxy-2-methylpropyl)-2-{2-methoxy-4-[1-(2-methoxyethyl)piperid-4-yl]phenylamino}-5-oxo-5,8-dihydropyrido[2,3-d]pyrimidine-6-carboxamide To a suspension of 0.22 g (0.41 mmol) of the product prepared in step 22.2 in 8 mL of a CH$_2$Cl$_2$/methanol mixture (4/1) are added 1.63 mL (1.63 mmol) of 1.0 M hydrochloric ether. The mixture is stirred for 5 minutes at room temperature and is then diluted with ether. The precipitate is drained by suction, rinsed with ether and with pentane, and dried under vacuum. 0.23 of the expected product is obtained in the form of a pale yellow solid. Yield (dihydrochloride)=92%. m.p.=170°C. (decomposition). M+H$^+$=540
$^1$H NMR (DMSO-d$_6$, 400 MHz): δ11.5 (broad s, 1H); 10.35 (broad s, 1H); 10.6 (m, 1H); 9.05 (s, 1H); 8.9 (s, 1H); 8.4 (broad s, 1H); 7.6 (d, 1H); 7.0 (s, 1H); 6.8 (d, 1H); 4.75 (broad s, 2H); 3.7-3.85 (m+s, 5H); 3.6 (m, 2H); 3.2-3.4 (m+s, 5H); 3.1 (m, 2H); 2.85 (m, 1H); 2.15 (m, 2H); 2.0 (m, 2H); 1.0 (very broad s, 6H).

EXAMPLE 23

7-Amino-2-[2-methoxy-4-(1-methylpiperid-4-yl)phenylamino]-5-oxo-8-phenyl-5,8-dihydropyrido[2,3-d]pyrimidine-6-carboxamide hydrochloride 23.1: 7-Amino-2-[2-methoxy-4-(1-methylpiperid-4-yl)phenylamino]-5-oxo-8-phenyl-5,8-dihydropyrido[2,3-d]pyrimidine-6-carboxamide 0.2 g (0.55 mmol) of the mixture of the sulfone and sulfoxide obtained in step 20.5 and 0.24 g (1.11 mmol) of 2-methoxy-4-(1-methylpiperid-4-yl)phenylamine (prepared according to the method described in patent WO-09/024 824) are heated at 110°C. for 6 hours in 5 mL of NMP. The mixture is evaporated to dryness under vacuum and the residue is purified by chromatography on a column of silica, eluting with a dichloromethane/methanol gradient (100/0 to 95/5) containing traces of concentrated aqueous NH$_4$OH. 0.096 g of the expected product is obtained in the form of a beige-coloured solid. Yield=35%.

23.2: 7-Amino-2-[2-methoxy-4-(1-methylpiperid-4-yl)phenylamino]-5-oxo-8-phenyl-5,8-dihydropyrido[2,3-d]pyrimidine-6-carboxamide hydrochloride A solution of 0.065 g (0.13 mmol) of the product prepared in step 23.1 in 3 mL of CH$_2$Cl$_2$ is cooled on an ice bath, and 0.39 mL (0.39 mmol) of a 1M solution of hydrogen chloride in ether is added. The mixture is stirred for 10 minutes at room temperature and then poured into ether. The solid is drained by suction, rinsed with pentane and dried in an oven under vacuum. 0.059 g of the expected compound is obtained. Yield (dihydrochloride)=80%. m.p.=256°C. (decomposition). M+H$^+$=500
$^1$H NMR (DMSO-d$_6$, 400 MHz): δ11.3 (broad s, 1H); 10.25 (broad s, 1H); 9.0 (s, 1H); 8.35 (s, 1H); 7.7 (m, 3H); 7.5 (m, 2H); 7.25 (broad s, 1H); 7.15 (m, 1H); 6.8 (s, 1H); 6.7 (broad s, 1H); 6.3 (m, 1H); 3.8 (s, 3H); 3.45 (m, 2H); 3.0 (m, 2H); 2.8 (d, 3H); 2.7 (m, 1H); 1.85-2.05 (m, 4H).

EXAMPLE 24

7-Amino-2-[2-methoxy-4-(2-pyrrolidin-1-ylethyl)phenylamino]-5-oxo-8-phenyl-5,8-dihydropyrido[2,3-d]pyrimidine-6-carboxamide hydrochloride 24.1: 2-Methoxy-1-nitro-4-vinylbenzene 4.32 g (31.31 mmol) of potassium trifluorovinylborate and 3.12 mL (22.37 mmol) of triethylamine are added to a mixture of 5.19 g (22.37 mmol) of the product prepared in step 4.1 in 56 mL of n-propanol, under argon, and argon is bubbled through for 10 minutes. 0.36 g (0.45 mmol) of PdCl$_2$dppf.CH$_2$Cl$_2$ is added and the mixture is heated under argon at 100°C. for 3 hours. After cooling to room temperature, the reaction mixture is concentrated to dryness and then taken up in a dichloromethane/water mixture. After separation of the phases by settling, the organic phase is washed twice with water and once with saturated aqueous NaCl.

The organic phase is dried over Na$_2$SO$_4$, filtered and concentrated under vacuum. The residue obtained is purified by chromatography on a column of silica, eluting with a cyclohexane/ethyl acetate gradient (95/5 to 70/30). 3.1 g of the expected product are obtained in the form of a brown oil, which is used as obtained in the following step. Yield=77%.

24.2: 1-[2-(3-Methoxy-4-nitrophenyl)ethyl]pyrrolidine 3.07 g (17.17 mmol) of the product prepared in step 24.1 and 7.13 mL (85.84 mL) of pyrrolidine in 60 mL of anhydrous methanol are placed in a sealed tube. The mixture is heated under pressure at 100°C. for 4 hours. After cooling to room temperature, it is evaporated to dryness. The residue obtained is purified by chromatography on a column of silica, eluting with a dichloromethane/methanol gradient (100/0 to 90/10). 3.22 g of the expected product are obtained in the form of a yellow solid. Yield=75%.

24.3: 2-Methoxy-4-(2-pyrrolidin-1-ylethyl)phenylamine 0.41 g of palladium-on-charcoal and 4.1 g (64.32 mmol) of ammonium formate are added to a solution of 3.2 g (12.86 mmol) of the product prepared in step 24.2 in 120 mL of methanol, under argon, and the mixture is refluxed for 2 hours. After filtration, the filtrate is concentrated to dryness to give 2.6 g of the expected product in the form of a light-brown solid, which is used as obtained in the following step. Yield=92%.

24.4: 7-Amino-2-[2-methoxy-4-(2-pyrrolidin-1-yl-ethyl)phenylamino]-5-oxo-8-phenyl-5,8-dihydropy-rido[2,3-d]pyrimidine-6-carboxamide 0.2 g (0.55 mmol) of the mixture of sulfone and sulfoxide obtained in step 20.5 and 0.24 g (1.11 mmol) of the aniline prepared in step 24.3 are heated at 110°C. for 6 hours in 5 mL of NMP. The mixture is evaporated to dryness under vacuum and the residue is purified by chromatography on a column of silica, eluting with a dichloromethane/methanol gradient (100/0 to 90/10) containing traces of concentrated aqueous $NH_4OH$. 0.07 g of the expected product is obtained in the form of a glassy yellow solid. Yield=25%.

24.5: 7-Amino-2-[2-methoxy-4-(2-pyrrolidin-1-yl-ethyl)phenylamino]-5-oxo-8-phenyl-5,8-dihydropy-rido[2,3-d]pyrimidine-6-carboxamide hydrochloride A solution of 0.07 g (0.14 mmol) of the product prepared in step 24.4 in 3 mL of methanol is cooled on an ice bath, and 0.42 mL (0.42 mmol) of a 1M solution of hydrogen chloride in ether is added. The mixture is stirred for 10 minutes at room temperature and ether is then added. The solid is drained by suction, rinsed with pentane and dried in an oven under vacuum. 0.075 g of the expected compound is obtained. Yield (dihydrochloride)=93%.

$M+H^+=500$ $^1H$ NMR (DMSO-$d_6$+$D_2O$, 400 MHz, T=130°C.): 9.0 (s, 1H); 7.7 (m, 3H); 7.4 (m, 2H); 7.25 (d, 1H); 6.85 (s, 1H); 6.4 (d, 1H); 3.8 (s, 3H); 3.1-3.5 (m, 6H); 2.9 (m, 2H); 2.0 (m, 4H).

Table 1 below illustrates the chemical structures and physical properties of a number of compounds of formula (I) according to the invention. In this table:

Me and Et represent, respectively, methyl and ethyl groups, the "LC/UV/MS" column indicates, successively, the high-performance liquid chromatography analytical method used (A, B, C or D) and detailed below, the retention time (abbreviated as tr) of the compound, expressed in minutes, and the MH$^+$peak identified by mass spectrometry.

Method A:
Column: Kromasil C18, 50×2.1 mm, 3.5 µm
Solvent A: $H_2O$/ACN/TFA (1000/30/0.5); solvent B: ACN/TFA (1000/0.5); flow rate=0.5 mL/min
Gradient: 100/0 (0 min) to 0/100 (12 min) to 0/100 (15 min)
Detection: 220 nM
Ionization: ESI+

Method B:
Column: Gemini, 50×3 mm, 3 µm
Solvent A: $H_2O$+0.1% $HCO_2H$; solvent B: ACN+0.1% $HCO_2H$; flow rate=1 mL/min
Gradient: 95/5 (0 min) to 0/100 (5.5 min) to 0/100 (7.5 min)
Detection: 220 nM
Ionization: ESI+

Method C:
Column: Kromasil C18, 50×2.1 mm, 3.5 µm
Solvent A: $CH_3CO_2NH_4$ 5 mM; solvent B: ACN; flow rate=0.5 mL/min
Gradient: 100/0 (0 min) to 0/100 (13 min) to 0/100 (16 min)
Detection: 220 nM
Ionization: ESI+

Method D:
Column: Acquity BEH C18, 50×2.1 mm; 1.7 µm
Solvent A: $H_2O$+0.05% TFA; solvent B: ACN+0.035% TFA; flow rate=1 mL/min
Gradient: T0: 98% A; T1.6 to T2.1 min: 100% B; T2.5 to T3 min: 98% A
Detection: 220 nM
Ionization: ESI+ in the "Form" column, "-" indicates that the compound is in free base form, while "HCl" indicates that the compound is in hydrochloride form, in the "Compounds" column, "RAC" indicates that the compound is in the form of a racemic mixture, "¤" means that the data are not available.

TABLE 1

| No. | Compounds | Method | tr | MH$^+$ | Form |
|---|---|---|---|---|---|
| | | LC/UV/MS | | | |
| 1 | 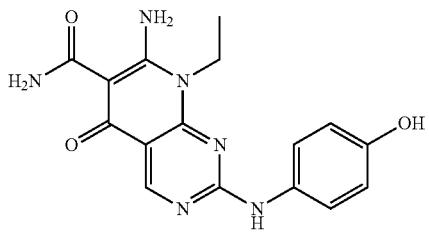 [SMILES: CCn1c(N)c(C(N)=O)c(=O)c2cnc(Nc3ccc(O)cc3)nc21] | A | ¤ | 341 | — |

TABLE 1-continued

| No. | Compounds | Method | tr | MH+ | Form |
|---|---|---|---|---|---|
| 2 | (structure) | A | 5.5 | 382 | — |
| 3 | (structure) | A | 5.7 | 422 | — |
| 4 | (structure) | A | 4.1 | 451 | — |
| 5 | (structure) | A | 9.8 | 409 | — |
| 6 | (structure) | A | 4.2 | 437 | — |
| 7 | (structure) | A | 4.4 | 477 | — |

TABLE 1-continued

| No. | Compounds | LC/UV/MS Method | tr | MH+ | Form |
|---|---|---|---|---|---|
| 8 | | B | 11.4 | 450 | — |
| 9 | | A | 5.9 | 472 | — |
| 10 | | B | 9.3 | 451 | — |
| 12 | | A | 5.8 | 376 | — |
| 13 | | A | 5.5 | 466 | — |
| 14 | | A | 6.7 | 409 | — |

TABLE 1-continued

| No. | Compounds | LC/UV/MS Method | tr | MH+ | Form |
|---|---|---|---|---|---|
| 15 | | A | 5.5 | 408 | — |
| 16 | | A | 4.5 | 376 | — |
| 17 | | A | 5.5 | 410 | — |
| 18 | | A | 5.8 | 383 | — |
| 19 | | A | 5.1 | 359 | — |
| 20 | | A | 6.6 | 371 | — |

TABLE 1-continued

| No. | Compounds | LC/UV/MS Method | tr | MH+ | Form |
|---|---|---|---|---|---|
| 21 | (structure) | B | 4.3 | 410 | — |
| 22 | (structure) | B | 6.1 | 343 | — |
| 25 | (structure) | A | 3.9 | 557 | HCl |
| 26 | (structure) | A | 3.9 | 589 | HCl |
| 27 | (structure) | C | 0.8 | 543 | HCl |

TABLE 1-continued

| No. | Compounds | LC/UV/MS Method | tr | MH+ | Form |
|---|---|---|---|---|---|
| 28 | | C | 0.7 | 485 | HCl |
| 29 | | C | 0.76 | 478 | HCl |
| 30 | | C | 0.6 | 438 | HCl |
| 31 | | C | 0.78 | 513 | HCl |
| 32 | | C | 0.7 | 523 | HCl |

TABLE 1-continued

| No. | Compounds | LC/UV/MS Method | tr | MH+ | Form |
|---|---|---|---|---|---|
| 33 | | D | 0.75 | 515 | HCl |
| 34 | | C | 0.7 | 479 | HCl |
| 35 | | C | 0.8 | 534 | HCl |
| 36 | | C | 0.71 | 471 | HCl |
| 37 | | D | 0.80 | 505 | HCl |

TABLE 1-continued

| No. | Compounds | Method | tr | MH+ | Form |
|---|---|---|---|---|---|
| 38 | | C | 2.98 | 424 | — |
| 39 | | D | 0.74 | 505 | HCl |
| 40 | | D | 0.69 | 455 | HCl |
| 42 | | D | 0.69 | 467 | HCl |
| 43 | | D | 0.70 | 452 | HCl |
| 44 | | D | 0.67 | 449 | HCl |

LC/UV/MS

TABLE 1-continued

| No. | Compounds | LC/UV/MS Method | tr | MH+ | Form |
|---|---|---|---|---|---|
| 45 | | D | 0.67 | 451 | HCl |
| 46 | | D | 0.68 | 451 | HCl |
| 48 | | D | 0.87 | 504 | HCl |
| 49 | | D | 0.71 | 452 | HCl |
| 50 | | D | 0.75 | 490 | HCl |

TABLE 1-continued

| No. | Compounds | LC/UV/MS Method | tr | MH+ | Form |
|---|---|---|---|---|---|
| 51 | | D | 0.58 | 424 | HCl |
| 52 | | D | 0.66 | 466 | HCl |
| 53 | | D | 0.59 | 426 | — |
| 54 | | D | 0.62 | 452 | HCl |
| 55 | | D | 0.69 | 369 | — |
| 56 | | D | 0.55 | 394 | — |

TABLE 1-continued

| No. | Compounds | LC/UV/MS Method | tr | MH+ | Form |
|---|---|---|---|---|---|
| 57 | | D | 0.60 | 486 | HCl |
| 58 | | D | 0.57 | 465 | HCl |
| 59 | | D | 0.71 | 504 | HCl |
| 60 | | D | 0.63 | 436 | HCl |
| 61 | | D | 0.70 | 511 | HCl |
| 62 | | D | 0.60 | 416 | HCl |

TABLE 1-continued

| No. | Compounds | LC/UV/MS Method | tr | MH+ | Form |
|---|---|---|---|---|---|
| 63 | | D | 0.64 | 458 | HCl |
| 64 | | C | 0.59 | 394 | HCl |
| 65 | | D | 0.64 | 436 | HCl |
| 66 | | D | 0.65 | 492 | HCl |
| 67 | | D | 0.65 | 472 | HCl |
| 68 | | D | 0.59 | 408 | HCl |

TABLE 1-continued

| No. | Compounds | LC/UV/MS Method | tr | MH+ | Form |
|---|---|---|---|---|---|
| 69 | | D | 0.64 | 472 | HCl |
| 70 | | D | 0.61 | 482 | HCl |
| 71 | | D | 0.62 | 422 | HCl |
| 72 | | D | 0.59 | 396 | — |
| 73 | | D | 0.62 | 408 | HCl |
| 74 | | D | 0.56 | 380 | HCl |

TABLE 1-continued

| No. | Compounds | LC/UV/MS Method | tr | MH+ | Form |
|---|---|---|---|---|---|
| 75 | | D | 2.52 | 380 | HCl |
| 76 | | D | 0.62 | 438 | HCl |
| 77 | | D | 0.59 | 454 | HCl |
| 78 | | D | 0.59 | 382 | HCl |
| 79 | | D | 0.57 | 477 | HCl |
| 80 | | D | 0.61 | 424 | HCl |

TABLE 1-continued

| No. | Compounds | Method | tr | MH+ | Form |
|---|---|---|---|---|---|
| 81 | | D | 0.55 | 439 | HCl |
| 82 | | D | 0.59 | 438 | HCl |
| 83 | | D | 0.56 | 382 | HCl |
| 84 | | D | 0.63 | 436 | HCl |
| 85 | | D | 0.60 | 408 | HCl |
| 86 | | D | 0.66 | 471 | HCl |

TABLE 1-continued

| No. | Compounds | Method | tr | MH+ | Form |
|---|---|---|---|---|---|
| 87 | | D | 0.67 | 496 | HCl |
| 88 | | D | 0.72 | 504 | HCl |
| 89 | RAC | D | 0.66 | 466 | HCl |
| 90 | | D | 0.61 | 410 | HCl |
| 91 | | D | 0.60 | 426 | HCl |

TABLE 1-continued
| No. | Compounds | Method | tr | MH+ | Form |
|---|---|---|---|---|---|
| 92 | 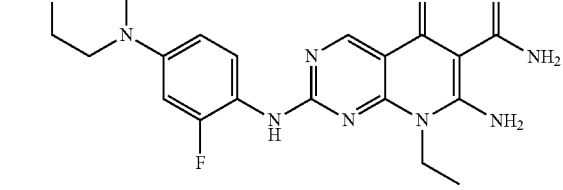 | D | 0.67 | 455 | HCl |
| 93 | 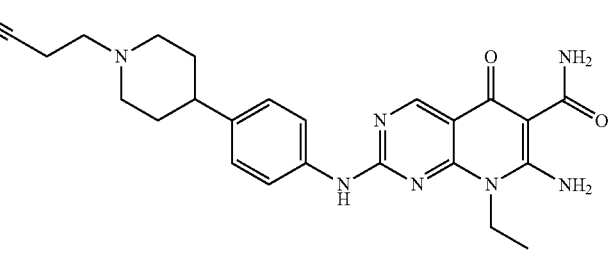 | D | 0.68 | 461 | HCl |
| 94 | 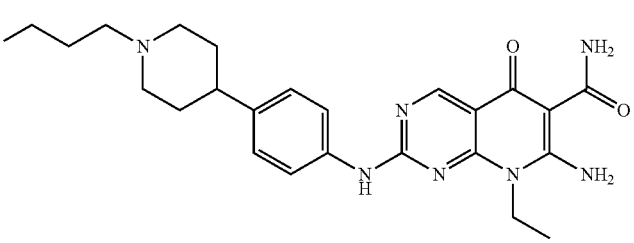 | D | 0.7 | 468 | HCl |
| 95 | 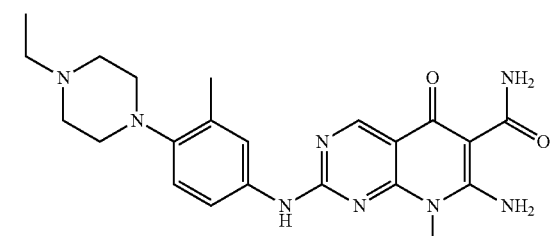 | D | 0.7 | 451 | HCl |
| 96 | 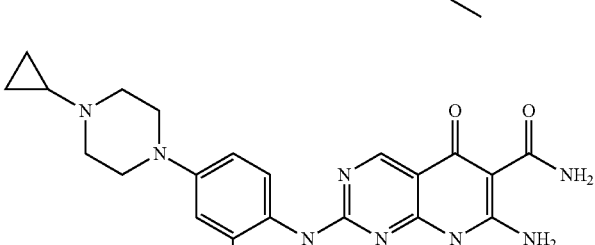 | D | 0.72 | 477 | HCl |
| 97 | 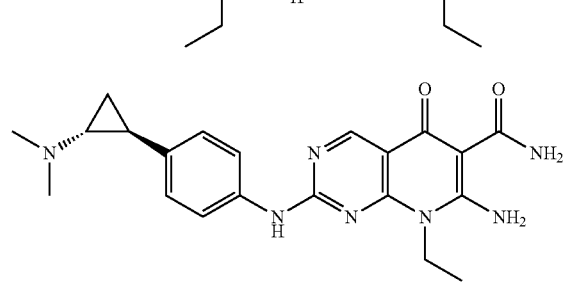 | D | 0.67 | 408 | HCl |

TABLE 1-continued

| No. | Compounds | LC/UV/MS Method | tr | MH+ | Form |
|---|---|---|---|---|---|
| 98 | | D | 0.75 | 497 | HCl |
| 99 | | D | 0.74 | 497 | HCl |
| 100 | | D | 0.76 | 493 | HCl |
| 101 | | B | 6.3 | 343 | — |
| 102 | | B | 6.2 | 355 | HCl |
| 103 | | B | 6.2 | 369 | HCl |

TABLE 1-continued

| No. | Compounds | LC/UV/MS Method | tr | MH+ | Form |
|---|---|---|---|---|---|
| 104 | | B | 5.2 | 408 | HCl |
| 105 | | C | 4.4 | 548 | HCl |
| 106 | | D | 0.83 | 562 | HCl |
| 107 | | D | 0.8 | 560 | HCl |
| 108 | | D | 0.77 | 564 | HCl |

TABLE 1-continued
| No. | Compounds | LC/UV/MS Method | tr | MH+ | Form |
|---|---|---|---|---|---|
| 109 | 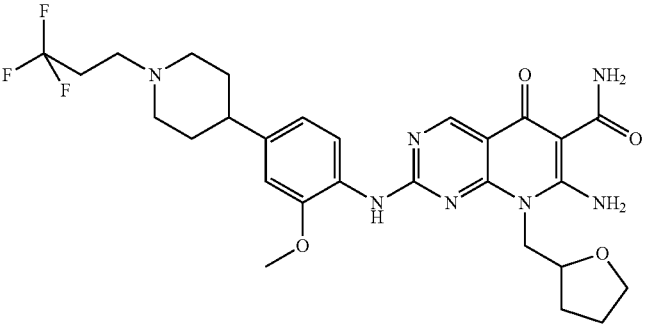 [SMILES: COc1cc(C2CCN(CCC(F)(F)F)CC2)ccc1Nc1ncc2c(=O)c(C(N)=O)c(N)n(CC3CCCO3)c2n1] | D | 0.9 | 590 | HCl |
| 110 | 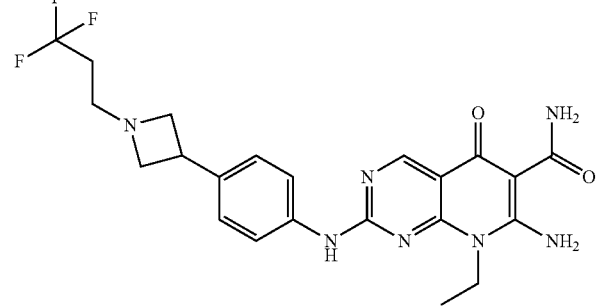 | D | 0.8 | 476 | HCl |
| 111 | 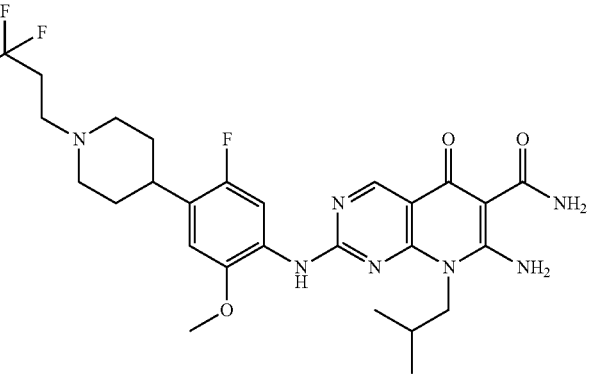 | D | 0.9 | 580 | HCl |
| 112 | 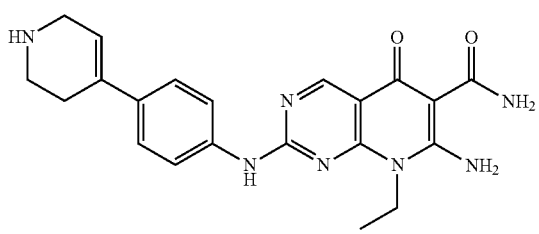 [SMILES: CCn1c(N)c(C(N)=O)c(=O)c2cnc(Nc3ccc(C4=CCNCC4)cc3)nc21] | D | 0.7 | 406 | HCl |

TABLE 1-continued

| No. | Compounds | LC/UV/MS Method | tr | MH+ | Form |
|---|---|---|---|---|---|
| 113 | | D | 0.7 | 487 | HCl |
| 114 | | D | 0.6 | 455 | HCl |
| 115 | | D | 604 | 0.78 | HCl |
| 116 | | D | 604 | 0.73 | HCl |

TABLE 1-continued

| No. | Compounds | LC/UV/MS Method | tr | MH+ | Form |
|---|---|---|---|---|---|
| 117 | | D | 482 | 0.66 | — |
| 118 | | D | 592 | 0.71 | HCl |
| 119 | | D | 426 | 0.55 | HCl |
| 120 | | D | 466 | 0.63 | HCl |
| 121 | | D | 454 | 0.64 | HCl |

TABLE 1-continued
| No. | Compounds | LC/UV/MS Method | tr | MH+ | Form |
|---|---|---|---|---|---|
| 122 | 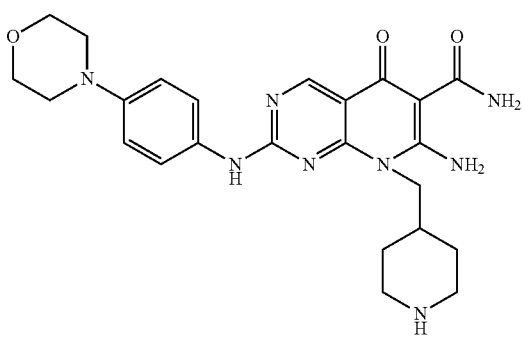 [SMILES: NC(=O)c1c(N)n(CC2CCNCC2)c2nc(Nc3ccc(N4CCOCC4)cc3)ncc2c1=O] | D | 480 | 0.67 | HCl |
| 123 | 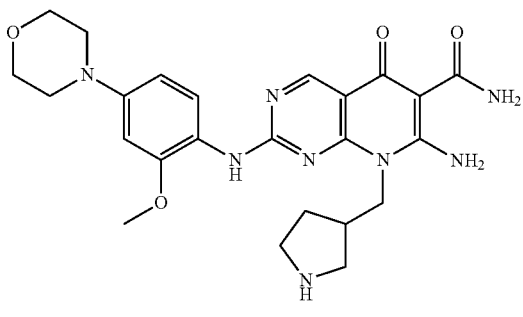 [SMILES: COc1cc(N2CCOCC2)ccc1Nc1ncc2c(=O)c(C(N)=O)c(N)n(CC3CCNC3)c2n1] | D | 496 | 0.67 | HCl |
| 124 | 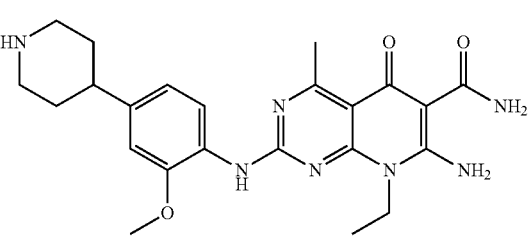 [SMILES: CCn1c(N)c(C(N)=O)c(=O)c2c(C)nc(Nc3ccc(C4CCNCC4)cc3OC)nc21] | D | 458 | 0.77 | HCl |
| 125 | 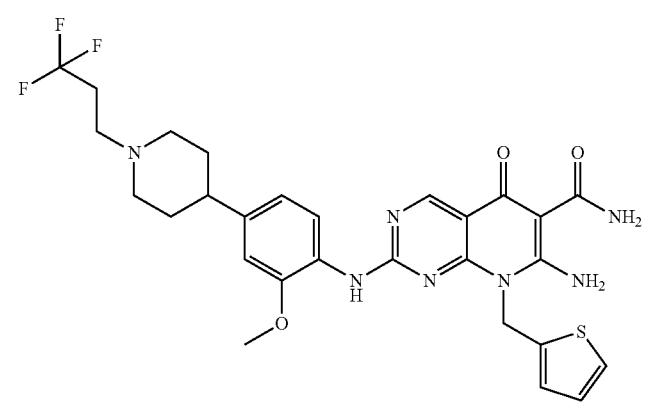 [SMILES: COc1cc(C2CCN(CCC(F)(F)F)CC2)ccc1Nc1ncc2c(=O)c(C(N)=O)c(N)n(Cc3cccs3)c2n1] | D | 603 | 0.88 | HCl |

TABLE 1-continued

| No. | Compounds | LC/UV/MS Method | tr | MH+ | Form |
|---|---|---|---|---|---|
| 126 | | D | 552 | 0.73 | HCl |
| 127 | | D | 466 | 0.92 | HCl |
| 128 | | B | 533 | 0.88 | HCl |
| 129 | | D | 511 | 0.63 | HCl |

TABLE 1-continued

| No. | Compounds | LC/UV/MS Method | tr | MH+ | Form |
|---|---|---|---|---|---|
| 130 | | D | 578 | 0.74 | HCl |
| 131 | | D | 510 | 0.67 | HCl |
| 132 | | D | 522 | 1.89 | HCl |
| 133 | | D | 540 | 0.68 | HCl |

TABLE 1-continued

| No. | Compounds | LC/UV/MS Method | tr | MH+ | Form |
|---|---|---|---|---|---|
| 134 | | D | 500 | 0.70 | HCl |
| 135 | | D | 504 | 0.70 | HCl |
| 136 | | D | 504 | 0.70 | HCl |
| 137 | | C | 500 | 0.93 | HCl |
| 138 | | C | 516 | 0.87 | HCl |

TABLE 1-continued
| No. | Compounds | LC/UV/MS Method | tr | MH+ | Form |
|---|---|---|---|---|---|
| 139 | 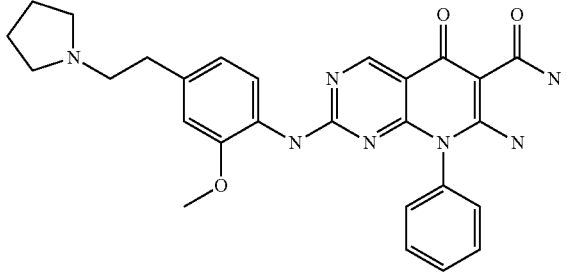 [SMILES: COc1cc(CCN2CCCC2)ccc1Nc1ncc2c(=O)c(C(N)=O)c(N)n(-c3ccccc3)c2n1] | D | 500 | 0.72 | HCl |
| 140 | 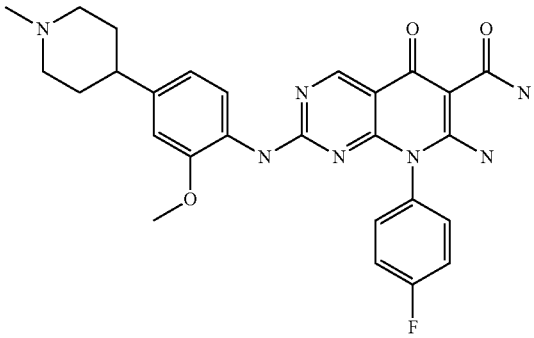 [SMILES: COc1cc(C2CCN(C)CC2)ccc1Nc1ncc2c(=O)c(C(N)=O)c(N)n(-c3ccc(F)cc3)c2n1] | D | 518 | 1.29 | HCl |
| 141 | 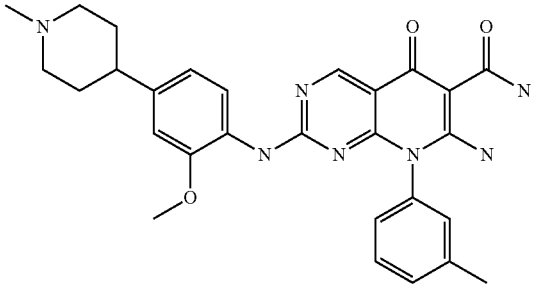 [SMILES: COc1cc(C2CCN(C)CC2)ccc1Nc1ncc2c(=O)c(C(N)=O)c(N)n(-c3cccc(C)c3)c2n1] | C | 514 | 0.87 | HCl |
| 142 | 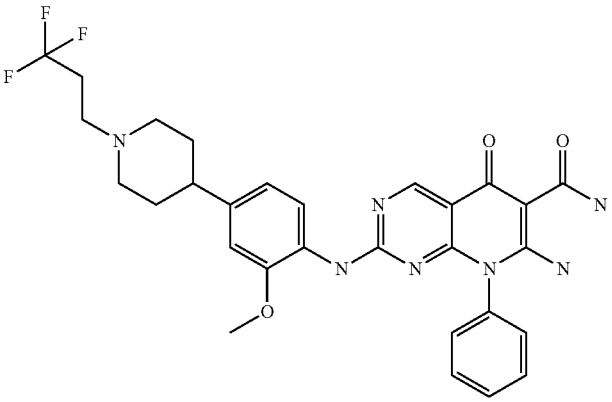 [SMILES: COc1cc(C2CCN(CCC(F)(F)F)CC2)ccc1Nc1ncc2c(=O)c(C(N)=O)c(N)n(-c3ccccc3)c2n1] | C | 582 | 1.03 | HCl |

TABLE 1-continued

| No. | Compounds | LC/UV/MS Method | tr | MH+ | Form |
|---|---|---|---|---|---|
| 143 | | C | 515 | 0.86 | HCl |

The compounds according to the invention underwent pharmacological trials to determine their inhibitory effect on CaMKII, on the δisoform.

The tests consisted in measuring the in vitro activity of the compounds of the invention on CaMKIIδ.

The compounds according to the invention were tested in vitro for their capacity to inhibit the kinase function of calcium/calmodulin-dependent protein kinase II delta (CaMKIIδ). CaMKIIδis an intracellular serine/threonine kinase. It has an enzymatic domain that is capable of using ATP to autophosphorylate. Its kinase function allows it to use ATP to phosphorylate its substrates on the serines and/or threonines. Several enzymatic and cellular tests are used to evaluate the activity of the products with respect to the kinase function of CaMKIIδ.

The kinase activity of CaMKIIδis evaluated by means of a radioactive test on the recombinant CaMKIIδenzyme. The amount of ATP-γ33P incorporated into the specific substrate Autocamtide-2 during its phosphorylation by CaMKIIδis measured. The effect of the products is quantified by the concentration of product that inhibits the total activity of CaMKIIδby 50% (50% inhibitory concentration=$IC_{50}$). For the determination of the $IC_{50}$ values, the product is diluted in 100% of DMSO to obtain a 10 mM stock solution. The concentration range tested during the radioactive test ranges from 3 to 10 000 nM with a final concentration in the test of 1% DMSO. This concentration range may, for the most powerful compounds, be extended to 0.1 nM. On the day of the operation, 5 μl of the compounds are deposited in each well of a 96-well plate at 10 times the concentration of that to be tested. Each concentration is tested in duplicate on the same plate. The negative controls (0% activity) and positive controls (100% activity) receive 5 μL of 10% DMSO solution. A reaction premix containing the 1×kinase buffer and an ATP-$MgCl_2$ mixture is prepared. Extemporaneously, a mixture containing the substrate Autocamtide-2 (100 μM) with calmodulin and calcium, and the solution of enzyme CaMKIIδ, is added to the premix. 45 μL of this mixture are immediately deposited per well. The final concentrations in the 50 μL final volume are as follows: compound 1X, 0.37 nM of CaMKIIδ (Invitrogen reference PV3373), 10 μM of ATP (1 μCi per well), 100 μM of Autocamtide-2, 8 pg/mL of calmodulin, 15 mM $MgCl_2$, 400 μM $CaCl_2$, 10 mM β-glycerophosphate, and 1% of DMSO. Two negative controls are prepared on each plate, a first without enzyme CaMKIIδ, and a second without substrate Autocamtide-2; these two elements are replaced with water. The plate is then incubated for two hours at 37°C. with gentle shaking. The reaction is stopped by adding 20 μL per well of $H_3PO_4$ solution. The 50 μL of each well are transferred onto a Whatman P81 filter. After rinsing twice with $H_3PO_4$ (150 μl/well per wash), followed by two rinses with 150 μL of $H_2O$, 50 μL of scintillant are added per well. The amount of phosphorylated substrate is detected by means of a liquid scintillation counter.

The inhibitory activity toward CaMKIIδis given by the concentration that inhibits 50% of the activity of CaMKIIδ. The $IC_{50}$ values are generally between 10 μM and $10^{-5}$ μM. In the table below, the $IC_{50}$ values measured for several compounds (I) of the invention are presented as examples.

| Compound No. | $IC_{50}$ (nM) |
|---|---|
| compound 32 | 2 |
| compound 61 | 8 |
| compound 29 | 17 |
| compound 35 | 22 |
| compound 75 | 37 |
| compound 113 | 39 |
| compound 114 | 57 |
| compound 76 | 118 |
| compound 52 | 139 |
| compound 4 | 260 |
| compound 78 | 268 |
| compound 96 | 396 |
| compound 60 | 663 |

It is thus seen that the compounds according to the invention have inhibitory activity on CaMKIIδ.

The compounds according to the invention may thus be used for the preparation of medicaments that inhibit CaMKII and in particular medicaments that inhibit CaMKIIδ.

Thus, according to another of its aspects, a subject of the invention is medicaments that comprise a compound of formula (I), or an addition salt thereof with a pharmaceutically acceptable acid, or alternatively a hydrate or a solvate of the compound of formula (I).

These medicaments find their use in therapy, especially in the treatment and/or prevention of pathologies in which CaMKII is involved, and in particular in which CaMKIIδis involved.

According to another of its aspects, the present invention also relates to the use of a compound of formula (I) for the preparation of a medicament for preventing and/or treating cardiovascular pathologies including myocardial infarction, ventricular hypertrophy, myocardial fibrosis, cardiac insufficiency, cardiac arrhythmia and restenosis, and also pathologies associated with the development of fibrosis, including hepatic, pancreatic, renal, pulmonary, cutaneous, intestinal and ocular fibrosis. A compound of formula (I) may also be used in the treatment and/or prevention of other renal pathologies, such as acute renal insufficiency, and also in the treatment of atherosclerosis, rheumatoid arthritis, Parkinson's disease and strokes.

According to another of its aspects, the present invention relates to pharmaceutical compositions comprising, as active principle, a compound according to the invention. These pharmaceutical compositions contain an effective dose of at least one compound according to the invention, or a pharmaceutically acceptable salt, a hydrate or a solvate of the said compound, and also at least one pharmaceutically acceptable excipient.

The said excipients are chosen, according to the pharmaceutical form and the desired mode of administration, from the usual excipients known to those skilled in the art.

In the pharmaceutical compositions of the present invention for oral, sublingual, subcutaneous, intramuscular, intravenous, topical, local, intratracheal, intranasal, transdermal or rectal administration, the active principle of formula (I) above, or the possible salt, solvate or hydrate thereof, may be administered in unit administration form, as a mixture with standard pharmaceutical excipients, to man and animals for the prophylaxis or treatment of the above disorders or diseases.

The appropriate unit administration forms include oral forms such as tablets, soft or hard gel capsules, powders, granules and oral solutions or suspensions, sublingual, buccal, intratracheal, intraocular, intranasal or inhalation administration forms, topical, transdermal, subcutaneous, intramuscular or intravenous administration forms, rectal administration forms and implants. For topical application, the compounds according to the invention may be used in creams, gels, ointments or lotions.

By way of example, a unit administration form of a compound according to the invention in tablet form may comprise the following components:

| | |
|---|---|
| Compound according to the invention | 50.0 mg |
| Mannitol | 223.75 mg |
| Sodium croscarmellose | 6.0 mg |
| Corn starch | 15.0 mg |
| Hydroxypropylmethylcellulose | 2.25 mg |
| Magnesium stearate | 3.0 mg |

There may be particular cases in which higher or lower dosages are appropriate; such dosages are not outside the scope of the invention. According to the usual practice, the dosage that is appropriate for each patient is determined by the doctor according to the mode of administration, and the weight and response of the said patient.

According to another of its aspects, the present invention also relates to a method for treating and/or preventing the pathologies indicated above, which comprises the administration to a patient of an effective dose of a compound according to the invention, or a pharmaceutically acceptable salt or hydrate or solvate thereof.

We claim:
1. A compound of formula (I)

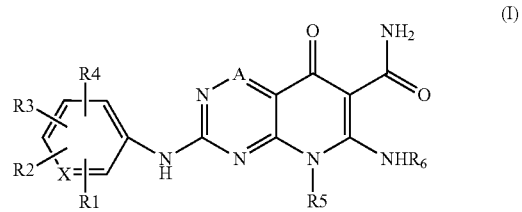

wherein:
A represents CH or C(alkyl);
X represents CH, C(alkyl) or N;
R1, R2, R3 and R4, which may be identical or different, represent, independently of each other:
a hydrogen atom;
a linear, branched or cyclic alkyl, optionally substituted with one or more of the following:
halogen atoms;
—$OR_9$;
—$NR_9R'_9$,
—CN;
—$C(O)OR_9$;
—$C(O)NR_9R_9'$;
—$S(O)_pR_{10}$,
—$S(O)_2NR_9R'_9$;
in which $R_9$, $R'_9$, $R_{10}$ and p are as defined below
a group —$S(O)_pR_{10}$ in which p and $R_{10}$ are as defined below;
a group —$OR_{10}$ in which $R_{10}$ is as defined below;
a halogen atom;
a group —$N(R_{11})C(O)R_{12}$, in which
(i) $R_{11}$ and $R_{12}$ represent, independently of each other, a hydrogen atom or a linear, branched or cyclic alkyl, optionally substituted with one or more substituents chosen from halogen atoms, groups —$OR_9$ and groups —$NR_9R'_9$, or
(ii) $R_{11}$ and $R_{12}$ form, together with the atoms to which they are attached, a heterocycloalkyl, so as to form a lactam;
a group —$N(R_{14})$—$CH_2$—$C(O)NR_{15}R_9$, in which $R_{14}$ and $R_{15}$ form, together with the atoms to which they are attached, a heterocycloalkyl, so as to form a piperazinone and in which $R_9$ is as defined below;
a group —$C(O)NR_{16}R_{17}$ with $R_{16}$ and $R_{17}$ form, together with the nitrogen atom to which they are attached, a heterocycloalkyl,
a group -T-U, in which:
T represents:
a single bond,
a linear or branched alkylene group;
a group —C(O)—,
a group —$S(O)_p$—in which p is as defined below, or
a group —O—$(CH_2)_n$—in which n is as defined below,
with U representing a heterocycle comprising one or more heteroatoms chosen from N, O and S(O)p, in which p is as defined below, the said heterocycle being saturated, unsaturated or aromatic, optionally mono- or di- or polysubstituted with one, two or several substituents chosen from:
groups —$OR_7$, in which $R_7$ is as defined below,
halogen atoms, groups —C(O)R$_7$ in which R$_7$ is as defined below, linear, branched or cyclic alkyls, optionally substituted with one or more substituents chosen from halogen atoms, groups —OR$_{10}$, groups —NR$_9$R'$_9$ and the group —CN, in which R$_9$, R'$_9$ and R$_{10}$ are as defined below; and saturated, unsaturated or aromatic heterocycles, optionally substituted with one or more substituents chosen from halogen atoms, groups —OR$_9$, groups —NR$_9$R'$_9$ and groups alkyl, the said alkyl groups being optionally substituted with one or more halogen atoms; or T represents:
 a group —C(O)—;
 a group —S(O)$_2$—; or
 a group —O—(C2-C3)alkylene-;
 with U representing a group —NR$_9$R'$_9$ in which R$_9$ and R'$_9$ are as defined below; or T represents:
 a group —C(O)—; or
 a group —O—(C2-C3)alkylene-;
 with U representing a group —OR$_9$, in which R$_9$ is as defined below; or T represents:
 a linear or branched alkylene group; or
 a group —O—(C2-C3)alkylene-;
 with U representing a group —NR$_8$R$_9$ in which R$_9$ and R$_8$ are as defined below;

or alternatively two adjacent groups chosen from R1, R2, R3 and R4 are linked and form, with the two carbons that bear them, a saturated, unsaturated or aromatic heterocycle, optionally substituted with one or more linear, branched or cyclic alkyl groups, the said alkyl groups being optionally substituted with one or more substituents chosen from halogen atoms, groups —OR$_{10}$, and groups —NR$_9$R'$_9$, in which R$_9$, R'$_9$ and R$_{10}$ are as defined below, the said heterocycle being fused with the aromatic ring, R5 represents:
 a linear or branched alkyl, optionally substituted with one or more substituents chosen from halogen atoms, groups —OR$_9$, groups —NR$_9$R'$_9$, the group —CN, groups —C(O)NR$_9$R$_9$·, groups —S(O)$_p$R$_{10}$ and cycloalkyl groups optionally substituted with a group —NR$_9$R'$_9$, in which R$_9$, R'$_9$, R$_{10}$ and p are as defined below,
 a cycloalkyl group, optionally substituted with a group —NR$_9$R'$_9$, in which R$_9$ and R'$_9$ are as defined below,
 an alkoxy group —OR$_9$, in which R$_9$ is as defined below,
 an aryl optionally substituted with one or more substituents chosen from groups (C1-C3)alkyl, halogen atoms and groups —O—(C1-C3)alkyl, or
 a group —(CH$_2$)$_t$—R$_{13}$, in which R$_{13}$ and t are as defined below, R$_6$ represents a hydrogen atom or a linear, branched or cyclic alkyl, and in which:

R$_7$ represents a hydrogen atom or a linear, branched or cyclic alkyl, optionally substituted with one or more of the following substituents chosen from halogen atoms, groups —OR$_9$ and groups —NR$_9$R'$_9$ with R$_9$ and R'$_9$ as defined below;

R$_8$ represents a heteroaryl group;

R$_9$ and R'$_9$ represent, independently of each other, a hydrogen atom or a linear, branched or cyclic alkyl;

R$_{10}$ represents a hydrogen atom or a linear, branched or cyclic alkyl optionally substituted with one or more halogen atoms, R$_{13}$ represents a heteroaryl or a heterocycloalkyl optionally substituted with one or more substituents chosen from linear, branched or cyclic alkyls, it being understood that when the said heterocycloalkyl comprises at least one nitrogen atom, this atom may optionally bear the said substituent, t represents 1 or 2, n represents 0, 1, 2 or 3, and p represents 0, 1 or 2, or an addition salt with an acid or a base thereof, or a hydrate or solvate thereof.

2. The compound according to claim 1, wherein:

A represents CH or C(CH$_3$); and

X represents CH or N;

or an addition salt with an acid or a base thereof, or a hydrate or solvate thereof.

3. The compound having the formula,

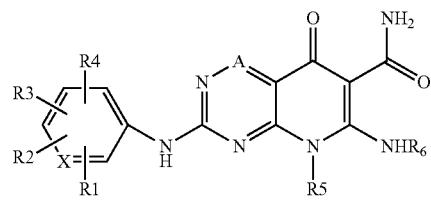

wherein:

A represents CH,

X represents CH, C(alkyl) or N,

R1, R2, R3 and R4, which may be identical or different, represent, independently of each other:

a hydrogen atom, a linear, branched or cyclic alkyl, optionally substituted with one or more of the following halogen atoms, a group —OR$_9$ or —NR$_9$R'$_9$, in which R$_9$ and R'$_9$ represent, independently of each other, a hydrogen atom or a linear, branched or cyclic alkyl, a group —S(O)$_p$R$_{10}$ or a group —OR$_{10}$, in which R$_{10}$ represents a hydrogen atom or a linear, branched or cyclic alkyl optionally substituted with one or more halogen atoms, and p represents 0, 1 or 2, a halogen atom, a group —N(R$_{11}$)C(O)R$_{12}$, in which R$_{11}$ and R$_{12}$ represent, independently of each other, a hydrogen atom or a linear, branched or cyclic alkyl or R$_{11}$ and R$_{12}$ form, together with the atoms to which they are attached, a heterocycloalkyl, so as to form a lactam;

a group -T-U, in which
  T represents:
   a single bond,
   a linear or branched alkylene group,
   a group —C(O)—,
   a group —S(O)$_p$, in which p represents 0, 1 or 2,
   A group —O—(CH$_2$)$_n$— in which n represents 0, 1, 2 or 3,
  and U represents a heterocycle comprising one or more heteroatoms chosen from N, O and S(O)p in which p represents 0, 1 or 2, the said heterocycle being of the formula:

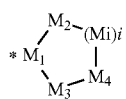

in which
* represents the position of attachment of U to T;
M1 represents a C or N atom;
M2 and M3, which may be identical or different, represent a C, N or O atom or S(O)p in which p=0, 1 or 2;
M4 represents a C, C(=O), N, O or S(O)p atom in which p=0, 1 or 2;
each of the Mi, which may be identical or different, represent a C, C(=O), N, O or S(O)p atom in which p=0, 1 or 2;
i=0, 1, 2 or 3;
it being understood that each of the $M_1$, $M_2$, $M_3$, $M_4$ or Mi may be optionally substituted if a valency is available and/or the adjacent $M_1$, $M_2$, $M_3$, $M_4$ or Mi may be attached via a double bond, where appropriate;
the said heterocycle U being saturated, unsaturated or aromatic, optionally mono- or di- or polysubstituted with one, two or several substituents chosen from:
groups —$OR_7$, in which $R_7$ represents a hydrogen atom or a linear, branched or cyclic alkyl,
halogen atoms,
groups —$COR_7$ in which $R_7$ represents a hydrogen atom or a linear, branched or cyclic alkyl,
linear, branched or cyclic alkyls, optionally substituted with one or more halogen atoms,
saturated, unsaturated or aromatic heterocycles, optionally substituted with one or more groups chosen from halogen atoms and groups alkyl optionally substituted with one or more halogen atoms;
or alternatively two adjacent groups from among R1, R2, R3 and R4 are linked and form, with the two carbons that bear them, a saturated, unsaturated or aromatic heterocycle, optionally substituted with one or more linear, branched or cyclic alkyl groups, the said alkyl groups being optionally substituted with at least one group chosen from groups —$NR_9R'_9$, in which $R_9$ and $R'_9$ represent, independently of each other, a hydrogen atom or an alkyl group, the said heterocycle being fused with the aromatic ring;
R5 represents:
a linear or branched alkyl, optionally substituted with one or more substituents chosen from halogen atoms, groups -$OR_9$, groups —$NR_9R'_9$, the group —CN, groups —$C(O)NR_9R'_9$, groups —$S(O)_pR_{10}$ and cycloalkyl groups optionally substituted with a group —$NR_9R'_9$, in which $R_9$, $R'_9$, $R_{10}$ and p are as defined below,
a cycloalkyl group, optionally substituted with a group —$NR_9R'_9$, in which $R_9$ and $R'_9$ are as defined below,
an alkoxy group —$OR_9$, in which $R_9$ is as defined below,
an aryl optionally substituted with one or more substituents chosen from groups (C1-C3)alkyl, halogen atoms and groups —O—(C1-C3)alkyl, or
a group —$(CH_2)_t$—$R_{13}$, in which $R_{13}$ and t are as defined below,
$R_6$ represents a hydrogen atom or a linear, branched or cyclic alkyl, and in which:
$R_7$ represents a hydrogen atom or a linear, branched or cyclic alkyl, optionally substituted with one or more of the following substituents chosen from halogen atoms, groups —$OR_9$ and groups —$NR_9R'_9$ with $R_9$ and $R'_9$ as defined below;

$R_9$ and $R'_9$ represent, independently of each other, a hydrogen atom or a linear, branched or cyclic alkyl;
$R_{10}$ represents a hydrogen atom or a linear, branched or cyclic alkyl optionally substituted with one or more halogen atoms,
$R_{13}$ represents a heteroaryl or a heterocycloalkyl optionally substituted with one or more substituents chosen from linear, branched or cyclic alkyls, it being understood that when the said heterocycloalkyl comprises at least one nitrogen atom, this atom may optionally bear the said substituent,
or an addition salt with an acid or a base thereof, or a hydrate or solvate thereof.

4. The compound of formula (I') according to claim 1,

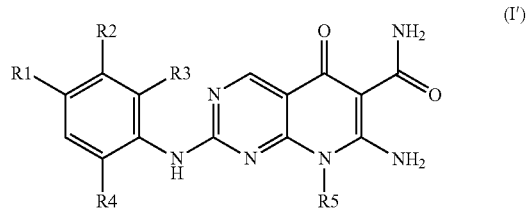

wherein:
$R_1$ represents:
a hydrogen atom,
a linear, branched or cyclic alkyl, optionally substituted with one or more of the following substituents chosen from halogen atoms, groups —$NR_9R'_9$, in which $R_9$ and $R'_9$ represent, independently of each other, a hydrogen atom or an alkyl group,
—$OR_{10}$, in which $R_{10}$ represents a hydrogen atom or a linear, branched or cyclic alkyl optionally substituted with one or more halogen atoms,
a halogen atom,
a group -T-U, in which
T represents:
a single bond,
an alkylene group,
a group —C(O)—,
a group —O—$(CH_2)_n$ in which n represents 0, 1, 2 or 3,
and U represents a saturated, unsaturated or aromatic heterocycle, optionally mono- or disubstituted with a substituent
R2, R3 and R4, which may be identical or different, independently represent:
a hydrogen atom,
a linear, branched or cyclic alkyl, optionally substituted with one or more of the following substituents chosen from halogen atoms and groups —$NR_9R'_9$, in which $R_9$ and $R'_9$ represent, independently of each other, a hydrogen atom or an alkyl,
a group —$OR_{10}$, in which $R_{10}$ represents a hydrogen atom or an alkyl optionally substituted with one or more halogen atoms,
a halogen,
a group -T-U with T representing a bond and U a morpholinyl, or
R1 and R2 are linked and form, with the two carbon atoms that bear them, a heterocycle chosen from a piperidine, a thiazole, a tetrahydrofuran and a dioxane, the said heterocycle being optionally substituted with a linear, branched or cyclic alkyl optionally substituted with —NR$_9$R'$_9$, in which R$_9$ and R'$_9$ represent, independently of each other, a hydrogen atom or a methyl, the said heterocycle being fused with the aromatic ring, and R5 represents (i) a linear, or branched alkyl comprising from 1 to 5 carbon atoms, optionally substituted with one or more substituents chosen from halogen atoms or a group —OH, (ii) an aryl optionally substituted with one or more substituents chosen from groups (C1-C3) alkyl, halogen atoms and groups —O—(C1-C3)alkyl; or (ii) a cycloalkyl group, optionally substituted with a group —NR$_9$R'$_9$;

or an addition salt with an acid or a base thereof, or a hydrate or solvate thereof.

5. A compound having the formula,

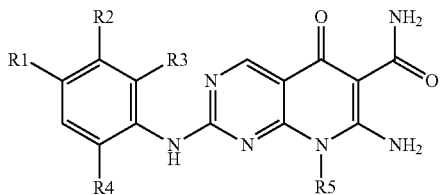

wherein:

R1 represents:
a linear, branched or cyclic alkyl, optionally substituted with one or more of the following substituents chosen from halogen atoms, groups —NR$_9$R'$_9$,
—OR$_{10}$, in which R$_{10}$ represents a hydrogen atom or a linear, branched or cyclic alkyl optionally substituted with one or more halogen atoms,
a halogen atom,
a group -T-U, in which
T represents:
a single bond,
an alkylene group,
a group —C(O)—,
a group —O—(CH$_2$)$_n$ in which n represents 0, 1, 2 or 3,
and U represents a saturated, unsaturated or aromatic heterocycle, optionally mono- or disubstituted with one or two of the substituents identified for U, R2, R3 and R4, which may be identical or different, independently represent:
a hydrogen atom,
a linear, branched or cyclic alkyl, optionally substituted with one or more of the following substituents chosen from halogen atoms and groups —NR$_9$R'$_9$
a group —OR$_{10}$, in which R$_{10}$ represents a hydrogen atom or an alkyl optionally substituted with one or more halogen atoms,
a halogen,
a group -T-U with T representing a bond and U a morpholinyl, or R1 and R2 are linked and form, with the two carbon atoms that bear them, a heterocycle chosen from a piperidine, a thiazole, a tetrahydrofuran and a dioxane, the said heterocycle being optionally substituted with a linear, branched or cyclic alkyl optionally substituted with —NR$_9$R'$_9$, in which R$_9$ and R'$_9$ represent, independently of each other, a hydrogen atom or a methyl, the said heterocycle being fused with the aromatic ring, R5 represents a linear, branched or cyclic alkyl; and R$_9$ and R'$_9$ represent, independently of each other, a hydrogen atom or a linear, branched or cyclic alkyl;

R$_{10}$ represents a hydrogen atom or a linear, branched or cyclic alkyl optionally substituted with one or more halogen atoms;

or an addition salt with an acid or a base thereof, or a hydrate or solvate thereof.

6. A compound having the formula,

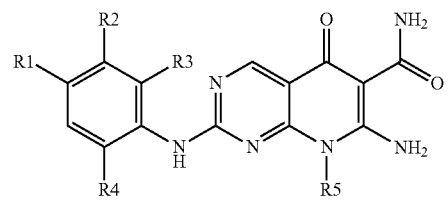

wherein R1 is chosen from:

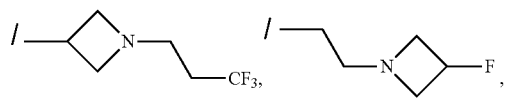

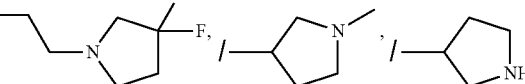

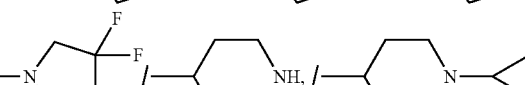

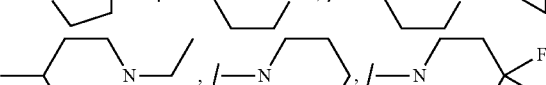

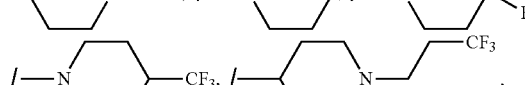

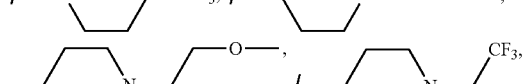

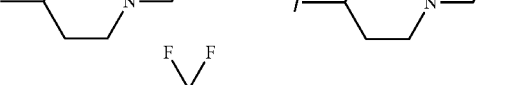

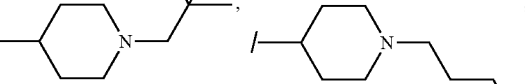

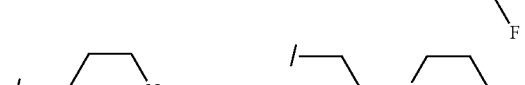

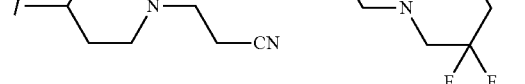

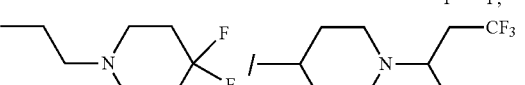

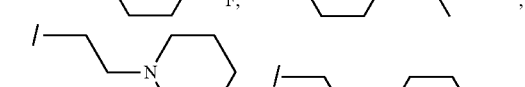

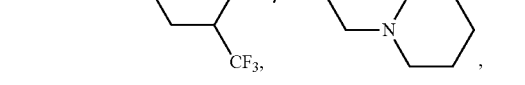

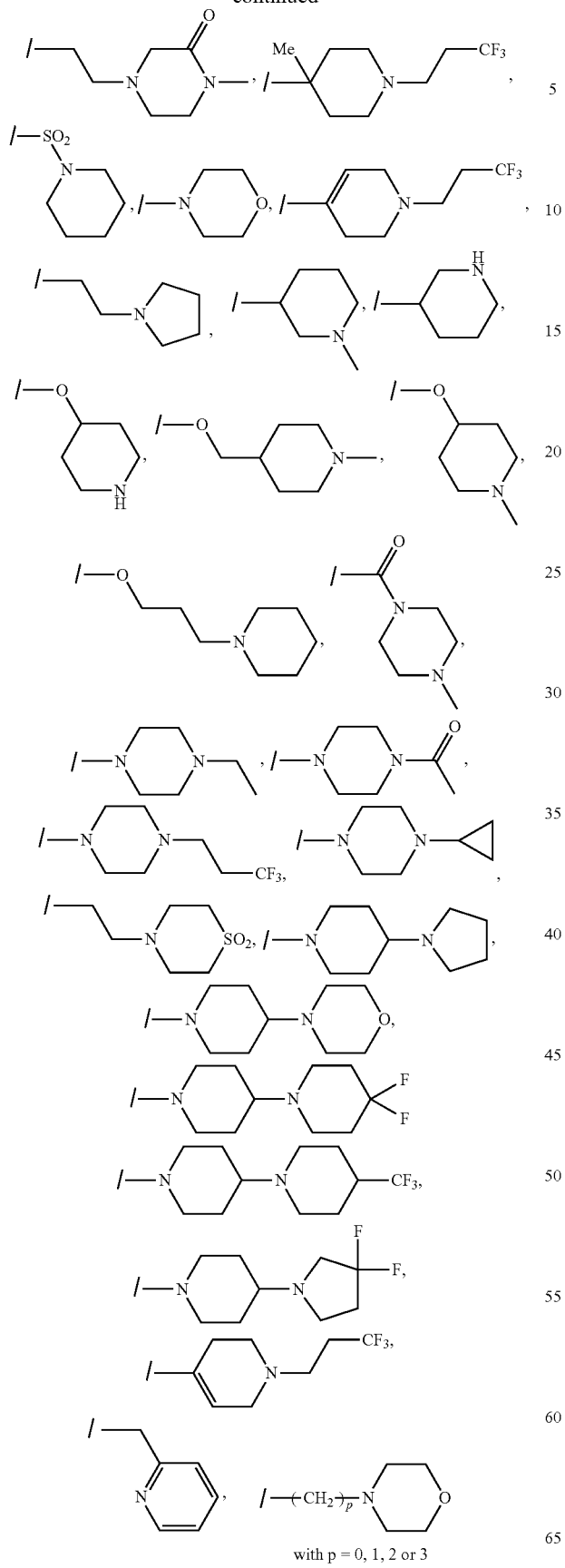

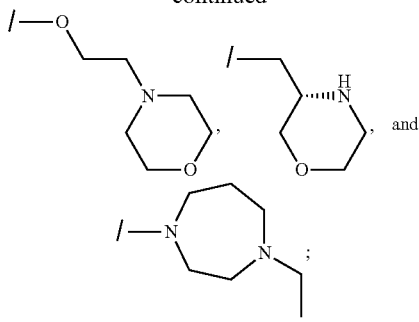

or an addition salt with an acid or a base thereof, or a hydrate or solvate thereof.

R2, R3 and R4, which may be identical or different, independently represent:
a hydrogen atom,
a linear, branched or cyclic alkyl, optionally substituted with one or more of the following substituents chosen from halogen atoms and groups —$NR_9R'_9$,
a group —$OR_{10}$, in which $R_{10}$ represents a hydrogen atom or an alkyl optionally substituted with one or more halogen atoms,
a halogen,
a group -T-U with T representing a bond and U a morpholinyl;

R5 represents (i) a linear or branched alkyl comprising from 1 to 5 carbon atoms, optionally substituted with one or more substituents chosen from halogen atoms or a group —OH, (ii) an aryl optionally substituted with one or more substituents chosen from groups (C1-C3) alkyl, halogen atoms and groups —O—(C1-C3)alkyl; or (ii) a cycloalkyl group, optionally substituted with a group —$NR_9R'_9$;

$R_9$ and $R'_9$ represent, independently of each other, a hydrogen atom or a linear, branched or cyclic alkyl;

$R_{10}$ represents a hydrogen atom or a linear, branched or cyclic alkyl optionally substituted with one or more halogen atoms;

or an addition salt with an acid or a base thereof, or a hydrate or solvate thereof.

7. The compound according to claim 4, wherein U represents a saturated heterocycle comprising at least one nitrogen atom;
or an addition salt with an acid or a base thereof, or a hydrate or solvate thereof.

8. A compound selected from:
7-Amino-8-ethyl-2-(4-hydroxyphenylamino)-5-oxo-5,8-dihydropyrido[2,3-d]pyrimidine-6-carboxamide;
7-Amino-2-(benzothiazol-6-ylamino)-8-ethyl-5-oxo-5,8-dihydropyrido[2,3-d]pyrimidine-6-carboxamide;
7-Amino-2-[4-(cyclopropanecarbonylmethylamino)phenylamino]-8-ethyl-5-oxo-5,8-dihydropyrido[2,3-d]pyrimidine-6-carboxamide;
7-Amino-8-ethyl-2-[4-(4-methylpiperazine-1-carbonyl)phenylamino]-5-oxo-5,8-dihydropyrido[2,3-d]pyrimidine-6-carboxamide;
7-Amino-2-(4-cyclopentyloxyphenylamino)-8-ethyl-5-oxo-5,8-dihydropyrido[2,3-d]pyrimidine-6-carboxamide;
7-Amino-8-ethyl-2-[4-(4-ethylpiperazin-1-yl)phenylamino]-5-oxo-5,8-dihydropyrido[2,3-d]pyrimidine-6-carboxamide;

7-Amino-8-ethyl-5-oxo-2-[4-(4-pynolidin-1-ylpiperid-1-yl)phenylamino]-5,8-dihydropyrido[2,3-d]pyrimidine-6-carboxamide;

7-Amino-8-ethyl-5-oxo-2-[4-(4-pyrrolidin-1-ylpiperid-1-yl)phenylamino]-5,8-dihydropyrido[2,3-d]pyrimidine-6-carboxamide;

7-Amino-8-ethyl-5-oxo-2-[4-(4-pyrrolidin-1-ylpiperid-1-yl)phenylamino]-5,8-dihydropyrido[2,3-d]pyrimidine-6-carboxamide;

7-Amino-8-cyclopentyl-2-(4-morpholin-4-ylphenylamino)-5-oxo-5,8-dihydropyrido[2,3-d]pyrimidine-6-carboxamide;

7-Amino-8-ethyl-5-oxo-2-[4-(piperidine-1-sulfonyl)phenylamino]-5,8-dihydropyrido[2,3-d]pyrimidine-6-carboxamide;

2-[4-(4-Acetylpiperazin-1-yl)phenylamino]-7-amino-8-ethyl-5-oxo-5,8-dihydropyrido[2,3-d]pyrimidine-6-carboxamide;

7-Amino-8-ethyl-2-(4-morpholin-4-ylbenzylamino)-5-oxo-5,8-dihydropyrido[2,3-d]pyrimidine-6-carboxamide;

7-Amino-8-ethyl-5-oxo-2-(quinolin-3-ylamino)-5,8-dihydropyrido[2,3-d]pyrimidine-6-carboxylamide;

7-Amino-8-ethyl-5-oxo-2-[4-(3-piperid-1-ylpropoxy)phenylamino]-5,8-dihydropyrido[2,3-d]pyrimidine-6-carboxamide;

7-Amino-8-ethyl-5-oxo-2-(3,4,5,6-tetrahydro-2H-[1,2']bipyridyl-5'-ylamino)-5,8-dihydropyrido[2,3-d]pyrimidine-6-carboxamide;

7-Amino-8-ethyl-5-oxo-2-[4-(2-oxopyrrolidin-1-yl)phenylamino]-5,8-dihydropyrido[2,3-d]pyrimidine-6-carboxamide;

7-Amino-8-ethyl-5-oxo-2-(quinolin-6-ylamino)-5,8-dihydropyrido[2,3-d]pyrimidine-6-carboxamide;

7-Amino-8-ethyl-2-(3-morpholin-4-ylphenylamino)-5-oxo-5,8-dihydropyrido[2,3-d]pyrimidine-6-carboxamide;

7-Amino-2-(2,3-dihydrobenzo[1,4]dioxin-6-ylamino)-8-ethyl-5-oxo-5,8-dihydropyrido[2,3-d]pyrimidine-6-carboxamide;

7-Amino-8-ethyl-2-(3-fluoro-4-hydroxyphenylamino)-5-oxo-5,8-dihydropyrido[2,3-d]pyrimidine-6-carboxamide;

7-Amino-8-ethyl-2-(3-methylsulfanylphenylamino)-5-oxo-5,8-dihydropyrido[2,3-d]pyrimidine-6-carboxamide;

7-Amino-8-ethyl-2-(4-morpholin-4-ylphenylamino)-5-oxo-5,8-dihydropyrido[2,3-d]pyrimidine-6-carboxamide;

7-Amino-8-ethyl-2-(4-morpholin-4-ylphenylamino)-5-oxo-5,8-dihydropyrido[2,3-d]pyrimidine-6-carboxamide;

7-Amino-8-ethyl-2-(4-morpholin-4-ylphenylamino)-5-oxo-5,8-dihydropyrido[2,3-d]pyrimidine-6-carboxamide;

7-Amino-8-ethyl-2-(2-fluorophenylamino)-5-oxo-5,8-dihydropyrido[2,3-d]pyrimidine-6-carboxamide;

7-Amino-2-[4-(4,4-difluoro[1,4']bipiperidyl-1'-yl)-2-methoxyphenylamino]-8-ethyl-5-oxo-5,8-dihydropyrido[2,3-d]pyrimidine-6-carboxamide;

7-Amino-8-ethyl-2-[2-methoxy-4-(4-trifluoromethyl[1,4']bipiperidyl-1'-yl)phenylamino]-5-oxo-5,8-dihydropyrido[2,3-d]pyrimidine-6-carboxamide;

7-Amino-2-{4-[4-(3,3-difluoropyrrolidin-1-yl)piperid-1-yl]-2-methoxyphenylamino}-8-ethyl-5-oxo-5,8-dihydropyrido[2,3-d]pyrimidine-6-carboxamide;

7-Amino-8-ethyl-2-[4-(4-ethylpiperazin-1-yl)-2-fluoro-6-methoxyphenylamino]-5-oxo-5,8-dihydropyrido[2,3-d]pyrimidine-6-carboxamide;

7-Amino-2-[4-(1-cyclopropylpiperid-4-yl)-2-methoxyphenylamino]-8-ethyl-5-oxo-5,8-dihydropyrido[2,3-d]pyrimidine-6-carboxamide;

7-Amino-2-(2-dimethylaminomethylchroman-6-ylamino)-8-ethyl-5-oxo-5,8-dihydropyrido[2,3-d]pyrimidine-6-carboxamide;

7-Amino-2-[5-chloro-4-(4-cyclopropylpiperazin-1-yl)-2-methoxyphenylamino]-8-ethyl-5-oxo-5,8-dihydropyrido[2,3-d]pyrimidine-6-carboxamide;

7-Amino-8-ethyl-2-[2-methoxy-4-(4-morpholin-4-ylpiperid-1-yl)phenylamino]-5-oxo-5,8-dihydropyrido[2,3-d]pyrimidine-6-carboxyamide;

7-Amino-2-[4-(4-cyclopropylpiperazin-1-yl)-2-difluoromethoxyphenylamino]-8-ethyl-5-oxo-5,8-dihydropyrido[2,3-d]pyrimidine-6-carboxamide;

7-Amino-2-[4-(4-cyclopropylpiperazin-1-yl)-2-methoxyphenylamino]-8-ethyl-5-oxo-5,8-dihydropyrido[2,3-d]pyrimidine-6-carboxamide;

7-Amino-8-ethyl-2-{2-methoxy-4-[1-(3,3,3-trifluoropropyl)piperid-4-yl]phenylamino}-5-oxo-5,8-dihydropyrido[2,3-d]pyrimidine-6-carboxamide;

7-Amino-2-[2-chloro-4-(4-ethylpiperazin-1-yl)phenylamino]-8-ethyl-5-oxo-5,8-dihydropyrido[2,3-d]pyrimidine-6-carboxamide;

7-Amino-8-ethyl-2-[4-(4-ethylpiperazin-1-yl)-3-trifluoromethylphenylamino]-5-oxo-5,8-dihydropyrido[2,3-d]pyrimidine-6-carboxamide;

7-Amino-8-ethyl-2-(4-morpholin-4-ylmethylphenylamino)-5-oxo-5,8-dihydropyrido[2,3-d]pyrimidine-6-carboxamide;

7-Amino-8-ethyl-5-oxo-2-{4-[4-(3,3,3-trifluoropropyl)piperazin-1-yl]phenylamino}-5,8-dihydropyrido[2,3-d]pyrimidine-6-carboxamide;

7-Amino-8-ethyl-2-[4-(4-ethylpiperazin-1-yl)-3-fluorophenylamino]-5-oxo-5,8-dihydropyrido[2,3-d]pyrimidine-6-carboxamide;

6-(4-Morpholin-4-ylphenylamino)-9-oxo-1,3,4,9-tetrahydro-2H-1,4a,5,7-tetraaza-phenanthrene-10-carboxamide;

7-Amino-8-ethyl-2-[4-(4-ethylpiperazin-1-yl)-2-methoxyphenylamino]-5-oxo-5,8-dihydropyrido[2,3-d]pyrimidine-6-carboxamide;

7-Amino-8-ethyl-2-[4-(1-methylpiperid-4-ylmethoxy)phenylamino]-5-oxo-5,8-dihydropyrido[2,3-d]pyrimidine-6-carboxamide;

7-Amino-2-[4-(4-cyclopropylpiperazin-1-yl)phenylamino]-8-ethyl-5-oxo-5,8-dihydropyrido[2,3-d]pyrimidine-6-carboxamide;

7-Amino-8-ethyl-2-[4-(4-ethylpiperazin-1-yl)-2-methylphenylamino]-5-oxo-5,8-dihydropyrido[2,3-d]pyrimidine-6-carboxamide;

7-Amino-8-ethyl-2-[4-(4-ethyl[1,4]diazepan-1-yl)phenylamino]-5-oxo-5,8-dihydropyrido[2,3-d]pyrimidine-6-carboxamide;

8-(4-Morpholin-4-ylphenylamino)-5-oxo-1,2,3,5-tetrahydro-3,7,9,9b-tetraaza-cyclopenta[a]naphthalene-4-carboxamide;

7-Amino-8-ethyl-5-oxo-2-{4-[2-(3-trifluoromethylpiperid-1-yl)ethyl]phenylamino}-5,8-dihydropyrido[2,3-d]pyrimidine-6-carboxamide;

7-Amino-8-ethyl-2-[4-(3-morpholin-4-ylpropyl)phenylamino]-5-oxo-5,8-dihydropyrido[2,3-d]pyrimidine-6-c arboxamide;

7-Amino-8-ethyl-5-oxo-2-{4-[1-(2,2,2-trifluoro ethyl)piperid-4-yl]phenylamino}-5,8-dihydropyrido[2,3-d]pyrimidine-6-carboxamide;

7-Amino-8-ethyl-2-(4-(S)-1-morpholin-3-ylmethylphenylamino)-5-oxo-5,8-dihydropyrido[2,3-d]pyrimidine-6-carboxamide;

7-Amino-8-isobutyl-2-[4-(2-morpholin-4-ylethyl)phenylamino]-5-oxo-5,8-dihydropyrido[2,3-d]pyrimidine-6-carboxamide;

7-Amino-8-ethyl-2-{4-[2-(3-fluoroazetidin-1-yl)ethyl]phenylamino}-5-oxo-5,8-dihydropyrido[2,3-d]pyrimidine-6-carboxamide;

7-Amino-2-[4-(2-morpholin-4-ylethyl)phenylamino]-5-oxo-8-propyl-5,8-dihydropyrido[2,3-d]pyrimidine-6-carboxamide;

7-Amino-8-ethyl-2-[4-(2-hydroxyethyl)phenylamino]-5-oxo-5,8-dihydropyrido[2,3-d]pyrimidine-6-carboxamide;

7-amino-8-ethyl-2-(4-hydroethylphenylamino)-5-oxo-5,8-dihydropyrido[2,3-d]pyrimidine-6-carboxamide;

7-Amino-8-ethyl-2-(2-methyl-1,2,3,4-tetrahydroisoquinolin-6-ylamino)-5-oxo-5,8-dihydropyrido[2,3-d]pyrimidine-6-carboxamide;

7-Amino-2-{4-[2-(1,1-dioxo-1lambda6-thiomorpholin-4-yl)ethyl]phenylamino}-8-ethyl-5-oxo-5,8-dihydropyrido[2,3-d]pyrimidine-6-carboxamide;

7-Amino-8-ethyl-2-{4-[2-(4-methyl-3-oxopiperazin-1-yl)ethyl]phenylamino}-5-oxo-5,8-dihydropyrido[2,3-d]pyrimidine-6-carboxamide;

7-Amino-8-ethyl-5-oxo-2-{4-[1-(3,3,3-trifluoropropyl)piperid-4-yl]phenylamino}-5,8-dihydropyrido[2,3-d]pyrimidine-6-carboxamide;

7-Amino-8-ethyl-5-oxo-2-{4-[1-(3,3,3-trifluoropropyl)piperid-4-yl]phenylamino}-5,8-dihydropyrido[2,3-d]pyrimidine-6-carboxamide;

7-Amino-2-(4-dimethylaminomethylphenylamino)-5-oxo-8-(2,2,2-trifluoroethyl)-5,8-dihydropyrido[2,3-d]pyrimidine-6-carboxamide;

7-Amino-2-[3-chloro-4-(4-pyrrolidin-1-ylpiperid-1-yl)phenylamino]-8-ethyl-5-oxo-5,8-dihydropyrido[2,3-d]pyrimidine-6-carboxamide;

7-Amino-2-[3-chloro-4-(4-pyrrolidin-1-ylpiperid-1-yl)phenylamino]-8-ethyl-5-oxo-5,8-dihydropyrido[2,3-d]pyrimidine-6-carboxamide;

7-Amino-8-ethyl-5-oxo-2-(4-pyrid-2-ylmethylphenylamino)-5,8-dihydropyrido[2,3-d]pyrimidine-6-carboxamide;

7-Amino-2-{4-[2-(3,3-difluoropyrrolidin-1-yDethyl]phenylamino}-8-ethyl-5-oxo-5,8-dihydropyrido[2,3-d]pyrimidine-6-carboxamide;

7-Amino-8-ethyl-5-oxo-2-(4-pyrrolidin-3-ylphenylamino)-5,8-dihydropyrido[2,3-d]pyrimidine-6-carboxamide;

7-Amino-8-ethyl-5-oxo-2-(4-pyrrolidin-3-ylphenylamino)-5,8-dihydropyrido[2,3-d]pyrimidine-6-carboxamide;

7-Amino-8-ethyl-5-oxo-2-[4-(2-piperid-1-ylethyl)phenylamino]-5,8-dihydropyrido[2,3-d]pyrimidine-6-carboxamide;

7-Amino-2-[4-(2-morpholin-4-ylethyl)phenylamino]-5-oxo-8-(2,2,2-trifluoroethyl)-5,8-dihydropyrido[2,3-d]pyrimidine-6-carboxamide 7-Amino-2-{4-[2-(4,4-difluoropiperid-1-yl)ethyl]phenylamino}-8-ethyl-5-oxo-5,8-dihydropyrido[2,3-d]pyrimidine-6-carboxamide;

7-Amino-8-ethyl-2-[4-(1-methylpyrrolidin-3-yl)phenylamino]-5-oxo-5,8-dihydropyrido[2,3-d]pyrimidine-6-carboxamide;

7-Amino-2-{4-[2-(3,3-difluoropiperid-1-yeethyl]phenylamino}-8-ethyl-5-oxo-5,8-dihydropyrido[2,3-d]pyrimidine-6-carboxamide;

7-Amino-8-(3-methoxy-propyl)-2-[4-(2-morpholin-4-ylethyl)phenylamino]-5-oxo-5,8-dihydropyrido[2,3-d]pyrimidine-6-carboxamide;

7-Amino-8-ethyl-2-[4-(1-methylpiperid-3-yl)phenylamino]-5-oxo-5,8-dihydropyrido[2,3-d]pyrimidine-6-carboxamide;

7-Amino-2-(4-dimethylaminomethylphenylamino)-8-isopropyl-5-oxo-5,8-dihydropyrido[2,3-d]pyrimidine-6-carboxamide;

7-Amino-2-(4-dimethylaminomethylphenylamino)-8-isopropyl-5-oxo-5,8-dihydropyrido[2,3-d]pyrimidine-6-carboxamide;

7-Amino-8-ethyl-5-oxo-2-(4-piperid-3-ylphenylamino)-5,8-dihydropyrido[2,3-d]pyrimidine-6-carboxamide;

7-Amino-8-ethyl-5-oxo-2-(1,2,3,4-tetrahydroisoquinolin-7-ylamino)-5,8-dihydropyrido[2,3-d]pyrimidine-6-carboxamide;

7-Amino-8-ethyl-5-oxo-2-(1,2,3,4-tetrahydroisoquinolin-7-ylamino)-5,8-dihydropyrido[2,3-d]pyrimidine-6-carboxamide;

7-Amino-8-ethyl-5-oxo-2-(1,2,3,4-tetrahydroisoquinolin-6-ylamino)-5,8-dihydropyrido[2,3-d]pyrimidine-6-carboxamide;

7-Amino-8-ethyl-2-[4-(1-methylpiperid-4-yloxy)phenylamino]-5-oxo-5,8-dihydropyrido[2,3-d]pyrimidine-6-carboxamide;

7-Amino-8-ethyl-2-[4-(2-morpholin-4-ylethoxy)phenylamino]-5-oxo-5,8-dihydropyrido[2,3-d]pyrimidine-6-carboxamide;

7-Amino-2-(3-dimethylaminomethylphenylamino)-8-ethyl-5-oxo-5,8-dihydropyrido[2,3-d]pyrimidine-6-carboxamide;

7-Amino-8-ethyl-5-oxo-2-[4-(4-pyrrolidin-1-ylpiperid-1-yl)phenylaminol-5,8-dihydropyrido[2,3-d]pyrimidine-6-carboxamide;

7-Amino-8-ethyl-5-oxo-2-[4-(piperid-4-yloxy)phenylamino]-5,8-dihydropyrido[2,3-d]pyrimidine-6-carboxamide;

7-Amino-8-(3-aminopropyl)-2-(4-morpholin-4-ylphenylamino)-5-oxo-5,8-dihydropyrido[2,3-d]pyrimidine-6-carboxamide;

7-Amino-8-ethyl-2-[4-(2-morpholin-4-ylethyl)phenylamino]-5-oxo-5,8-dihydropyrido[2,3-d]pyrimidine-6-carboxamide;

7-Amino-2-(4-dimethylaminomethylphenylamino)-8-ethyl-5-oxo-5,8-dihydropyrido[2,3-d]pyrimidine-6-carboxamide;

7-Amino-8-ethyl-2-[4-(1-ethylpiperid-4-yl)phenylamino]-5-oxo-5,8-dihydropyrido[2,3-d]pyrimidine-6-carboxamide;

7-Amino-8-ethyl-5-oxo-2-(4-piperid-4-ylphenylamino)-5,8-dihydropyrido[2,3-d]pyrimidine-6-carboxamide;

7-Amino-2-[3-chloro-4-(4-ethylpiperazin-1-yl)phenylamino]-8-ethyl-5-oxo-5,8-dihydropyrido[2,3-d]pyrimidine-6-carboxamide;

7-Amino-8-ethyl-2-[3-methoxy-4-(3-piperid-1-ylpropoxy)phenylamino]-5-oxo-5,8-dihydropyrido[2,3-d]pyrimidine-6-carboxamide;

7-Amino-8-ethyl-5-oxo-2-{4-[2-(4-trifluoromethylpiperid-1-yl)ethyl]phenylamino}-5,8-dihydropyrido[2,3-d]pyrimidine-6-carboxamide;

7-Amino-2-{4-[2-(cis-2,6-dimethylmorpholin-4-yl)ethyl] phenylamino}-8-ethyl-5-oxo-5,8-dihydropyrido[2,3-d] pyrimidine-6-carboxamide;

7-Amino-2-(4-diethylaminomethylphenylamino)-8-ethyl-5-oxo-5,8-dihydropyrido[2,3-d]pyrimidine-6-carboxamide;

7-Amino-2-(4-dimethylaminomethylphenylamino)-8-(3-methoxy-propyl)-5-oxo-5,8-dihydropyrido[2,3-d]pyrimidine-6-carboxamide;

7-Amino-8-ethyl-2-[4-(4-ethylpiperazin-1-yl)-2-fluorophenylamino]-5-oxo-5,8-dihydropyrido[2,3-d]pyrimidine-6-carboxamide;

7-Amino-2-{4-[1-(2-cyanoethyppiperid-4-yl]phenylamino}-8-ethyl-5-oxo-5,8-dihydropyrido[2,3-d]pyrimidine-6-carboxamide;

7-Amino-8-ethyl-2-{4-[143-fluoropropyl)piperid-4-yl]phenylamino}-5-oxo-5,8-dihydropyrido[2,3-d]pyrimidine-6-carboxylic acid amide;

7-Amino-8-ethyl-2-[4-(4-ethylpiperazin-1-yl)-3-methylphenylamino]-5-oxo-5,8-dihydropyrido[2,3-d]pyrimidine-6-carboxamide;

7-Amino-2-[4-(4-cyclopropylpiperazin-1-yl)-2-ethylphenylamino]-8-ethyl-5-oxo-5,8-dihydropyrido[2,3-d]pyrimidine-6-carboxamide;

(±)-7-Amino-2-trans-[4-(2-dimethylaminocyclopropyl)phenylamino]-8-ethyl-5-oxo-5,8-dihydropyrido[2,3-d]pyrimidine-6-carboxamide;

7-Amino-2-[4-(4-cyclopropylpiperazin-1-yl)-5-fluoro-2-methoxyphenylamino]-8-ethyl-5-oxo-5,8-dihydropyrido[2,3-d]pyrimidine-6-carboxamide;

7-Amino-2-[4-(4-cyclopropylpiperazin-1-yl)-3- fluoro-2-methoxyphenylamino]-8-ethyl-5-oxo-5,8-dihydropyrido[2,3-d]pyrimidine-6-carboxamide;

7-Amino-2-[4-(4-cyclopropylpiperazin-1-yl)-2-ethoxyphenylamino]-8-ethyl-5-oxo-5,8-dihydropyrido[2,3-d]pyrimidine-6-carboxamide;

7-Amino-8-ethyl-5-oxo-2-(4-propylphenylamino)-5,8-dihydropyrido[2,3-d]pyrimidine-6-carboxamide;

7-Amino-8-ethyl-5-oxo-2-(4-propoxyphenylamino)-5,8-dihydropyrido[2,3-d]pyrimidine-6-carboxamide;

7-Amino-8-ethyl-2-(6-methoxypyrid-3-ylamino)-5-oxo-5,8-dihydropyrido[2,3-d]pyrimidine-6-carboxamide;

7-Amino-8-ethyl-2-(4-fluorophenylamino)-5-oxo-5,8-dihydropyrido[2,3-d]pyrimidine-6-carboxamide;

7-Amino-8-ethyl-2-(4-methoxyphenylamino)-5-oxo-5,8-dihydropyrido[2,3-d]pyrimidine-6-carboxamide;

7-Amino-2-(benzo[1,3]dioxo1-5-ylamino)-8-ethyl-5-oxo-5,8-dihydropyrido[2,3-d]pyrimidine-6-carboxamide;

7-Amino-8-ethyl-5-oxo-2-(4-piperid-1-ylphenylamino)-5,8-dihydropyrido[2,3-d]pyrimidine-6-carboxamide;

8-Ethyl-2-{2-methoxy-4-[1-(3,3,3-trifluoropropyl)piperid-4-yl]phenylamino}-7-methylamino-5-oxo-5,8-dihydropyrido[2,3-d]pyrimidine-6-carboxamide;

7-Amino-8-isobutyl-2-{2-methoxy-4-[1-(3,3,3- trifluoropropyl)piperid-4-yl]phenylamino}-5-oxo-5,8-dihydropyrido[2,3-d]pyrimidine-6-carboxamide;

7-Amino-8-cyclopropylmethyl-2-{2-methoxy-4-[1-(3,3,3-trifluoropropyl)piperid-4-yl]phenylamino}-5-oxo-5,8-dihydropyrido[2,3-d]pyrimidine-6-carboxamide;

7-Amino-8-(2-methoxyethyl)-2-{2-methoxy-4-[1-(3,3,3-trifluoropropyppiperid-4-yl]phenylamino}-5-oxo-5,8-dihydropyrido[2,3-d]pyrimidine-6-carboxamide;

7-Amino-2-{2-methoxy-4-[1-(3,3,3- trifluoropropy)piperid-4-yl]phenylaminol}-5-oxo-8-(tetrahydrofuran-2-ylmethyl)-5,8-dihydropyrido[2,3-d]pyrimidine-6-carboxamide;

7-Amino-8-ethyl-5-oxo-2-{4-[1-(3,3,3-trifluoropropyl)azetidin-3-yl]phenylamino}-5,8-dihydropyrido[2,3-d]pyrimidine-6-carboxamide;

7-Amino-2-{5-fluoro-2-methoxy-4-[1-(3,3,3-trifluoropropyl)piperid-4-yl]phenylamino}-8-isobutyl-5-oxo-5,8-dihydropyrido[2,3-d]pyrimidine-6-carboxamide;

7-Amino-8-ethyl-5-oxo-2-[4-(1,2,3,6-tetrahydropyrid-4-yl)phenylamino]-5,8-dihydropyrido[2,3-d]pyrimidine-6-carboxamide;

7-Amino-2-(2-methoxy-4-piperid-4-ylphenylamino)-5-oxo-8-phenyl-5,8-dihydropyrido[2,3-d]pyrimidine-6-carboxamide;

7-Amino-8-(2-hydroxyethyl)-2-(2-methoxy-4-piperid-4-ylphenylamino)-5-oxo-5,8-dihydropyrido[2,3-d]pyrimidine-6-carboxamide;

7-Amino-2-{2-methoxy-4-[1-(3,3,3-trifluoropropyl)piperid-4-yl]phenylamino}-5-oxo-8-thiazol-2-ylmethyl-5,8-dihydropyrido[2,3-d]pyrimidine-6-carboxamide;

7-Amino-2-{2-methoxy-4-[1-(3,3,3-trifluoropropyl)piperid-4-yl]phenylamino}-5-oxo-8-thiazol-5-ylmethyl-5,8-dihydropyrido[2,3-d]pyrimidine-6-carboxamide;

7-Amino-8-(2-hydroxy-2-methylpropyl)-2-(2-methoxy-4-piperid-4-ylphenylamino)-5-oxo-5,8-dihydropyrido[2,3-d]pyrimidine-6-carboxamide;

8-(2-Acetylaminoethyl)-7-amino-2-{2-methoxy-4-[1-(3,3,3-trifluoropropyl)piperid-4-yl]phenylamino}-5-oxo-5,8-dihydropyrido[2,3-d]pyrimidine-6-carboxamide;

7-Amino-8-(2-aminoethyl)-2-(4-morpholin-4-ylphenylamino)-5-oxo-5,8-dihydropyrido[2,3-d]pyrimidine-6-carboxamide;

7-Amino-2-(4-morpholin-4-ylphenylamino)-5-oxo-8-pyrrolidin-3-ylmethyl-5,8-dihydropyrido[2,3-d]pyrimidine-6-carboxamide;

7-Amino-8-ethyl-2-[4-(4-ethylpiperazin-1-yl)-2-hydroxyphenylamino]-5-oxo-5,8-dihydropyrido[2,3-d]pyrimidine-6-carboxamide;

7-Amino-2-(4-morpholin-4-ylphenylamino)-5-oxo-8-piperid-4-ylmethyl-5,8-dihydropyrido[2,3-d]pyrimidine-6-carboxamide;

7-Amino-2-(2-methoxy-4-morpholin-4-ylphenylamino)-5-oxo-8-pyrrolidin-3-ylmethyl-5,8-dihydropyrido[2,3-d]pyrimidine-6-carboxamide;

7-Amino-8-ethyl-2-(2-methoxy-4-piperid-4-ylphenylamino)-4-methyl-5-oxo-5,8-dihydropyrido[2,3-d]pyrimidine-6-carboxamide;

7-Amino-2-{2-methoxy-4-[1-(3,3,3-trifluoropropyl)piperid-4-yl]phenylamino}-5-oxo-8-thiophen-2-ylmethyl-5,8-dihydropyrido[2,3-d]pyrimidine-6-carboxamide;

7-Amino-8-isobutyl-2-[2-methoxy-4-(4-morpholin-4-ylpiperid-1-yl)phenylamino]-5-oxo-5,8-dihydropyrido[2,3-d]pyrimidine-6-carboxamide;

7-Amino-2-(4-morpholin-4-ylphenylamino)-5-oxo-8-pyrmlidin-2-ylmethyl-5,8-dihydropyrido[2,3-d]pyrimidine-6-carboxamide;

7-Amino-8-ethyl-2-{2-methoxy-4-[1-(3,3,3-trifluoropropyl)-1,2,3,6-tetrahydropyrid-4-yl]phenylamino}-5-oxo-5,8-dihydropyrido[2,3-d]pyrimidine-6-carboxamide;

7-Amino-2-[4-(4-ethylpiperazin-1-yl)-2-methoxyphenylamino]-8-(2-hydroxy-2-methylpropyl)-5-oxo-5,8-dihydropyrido[2,3-d]pyrimidine-6-carboxamide;

7-Amino-8-(2-hydroxy-2-methylpropyl)-2-{2-methoxy-4-[1-(3,3,3-trifluoropropyl)piperid-4-yl]phenylamino}-5-oxo-5,8-dihydropyrido[2,3-d]pyrimidine-6-carboxamide;

7-Amino-8-(2-hydroxy-2-methylpropyl)-2-[4-(4-ethylpiperid-1-yl)-2-methoxyphenylamino]-5-oxo-5,8-dihydropyrido[2,3-d]pyrimidine-6-carboxamide;

7-Amino-2-[4-(1-cyclopropylpiperid-4-yl)-2-methoxyphenylamino]-8-(2-hydroxy-2-methylpropyl)-5-oxo-5,8-dihydropyrido[2,3-d]pyrimidine-6-carboxamide;

7-Amino-8-(2-hydroxy-2-methylpropyl)-2-{2-methoxy-4-[1-(2-methoxyethyl)piperid-4-yl]phenylamino}-5-oxo-5,8-dihydropyrido[2,3-d]pyrimidine-6-carboxamide;

7-Amino-2-[2-methoxy-4-(1-methylpiperid-4-yl)phenylamino]-5-oxo-8-phenyl-5,8-dihydropyrido[2,3-d]pyrimidine-6-carboxamide;

7-Amino-8-(3-fluorophenyl)-2-[2-methoxy-4-piperid-4-ylphenylamino]-5-oxo-5,8-dihydropyrido[2,3-d]pyrimidine-6-carboxamide;

7-Amino-8-(4-fluorophenyl)-2-[2-methoxy-4-piperid-4-ylphenylamino]-5-oxo-5,8-dihydropyrido[2,3-d]pyrimidine-6-carboxamide;

7-Amino-2-[2-methoxy-4-piperid-4-ylphenylamino]-5-oxo-8-m-tolyl-5,8-dihydropyrido[2,3-d]pyrimidine-6-carboxamide;

7-Amino-2-[2-methoxy-4-piperid-4-ylphenylamino]-5-oxo-8-p-tolyl-5,8-dihydropyrido[2,3-d]pyrimidine-6-carboxamide;

7-Amino-8-(3- methoxyphenyl)-2-(2-methoxy-4-piperid-4-ylphenylamino)-5-oxo-5,8-dihydropyrido[2,3-d]pyrimidine-6-carboxamide;

7-Amino-2-[2-methoxy-4-(2-pyrrolidin-1-ylethyl)phenylamino]-5-oxo-8-phenyl-5,8-dihydropyrido[2,3-d]pyrimidine-6-carboxamide;

7-Amino-8-(4-fluorophenyl)-2-[2-methoxy-4-(1-methylpiperid-4-yl)phenylamino]-5-oxo-5,8-dihydropyrido[2,3-d]pyrimidine-6-carboxamide;

7-Amino-2-[2-methoxy-4-(1-methylpiperid-4-yl)phenylamino]-5-oxo-8-m-tolyl-5,8-dihydropyrido[2,3-d]pyrimidine-6-carboxamide;

7-Amino-2-{2-methoxy-4-[1-(3,3,3-trifluoropropyl)piperid-4-yl]phenylamino}-5-oxo-8-phenyl-5,8-dihydropyrido[2,3-d]pyrimidine-6-carboxamide; or 7-Amino-2-[4-(4-ethylpiperazin-1-yl)-2-methoxyphenylamino]-5-oxo-8-phenyl-5,8-dihydropyrido[2,3-d]pyrimidine-6-carboxamide;

or an addition salt with an acid or a base thereof, or a hydrate or solvate thereof.

9. A compound of formula (VIII):

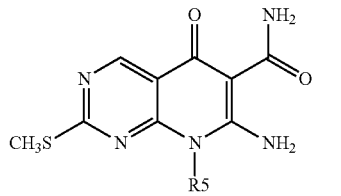

Wherein:

R5 represents:
   a linear or branched alkyl, optionally substituted with one or more substituents chosen from halogen atoms, groups —OR$_9$, groups —NR$_9$R'$_9$, the group —CN, groups —C(O)NR$_9$R$_9$', groups —S(O)$_p$R$_{10}$ and cycloalkyl groups optionally substituted with a group —NR$_9$R'$_9$, in which R$_9$, R'$_9$, R$_{10}$ and p are as defined below, a cycloalkyl group, optionally substituted with a group —NR$_9$R'$_9$, in which R$_9$ and R'$_9$ are as defined below, an alkoxy group —OR$_9$, in which R$_9$ is as defined below, an aryl optionally substituted with one or more substituents chosen from groups (C1-C3)alkyl, halogen atoms and groups —O—(C1-C3)alkyl, or a group —(CH$_2$)$_t$—R$_{13}$;

R$_9$ and R'$_9$ represent, independently of each other, a hydrogen atom or a linear, branched or cyclic alkyl;

R$_{10}$ represents a hydrogen atom or a linear, branched or cyclic alkyl optionally substituted with one or more halogen atoms;

R$_{13}$ represents a heteroaryl or a heterocycloalkyl optionally substituted with one or more substituents chosen from linear, branched or cyclic alkyls, it being understood that when the said heterocycloalkyl comprises at least one nitrogen atom, this atom may optionally bear the said substituent; t represents 1 or 2; and p represents 0, 1 or 2.

10. A compound of formula (IX):

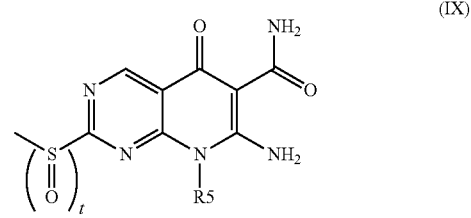

$t = 1$ or $2$ wherein:

R5 represents:
   a linear or branched alkyl, optionally substituted with one or more substituents chosen from halogen atoms, groups —OR$_9$, groups —NR$_9$R'$_9$, the group —CN, groups —C(O)NR$_9$R$_9$', groups —S(O)$_p$R$_{10}$ and cycloalkyl groups optionally substituted with a group —NR$_9$R'$_9$, in which R$_9$, R'$_9$, R$_{10}$ and p are as defined below, a cycloalkyl group, optionally substituted with a group —NR$_9$R'$_9$, in which R$_9$ and R'$_9$ are as defined below, an alkoxy group —OR$_9$, in which R$_9$ is as defined below, an aryl optionally substituted with one or more substituents chosen from groups (C1-C3)alkyl, halogen atoms and groups —O—(C1-C3)alkyl, or a group —(CH$_2$)$_t$—R$_{13}$;

R$_9$ and R'$_9$ represent, independently of each other, a hydrogen atom or a linear, branched or cyclic alkyl;

R$_{10}$ represents a hydrogen atom or a linear, branched or cyclic alkyl optionally substituted with one or more halogen atoms;

R$_{13}$ represents a heteroaryl or a heterocycloalkyl optionally substituted with one or more substituents chosen from linear, branched or cyclic alkyls, it being understood that when the said heterocycloalkyl comprises at least one nitrogen atom, this atom may optionally bear the said substituent; t represents 1 or 2, and p represents 0, 1 or 2.

11. A compound of formula (XV):

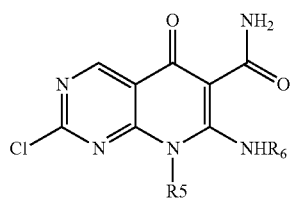

wherein:
R5 represents:
  a linear or branched alkyl, optionally substituted with one or more substituents chosen from halogen atoms, groups —OR$_9$, groups —NR$_9$R'$_9$, the group —CN, groups —C(O)NR$_9$R$_9$', groups —S(O)$_p$R$_{10}$ and cycloalkyl groups optionally substituted with a group —NR$_9$R'$_9$, in which R$_9$, R'$_9$, R$_{10}$ and p are as defined below,
  a cycloalkyl group, optionally substituted with a group —NR$_9$R'$_9$, in which R$_9$ and R'$_9$ are as defined below,
  an alkoxy group —OR$_9$, in which R$_9$ is as defined below,
  an aryl optionally substituted with one or more substituents chosen from groups (C1-C3)alkyl, halogen atoms and groups —O—(C1-C3)alkyl, or
  a group —(CH$_2$)$_t$—R$_{13}$;

R$_9$ and R'$_9$ represent, independently of each other, a hydrogen atom or a linear, branched or cyclic alkyl;

R$_{10}$ represents a hydrogen atom or a linear, branched or cyclic alkyl optionally substituted with one or more halogen atoms;

R$_{13}$ represents a heteroaryl or a heterocycloalkyl optionally substituted with one or more substituents chosen from linear, branched or cyclic alkyls, it being understood that when the said heterocycloalkyl comprises at least one nitrogen atom, this atom may optionally bear the said substituent;

R$_6$ represents a linear, branched or cyclic alkyl; t represents 1 or 2; and p represents 0, 1 or 2.

12. A pharmaceutical composition comprising the compound according to claim 1 or a pharmaceutically acceptable salt thereof, or a hydrate or solvate thereof, and at least one pharmaceutically acceptable excipient.

13. The compound according to claim 3 wherein said heterocycle U being saturated, unsaturated or aromatic, is optionally mono- or di- or polysubstituted with one, two or several substituents chosen from:
  saturated, unsaturated or aromatic heterocycles comprising an N, optionally substituted with one or more groups chosen from halogen atoms and groups alkyl optionally substituted with one or more halogen atoms.

* * * * *

UNITED STATES PATENT AND TRADEMARK OFFICE
CERTIFICATE OF CORRECTION

PATENT NO. : 8,975,250 B2
APPLICATION NO. : 13/544209
DATED : March 10, 2015
INVENTOR(S) : Philippe Beauverger et al.

It is certified that error appears in the above-identified patent and that said Letters Patent is hereby corrected as shown below:

Title Page, Item (54) and in the Specification, Column 1, lines 1-4, title: please replace "5 OXO-5,8-DIHYDROPYRIDO[2,3-D]PYRIMIDINE DERIVATIVES AS CAMKII KINASE INHIBITORS FOR TREATING CARDIOVASCULAR DISEASES" with --5-OXO-5,8-DIHYDROPYRIDO[2,3-D]PYRIMIDINE DERIVATIVES AS CAMKII KINASE INHIBITORS FOR TREATING CARDIOVASCULAR DISEASES--; and Title Page 2, Item (56) References Cited, Other Publications, right column, lines 28-31: please replace "Pesson, et al., Antibacteriens derives des acides alkyl-8 oxo-5 dehydro-5,8 pyrido [2,3-d] pyrimidine-6 carboxyliques. II.–De-rives piperazinyl-2 et (alkyl-4 piperazinyl)-2, Eur. J. Med. Chem., Chimica Therapeutica, (1974), vol. 6, pp. 591-596." with --Pesson, et al., Antibacteriens derives des acides alkyl-8 oxo-5 dihydro-5,8 pyrido [2,3-d] pyrimidine-6 carboxyliques. II.–De-rives piperazinyl-2 et (alkyl-4 piperazinyl)-2, Eur. J. Med. Chem., Chimica Therapeutica, (1974), vol. 6, pp. 591-596.--.

In the Claims:

At Column 112, claim number 1, line numbers 18-67: please replace

"R1, R2, R3 and R4, which may be identical or different,
represent, independently of each other:
a hydrogen atom;
a linear, branched or cyclic alkyl, optionally substituted
with one or more of the following:
halogen atoms;
–$OR_9$;
–$NR_9R'_9$;

Signed and Sealed this
Twenty-ninth Day of March, 2016

Michelle K. Lee
*Director of the United States Patent and Trademark Office*

–CN;

–C(O)OR$_9$;

–C(O)NR$_9$R$_9$';

–S(O)$_p$R$_{10}$,

–S(O)$_2$NR$_9$R'$_9$;

in which R$_9$, R'$_9$, R$_{10}$ and p are as defined below a group –S(O)$_p$R$_{10}$ in which p and R$_{10}$ are as defined below;

a group –OR$_{10}$ in which R$_{10}$ is as defined below;

a halogen atom;

a group –N(R$_{11}$)C(O)R$_{12}$, in which (i) R$_{11}$ and R$_{12}$ represent, independently of each other, a hydrogen atom or a linear, branched or cyclic alkyl, optionally substituted with one or more substituents chosen from halogen atoms, groups –OR$_9$ and groups –NR$_9$R'$_9$, or (ii) R$_{11}$ and R$_{12}$ form, together with the atoms to which they are attached, a heterocycloalkyl, so as to form a lactam;

a group –N(R$_{14}$)–CH$_2$–C(O)NR$_{15}$R$_9$, in which R$_{14}$ and R$_{15}$ form, together with the atoms to which they are attached, a heterocycloalkyl, so as to form a piperazinone and in which R$_9$ is as defined below;

a group –C(O)NR$_{16}$R$_{17}$ with R$_{16}$ and R$_{17}$ form, together with the nitrogen atom to which they are attached, a heterocycloalkyl, a group -T-U, in which:

T represents:

a single bond, a linear or branched alkylene group;

a group –S(O)$_p$– in which p is as defined below, or a group –O–(CH2)$_n$– in which n is as defined below, with U representing a heterocycle comprising one or more heteroatoms chosen from N, O and S(O)p, in which p is as defined below, the said heterocycle being saturated, unsaturated or aromatic, optionally mono- or di- or polysubstituted with one, two or several substituents chosen from:

groups $–OR_7$, in which $R_7$ is as defined below, halogen atoms,"

with

--R1, R2, R3 and R4, which may be identical or different, represent, independently of each other:

a hydrogen atom;

a linear, branched or cyclic alkyl, optionally substituted with one or more of the following:

halogen atoms;

$–OR_9$;

$–NR_9R'_9$;

$–CN$;

$–C(O)OR_9$;

$–C(O)NR_9R'_9$;

$–S(O)_pR_{10}$, $–S(O)_2NR_9R'_9$;

in which $R_9$, $R'_9$, $R_{10}$ and p are as defined below a group $–S(O)_pR_{10}$ in which p and $R_{10}$ are as defined below;

a group $–OR_{10}$ in which $R_{10}$ is as defined below;

a halogen atom;

a group $–N(R_{11})C(O)R_{12}$, in which (i) $R_{11}$ and $R_{12}$ represent, independently of each other, a hydrogen atom or a linear, branched or cyclic alkyl, optionally substituted with one or more substituents chosen from halogen atoms, groups $–OR_9$ and groups $–NR_9R'_9$, or (ii) $R_{11}$ and $R_{12}$ form, together with the atoms to which they are attached, a heterocycloalkyl, so as to form a lactam;

a group $–N(R_{14})–CH_2–C(O)NR_{15}R_9$, in which $R_{14}$ and

CERTIFICATE OF CORRECTION (continued)
U.S. Pat. No. 8,975,250 B2

$R_{15}$ form, together with the atoms to which they are attached, a heterocycloalkyl, so as to form a piperazinone and in which $R_9$ is as defined below;

a group $-C(O)NR_{16}R_{17}$ in which $R_{16}$ and $R_{17}$ form, together with the nitrogen atom to which they are attached, a heterocycloalkyl, a group -T-U, in which:

T represents:

a single bond, a linear or branched alkylene group;

a group $-C(O)-$, a group $-S(O)_p-$ in which p is as defined below, or a group $-O-(CH_2)_n-$ in which n is as defined below, with U representing a heterocycle comprising one or more heteroatoms chosen from N, O and $S(O)_p$, in which p is as defined below, the said heterocycle being saturated, unsaturated or aromatic, optionally mono- or di- or polysubstituted with one, two or several substituents chosen from:

groups $-OR_7$, in which $R_7$ is as defined below, halogen atoms,--;

At Column 113, claim number 1, line number 43: please replace "$-C(O)NR_9R_9$', groups $-S(O)_pR_{10}$" with -- $-C(O)NR_9R'_9$, groups $-S(O)_pR_{10}$--;

At Column 113, claim number 1, line number 53: please replace "$-(CH_2)_r-R_{13}$" with -- $-(CH_2)_t-R_{13}$--;

At Column 114, claim number 3, line number 19: please replace "The compound having the formula" with --A compound having the formula--;

At Column 114, claim number 3, line number 43: please replace "$-S(O)_pR_{10}$" with -- $-S(O)_pR_{10}$--;

At Column 114, claim number 3, line number 61: please replace "$-S(O)_p$" with -- $-S(O)_p$--;

At Column 114, claim number 3, line number 62: please replace "–O–(CH$_2$)$_n$–in which" with -- –O–(CH$_2$)$_n$– in which--;

At Column 115, claim number 3, in the figure showing the formula of the heterocycle of U, please replace "(Mi)$i$" with --(Mi)$_i$--;

At Column 115, claim number 3, line numbers 7-17: please replace

"in which

* represents the position of attachment of U to T;

M1 represents a C or N atom;

M2 and M3, which may be identical or different, represent
    a C, N or O atom or S(O)p in which p=0, 1 or 2;

M4 represents a C, C(=O), N, O or S(O)p atom in which
    p=0, 1 or 2;

each of the Mi, which may be identical or different, represent a C, C(=O), N, O or S(O)p atom in which p=0, 1 or
    2;

i=0, 1, 2 or 3;"

with

--in which

* represents the position of attachment of U to T;

M$_1$ represents a C or N atom;

M$_2$ and M$_3$, which may be identical or different, represent
    a C, N or O atom or S(O)$_p$ in which p=0, 1 or 2;

M$_4$ represents a C, C(=O), N, O or S(O)$_p$ atom in which
    p=0, 1 or 2;

each of the Mi, which may be identical or different, represent a C, C(=O), N, O or S(O)$_p$ atom in which p=0, 1 or
    2;

i=0, 1, 2 or 3;--;

At Column 115, claim number 3, lines 46-60: please replace

"R5 represents:

a linear or branched alkyl, optionally substituted with one
    or more substituents chosen from halogen atoms, groups

CERTIFICATE OF CORRECTION (continued)
U.S. Pat. No. 8,975,250 B2

-OR$_9$, groups –NR$_9$R'$_9$, the group –CN, groups
–C(O)NR$_9$R$_{9'}$, groups –S(O)$_p$R$_{10}$ and cycloalkyl
groups optionally substituted with a group –NR$_9$R'$_9$, in
which R$_9$, R'$_9$, R$_{10}$ and p are as defined below, a cycloalkyl group, optionally substituted with a group
–NR$_9$R'$_9$, in which R$_9$ and R'$_9$ are as defined below, an alkoxy group –OR$_9$, in which R$_9$ is as defined below, an aryl optionally substituted with one or more substituents
chosen from groups (C1-C3)alkyl, halogen atoms and
groups –O–(C1-C3)alkyl, or a group –(CH$_2$)$_t$–R$_{13}$, in which R$_{13}$ and t are as defined
below,"

with

--R5 represents:

a linear or branched alkyl, optionally substituted with one
or more substituents chosen from halogen atoms, groups
-OR$_9$, groups –NR$_9$R'$_9$, the group –CN, groups
–C(O)NR$_9$R'$_9$, groups –S(O)$_p$R$_{10}$ and cycloalkyl
groups optionally substituted with a group –NR$_9$R'$_9$, in
which R$_9$, R'$_9$, R$_{10}$ and p are as defined below, a cycloalkyl group, optionally substituted with a group
–NR$_9$R'$_9$, in which R$_9$ and R'$_9$ are as defined below, an alkoxy group –OR$_9$, in which R$_9$ is as defined below, an aryl optionally substituted with one or more substituents
chosen from groups (C1-C3)alkyl, halogen atoms and
groups –O–(C1-C3)alkyl, or a group –(CH$_2$)$_t$–R$_{13}$, in which R$_{13}$ and t are as defined
below,--;

At Column 116, claim number 4, line numbers 39-48: please replace

"a group -T-U, in which

T represents:

a single bond, an alkylene group, a group –C(O)–, a group $-O-(CH_2)_n$ in which n represents 0, 1, 2 or

3, and U represents a saturated, unsaturated or aromatic heterocycle, optionally mono- or disubstituted with a substituent"

with

--a group -T-U, in which

T represents:

a single bond, an alkylene group, a group $-C(O)-$, a group $-O-(CH_2)_n$ in which n represents 0, 1, 2 or

3, and U represents a saturated, unsaturated or aromatic heterocycle, optionally mono- or disubstituted with one or two of the substituents identified for U,--;

At Column 117, claim number 4, line number 4: please replace "a linear, or branched alkyl" with --a linear or branched alkyl--;

At Column 117, claim number 5, line numbers 36-46: please replace

"a group -T-U, in which

T represents:

a single bond, an alkylene group, a group $-C(O)-$, a group $-O-(CH_2)_n$ in which n represents 0, 1, 2 or

3, and U represents a saturated, unsaturated or aromatic heterocycle, optionally mono- or disubstituted with one or two of the substituents identified for U,"

with

--a group -T-U, in which

T represents:

a single bond, an alkylene group, a group –C(O)–, a group –O–(CH$_2$)$_n$ in which n represents 0, 1, 2 or 3, and U represents a saturated, unsaturated or aromatic heterocycle, optionally mono- or disubstituted with one or two of the substituents identified for U,--;

At Column 121, claim number 8, line numbers 1-3: please replace "7-Amino-8-ethyl-5-oxo-2-[4-(4-pynolidin-1-ylpiperid-1-yl)phenylamino]-5,8-dihydropyrido[2,3-d]pyrimidine-6-carboxamide" with --7-Amino-8-ethyl-5-oxo-2-[4-(4-pyrrolidin-1-ylpiperid-1-yl)phenylamino]-5,8-dihydropyrido[2,3-d]pyrimidine-6-carboxamide--;

At Column 121, claim number 8, line numbers 59-61: please replace "7-Amino-2-[4-(4,4-difluoro[1,4 ']bipiperidyl-1'-yl)-2-methoxyphenylamino]-8-ethyl-5-oxo-5,8-dihydropyrido[2,3-d]pyrimidine-6-carboxamide" with --7-Amino-2-[4-(4,4-difluoro[1,4']bipiperidyl-1'-yl)-2-methoxyphenylamino]-8-ethyl-5-oxo-5,8-dihydropyrido[2,3-d]pyrimidine-6-carboxamide--;

At Column 122, claim number 8, line numbers 65-67: please replace "7-Amino-8-ethyl-2-[4-(3-morpholin-4-ylpropyl)phenylamino]-5-oxo-5,8-dihydropyrido[2,3-d]pyrimidine-6-c arboxamide" with --7-Amino-8-ethyl-2-[4-(3-morpholin-4-ylpropyl)phenylamino]-5-oxo-5,8-dihydropyrido[2,3-d]pyrimidine-6-carboxamide--;

At Column 123, claim number 8, line numbers 1-3: please replace "7-Amino-8-ethyl-5-oxo-2-{4-[1-(2,2,2-trifluoro ethyl)piperid-4-yl]phenylamino}-5,8-dihydropyrido[2,3-d]pyrimidine-6-carboxamide" with --7-Amino-8-ethyl-5-oxo-2-{4-[1-(2,2,2-trifluoroethyl)piperid-4-yl]phenylamino}-5,8-dihydropyrido[2,3-d]pyrimidine-6-carboxamide--;

At Column 123, claim number 8, line numbers 20-21: please replace "7-amino-8-ethyl-2-(4-hydroethylphenylamino)-5-oxo-5,8-dihydropyrido[2,3-d]pyrimidine-6-carboxamide" with --7-Amino-8-ethyl-2-(4-hydroethylphenylamino)-5-oxo-5,8-dihydropyrido[2,3-d]pyrimidine-6-carboxamide--;

At Column 123, claim number 8, line numbers 50-52: please replace "7-Amino-2-{4-[2-(3 ,3-difluoropyrrolidin-1-yDethyl]phenylamino}-8-ethyl-5-oxo-5,8-dihydropyrido[2,3- d]pyrimidine-6-carboxamide" with --7-Amino-2-{4-[2-(3,3-difluoropyrrolidin-1-yl)ethyl]phenylamino}-8-ethyl-5-oxo-5,8-dihydropyrido[2,3-d]pyrimidine-6-carboxamide--;

At Column 124, claim number 8, line numbers 4-6: please replace "7-Amino-2-{4-[2-(3,3-difluoropiperid-1-yeethyl]phenylamino}-8-ethyl-5-oxo-5,8-dihydropyrido[2,3-d]pyrimidine-6-carboxamide" with --7-Amino-2-{4-[2-(3,3-difluoropiperid-1-yl)ethyl]phenylamino}-8-ethyl-5-oxo-5,8-dihydropyrido[2,3-d]pyrimidine-6-carboxamide--;

At Column 124, claim number 8, line numbers 39-41: please replace "7-Amino-8-ethyl-5-oxo-2-[4-(4-pyrrolidin-1-ylpiperid-1-yl)phenylaminol-5,8-dihydropyrido[2,3-d]pyrimidine-6-carboxamide" with --7-Amino-8-ethyl-5-oxo-2-[4-(4-pyrrolidin-1-ylpiperid-1-yl)phenylamino]-5,8-dihydropyrido[2,3-d]pyrimidine-6-carboxamide--;

At Column 125, claim number 8, line numbers 13-15: please replace "7-Amino-2-{4-[1-(2-cyanoethyppiperid-4-yl]phenylamino}-8-ethyl-5-oxo-5,8-dihydropyrido[2,3-d]pyrimidine-6-carboxamide" with --7-Amino-2-{4-[1-(2-cyanoethyl)piperid-4-yl]phenylamino}-8-ethyl-5-oxo-5,8-dihydropyrido[2,3-d]pyrimidine-6-carboxamide--;

At Column 125, claim number 8, line numbers 16-18: please replace "7-Amino-8-ethyl-2-{4-[143-fluoropropyl)piperid-4-yl]phenylamino}-5-oxo-5,8-dihydropyrido[2,3-d]pyrimidine-6-carboxylic acid amide" with --7-Amino-8-ethyl-2-{4-[1-(3-fluoropropyl)piperid-4-yl]phenylamino}-5-oxo-5,8-dihydropyrido[2,3-d]pyrimidine-6-carboxylic acid amide--;

At Column 125, claim number 8, line numbers 55-57: please replace "7-Amino-8-isobutyl-2-{2-methoxy-4-[1-(3,3,3- trifluoropropyl)piperid-4-yl]phenylamino}-5-oxo-5,8-dihydropyrido[2,3-d]pyrimidine-6-carboxamide" with --7-Amino-8-isobutyl-2-{2-methoxy-4-[1-(3,3,3-trifluoropropyl)piperid-4-yl]phenylamino}-5-oxo-5,8-dihydropyrido[2,3-d]pyrimidine-6-carboxamide--;

At Column 125, claim number 8, line numbers 61-63: please replace "7-Amino-8-(2-methoxyethyl)-2-{2-methoxy-4-[1-(3,3,3-trifluoropropyppiperid-4-yl]phenylamino}-5-oxo-5,8-dihydropyrido[2,3-d]pyrimidine-6-carboxamide" with --7-Amino-8-(2-methoxyethyl)-2-{2-methoxy-4-[1-(3,3,3-trifluoropropyl)piperid-4-yl]phenylamino}-5-oxo-5,8-dihydropyrido[2,3-d]pyrimidine-6-carboxamide--;

CERTIFICATE OF CORRECTION (continued)
U.S. Pat. No. 8,975,250 B2

At Column 125, claim number 8, line numbers 64-67: please replace "7-Amino-2-{2-methoxy-4-[1-(3,3,3- trifluoropropy)piperid-4-yl]phenylamino}-5-oxo-8-(tetrahydrofuran-2-ylmethyl)-5,8-dihydropyrido[2,3-d]pyrimidine-6-carboxamide" with --7-Amino-2-{2-methoxy-4-[1-(3,3,3-trifluoropropyl)piperid-4-yl]phenylamino}-5-oxo-8-(tetrahydrofuran-2-ylmethyl)-5,8-dihydropyrido[2,3-d]pyrimidine-6-carboxamide--;

At Column 126, claim number 8, line numbers 54-56: please replace "7-Amino-2-(4-morpholin-4-ylphenylamino)-5-oxo-8-pyrmlidin-2-ylmethyl-5,8-dihydropyrido[2,3-d]pyrimidine-6-carboxamide" with --7-Amino-2-(4-morpholin-4-ylphenylamino)-5-oxo-8-pyrrolidin-2-ylmethyl-5,8-dihydropyrido[2,3-d]pyrimidine-6-carboxamide--;

At Column 127, claim number 8, line numbers 26-28: please replace "7-Amino-8-(3- methoxyphenyl)-2-(2-methoxy-4-piperid-4-ylphenylamino)-5-oxo-5,8-dihydropyrido[2,3-d]pyrimidine-6-carboxamide" with --7-Amino-8-(3-methoxyphenyl)-2-(2-methoxy-4-piperid-4-ylphenylamino)-5-oxo-5,8-dihydropyrido[2,3-d]pyrimidine-6-carboxamide--;

At Column 127, claim number 9, line number 64: please replace "–C(O)NR$_9$R$_9$', groups –S(O)$_p$R$_{10}$" with -- –C(O)NR$_9$R'$_9$, groups –S(O)$_p$R$_{10}$--;

At Column 128, claim number 9, line number 8: please replace "–(CH$_2$)$_t$–R$_{13}$" with -- –(CH$_2$)$_t$–R$_{13}$--;

At Column 128, claim number 10, in the figure showing formula (IX): please replace the label "$t$" next to the (S=O) group with --t--, and replace "$t$ = 1 or 2" with --t = 1 or 2--;

At Column 128, claim number 10, line number 43: please replace "–C(O)NR$_9$R$_9$', groups –S(O)$_p$R$_{10}$" with -- –C(O)NR$_9$R'$_9$, groups –S(O)$_p$R$_{10}$--;

At Column 128, claim number 10, line number 55: please replace "–(CH$_2$)$_t$–R$_{13}$" with -- –(CH$_2$)$_t$–R$_{13}$--;

At Column 129, claim number 11, line number 17: please replace "–C(O)NR$_9$R$_9$', groups –S(O)$_p$R$_{10}$" with -- –C(O)NR$_9$R'$_9$, groups –S(O)$_p$R$_{10}$--; and At Column 129, claim number 11, line number 27: please replace "–(CH$_2$)$_t$–R$_{13}$" with -- –(CH$_2$)$_t$–R$_{13}$--.